United States Patent [19]
Vermeer

[11] Patent Number: 5,653,970
[45] Date of Patent: *Aug. 5, 1997

[54] PERSONAL PRODUCT COMPOSITIONS COMPRISING HETEROATOM CONTAINING ALKYL ALDONAMIDE COMPOUNDS

[75] Inventor: Robert Vermeer, Nutley, N.J.

[73] Assignee: Lever Brothers Company, Division of Conopco, Inc., New York, N.Y.

[*] Notice: The term of this patent shall not extend beyond the expiration date of Pat. No. 5,641,480.

[21] Appl. No.: 352,008

[22] Filed: Dec. 8, 1994

[51] Int. Cl.$^6$ .............. A61K 7/07; A61K 7/075
[52] U.S. Cl. .......... 424/70.24; 424/70.1; 514/847; 510/126; 510/135
[58] Field of Search ................ 424/401, 70.31, 424/70.19, 70.24

[56] References Cited

U.S. PATENT DOCUMENTS

| | | | |
|---|---|---|---|
| 2,662,073 | 12/1953 | Mehltretter et al. | 536/17.2 |
| 2,721,211 | 10/1955 | Buc | 260/562 |
| 2,752,334 | 6/1956 | Walton | 260/211 |
| 2,776,951 | 1/1957 | Melamed | 536/17.2 |
| 2,785,152 | 3/1957 | Jones | 260/112 |
| 3,766,267 | 10/1973 | Zak | 260/561 B |
| 3,855,290 | 12/1974 | Zak et al. | 260/561 B |
| 3,990,991 | 11/1976 | Gerstein | 252/542 |
| 4,038,294 | 7/1977 | Conner et al. | 260/501.15 |
| 4,190,429 | 2/1980 | Rutter et al. | 71/67 |
| 4,342,706 | 8/1982 | Conner et al. | 260/404.5 |
| 4,529,588 | 7/1985 | Smith et al. | 260/561 B |
| 4,534,964 | 8/1985 | Herstein et al. | 424/70 |
| 4,618,675 | 10/1986 | Lichtenthaler | 536/17.2 |
| 4,973,473 | 11/1990 | Schneider et al. | 424/63 |
| 5,037,973 | 8/1991 | Meinetsberger | 260/102 |
| 5,084,270 | 1/1992 | Ciaudelli | 424/59 |

FOREIGN PATENT DOCUMENTS

| | | |
|---|---|---|
| 2523962 | 9/1983 | France . |
| 2321752 | 11/1974 | Germany . |
| 2338087 | 1/1975 | Germany . |
| 62-327860 | 7/1989 | Japan . |
| 94/12511 | 6/1994 | WIPO . |

OTHER PUBLICATIONS

Synthetic Emulsifying Agents, Fieser et al., Jun. 20, 1956, vol. 78, pp. 2825–2832.
Linking Sugars with Amino Acid Esters of Lipophilic Alcohols to Form Surface–Active Sugar Derivatives, Geyer, vol. 330 9 (1963), pp. 182–188 (English Translation).
Reaction of Aliphatic Diamines with D–Gluconic Acid δ–Lactone, Geyer,vol. 97 (1964), pp. 2271–2275 (English Translation).
Amphiphilic Properties of Synthetic Glycolipids Based on Amide Linkages, I. Electron Microscopic Studies on Aqueous Gels, Chem. & Physics of Lipids 37 (1985) 227–240.
The Chiral Bilayer Effect Stabilizes Micellar Fibers, Fuhrhop et al., J.Am. Chem. Soc., vol. 109, No. 11; pp. 3386–3390 & Supplemental Material.
Lipid Bilayer Fibers from Diastereomeric and Enantiomeric N–Octylaldonamides, Fuhrhop et al., J. Am. Chem. Soc., 1988, 110, pp. 2861–2867.
Stereochemistry and Curvature Effects in Supramolecular Organization and Separation Process of Micellar N–Alkylaldonamide Mixtures, Fuhrhop et al., J. Am. Chem. Soc., 1990, 112, pp. 1768–1775.
A New Family of Liquid Crystals: N–Substituted Aldonamides, Mol. Cryst. Liq. Cryst. 1986, vol. 135, pp. 93–110.
Molecular Packing and Hydrogen Bonding in the Crystal Structures of the N–(n–Alkyl)–D–gluconamide and the 1–Deoxy–(N–methyl–alkanamido)–D–glucitol Mesogens, Mol. Cryst. Liq. Cryst. 1990, vol. 185, pp. 209–213.
Molecular Crystals and Liquid Crystals, vol. 198 (1991).
Amphiphilic Properties of Synthetic Glycolipids Based on Amide Linkages, Zabel et al., Chemistry and Physics of Lipids, 39 (1986) 313–327.
Liquid–crystalline Behaviour in the N–alkyl Gluconamides and Other Related Carbohydrates, Pfanhemuller, Liquid Crystals, 1986, vol. 1, vol. 1 No. 4, 357–370.
Amphiphilic Properties of Synthetic Glycolipids Based in Amide Linkages, Makromol, Chem. 189, 2433–2442 (1988).
Molecular and Crystal Structures of N–(n–Heptyl)– and N–(n–Decyl)–D–Glyconamide, Fahrnow et al., Carbohydrate Research 176 (1988) 165–174).
Supramolecular Assemblies of Diacetylenic Aldonamides, Frankel et al., J. Am. Chem. Soc., 1991, 113, 7436–7437.
A New Class of Model Glycolipids; Synthesis, Characterization, and Interaction with Lectins, Williams et al., Archives of Biochemistry and Biophysics, vol. 195, No. 1, Jun., pp. 145–151, 179.
Synthesis of a New Class of Model Glycolipids, Williams et al.—Carbohydrate Research, 67 (1978) C1–C3.
Technical Notes, Scholnick et al. pp. 471–473.
Compositions Comprising Nonionic Glycolipid Surfactants, Filed as U.S. Serial No. 816,419.
Light Scattering from Nonionic Surfactants of the Sugar–Lipid Hybrid Type in Aqueous Solution, Denkinger et al., J. Phys. Chem., 1989, 93, pp. 1428–1434.
Investigations of a Series of Nonionic Surfactants of Sugar–Lipid Hybrids by Light Scattering and Electron Microscopy, Denkinger et al., Colloid & Polymer Science 268:513 527 (1990).
Monolayers from Synthetic Glycolipids, Emmerling, Polymer Bulletin 6, 305–308 (1982).

*Primary Examiner*—Sallie M. Gardner
*Attorney, Agent, or Firm*—Ronald A. Koatz

[57] ABSTRACT

The invention relates to personal product compositions containing heteroatom containing alkyl aldonamide compounds and skin conditioning agent. Unexpectedly, applicants have found that when these heteroatom containing alkyl aldonamides are used, benefits such as enhanced stability and/or enhanced viscosity are obtained relative to the use of other known thickeners or non-heteroatom containing aldonamides.

1 Claim, No Drawings

OTHER PUBLICATIONS

Synthesis of New Fluorinated Nonionic Surfactants Derived from Lactose, Ghoul, Journal of Fluorine Chemistry, 59 (1992) 107–112.

Conformational Effects of 1,3,–syn–Diaxial Repulsion and 1,2–gauche Attraction Between Hydroxy Groups in Monomolecular N–Octyl–D–Hexonamide Solutions, Svenson et al., J. Chem. Soc., Perkin Trans 2, 1994, pp. 1023–1028.

PERSONAL PRODUCT COMPOSITIONS COMPRISING HETEROATOM CONTAINING ALKYL ALDONAMIDE COMPOUNDS

TECHNICAL FIELD

The present invention is related to new personal product compositions that have improved foam, viscosity, clarity and conditioning characteristics due to the inclusion of a new type of alkyl aldonamide compound, specifically heteroatom containing alkyl aldonamide compounds.

BACKGROUND OF THE INVENTION

Personal product treatments today are a part of body care that is of special importance for the maintenance of personal hygiene. In general, the personal product compositions of the present invention are products which are applied to either the whole of the body or to specific areas of the body such as the hands, arms, face, legs, lips or feet. For this reason, a special importance is attached in the cosmetic area to personal products particularly, bath preparations, cleansing preparations, skin care preparations, shaving preparations and deodorant or antiperspirant preparations.

The primary function of a personal product composition is to cleanse the skin gently without irritation or excessive defatting or overdrying the skin. In addition, successful personal product compositions should not leave the skin tight or taut after frequent routine use. After accomplishing the cleansing action, the personal product composition should leave the skin feeling soft, smooth, silky and moisturized while simultaneously providing a rich copious foam or lather. This has become a difficult challenge to meet and it is not surprising to find that considerable resource and effort have been directed towards the discovery and development of new ingredients that provide improved foam, viscosity, clarity and conditioning characteristics. The patent literature, cosmetic journals and formularies describe many such ingredients, however, they still do not provide all the answers to the problems encountered in making a totally satisfactory product. For one thing, it is known that certain mild surfactant systems when formulated for skin cleansing, often exhibit poor foam or low lather performance. On the other side, the use of high sudsing surfactants with lather boosters can yield acceptable lather volume, unfortunately however, such surfactant systems are usually harsh to the skin. It will be appreciated that these two factors make the formulation process, a delicate balancing act.

It has now been found that the inclusion of a heteroatom containing alkyl aldonamide compound in a personal product composition of the invention, surprisingly provides improved foam, viscosity, clarity and conditioning characteristics while simultaneously making the skin feeling soft, smooth, silky and moisturized. These findings are quite unexpected and have not been recognized or appreciated in the art.

The personal product compositions of the present invention may be in aerosol, liquid, gel, cream, lotion, spray, paste, roll-on, stick, tablet, powdered and bar form. Included among the personal product compositions are bubble bathes, shower gels, body shampoos, skin cleansers or lotions, liquid soaps, toilet bars, syndet bars, sunscreens, shaving creams, deodorants or antiperspirants and the like.

Foam

The ability of a personal product composition to create a desirable rich lather is a significant driving force in the selection of that product. This important psychological stimulus derived from tactile and visual perceptions by the consumer, make it necessary to formulate compositions with ingredients that generate a high level of stable foam or lather. Furthermore, the generation of a thick, persistent lather also serves as a vehicle to suspend dirt and prevent redeposition during the rinse cycle. Surprisingly the personal product compositions of the invention that comprise a heteroatom containing alkyl aldonamide compound produce an enhanced, thick, copious, persistent foam and lather.

By contrast, compositions that lack a heteroatom containing alkyl aldonamide compound exhibit low viscosity and poor foam.

Viscosity/Clarity

The viscosity or thickness of a personal product composition also plays an important role in the selection of that product, since consumers are accustomed to, and expect personal product compositions to be thick and viscous. If a personal product composition is thin and nonviscous, a consumer may conclude that the product is inferior. Furthermore, successful personal product compositions must have good shelf life and should not become turbid or produce sedimentation upon standing. Ideal personal product compositions should cleanse the skin gently and should not overdry the skin. Surprising the personal product compositions of the present invention that comprise a heteroatom containing alkyl aldonamide compound produce clear, stable, thick liquid compositions with good moisturizing properties. This is unusual and unexpected, since alkyl aldonamides that lack heteroatoms generally form opaque, nontransparent liquid compositions which are instead useful as opacifying or pearlescent agents.

Background Art

Alkyl Aldonamides

An aldonamide is defined as the amide of an aldonic acid (or aldonolactone) and an aldonic acid, in turn is defined as a sugar substance in which the pseudoaldehyde or pseudoketose group, generally found at the $C_1$ or $C_2$ position on the sugar, has been oxidized to a carboxylic acid group which upon drying cyclizes to an aldonolactone.

Aldonamides may be based on compounds comprising one saccharide unit (e.g., ribonamides, gluconamides or glucoheptonamides), two saccharide units (e.g., lactobionamides, maltobionamides, melibionamides, cellobioamides, gentiobionamides or D-glucopyranosyl-(1-5)-D-arabinonamides) or they may be based on compounds comprising more than two saccharide units. Any carbohydrate can be used as long as the sugar has a pseudoaldehyde or pseudoketose group available for oxidation to a carboxylic acid group.

While alkyl aldonamides are known in the art, there is no teaching or suggestion of using heteroatom containing alkyl aldonamide compounds of the invention as foam stabilizers, viscosity modifiers or conditioning agents in clear personal product compositions.

In particular, there is no teaching that using heteroatom containing alkyl aldonamide compounds in personal product compositions alone or with, for example, anionic surfactants (e.g., sodium or ammonium salts of alkyl sulfates, alkyl ether sulfates or alkyl isethionates), nonionic surfactants (e.g., alkyl polyoxyalkylene sorbitan esters or alkyl polyglycosides), amphoteric surfactants (e.g., alkyl carboxybetaines) and mixtures thereof, could result in a clear thickened personal product composition that foams copiously and leaves the skin feeling soft, smooth, silky and moisturized.

U.S. Pat. No. 2,662,073 to Mehltretter, et al. for example, teaches gluconamide compounds of the formula:

wherein R is an aliphatic hydrocarbon radical having 8 to 18 carbon atoms, a cycloaliphatic radical having 8 to 18 carbon atoms or a rosin radical. The compounds are said to be valuable wetting agents for use in the mercerization of cotton and in the manufacture of viscose yarn. There is clearly no teaching on suggestion of using heteroatom containing alkyl aldonamide compounds of the invention in personal product compositions for improved foam, viscosity, clarity and conditioning benefits.

U.S. Pat. No 2,776,951 to Melamed teaches the preparation of vinyloxyethyl gluconamides as polymer precursors. The polymers are said to be useful as wetting agents and as paper, leather or textile finishing agents. There is clearly no teaching or suggestion of using heteroatom containing alkyl aldonamide compounds of the invention in personal product compositions for improved foam, viscosity, clarity and conditioning benefits.

U.S. Pat. No. 2,721,211 to Buc teaches alkyl formyl phenylene gluconamides as solubilizing agents for vat dye stuffs. The alkyl formyl phenylene radical (R) of these compounds are structurally unrelated to the compounds of the invention which contain a hydrocarbon radical interrupted by a heteroatom. Also, U.S. Pat. No. 4,190,429 to Rutter, et al. teaches adamantyl gluconamides as antimicrobial agents. In both of these patents, there is clearly no teaching or suggestion of using heteroatom containing alkyl aldonamide compounds of the invention in personal product compositions for improved foam, viscosity, clarity and conditioning benefits.

Fieser, et al. in J. Am. Chem. Soc. 78:2825 (1956) teaches the preparation of a series of N-alkyl arabinonamides and N-alkyl gluconamides for use as an emulsifying agents, where the attached aliphatic radical (R) is from $C_{10}$ to $C_{18}$. The reference teaches that such compounds are poor emulsifying agents and are therefore expected to be poor surfactants. Also, there is clearly no teaching or suggestion that the addition of oxygen or other heteroatoms in the alkyl radical can enhance the foam, viscosity, clarity and conditioning benefits in personal product compositions.

Furthermore, the fact that the monosaccharide alkyl aldonamides, where the alkyl group is $C_{10}$ or greater, are poor emulsifiers is also recognized in German Pat. Nos. 2,321,752 and 2,338,087, both to Reiser, et al. (1975).

Specifically, DE 2,321,752 is directed to the preparation of N,N-dialkyl polyhydroxyamide compounds having the formula:

wherein n is 3 to 5; $R_1$ is hydrogen or a linear alkyl group containing 1 to 3 carbon atoms; and $R_2$ is an aliphatic hydrocarbon radical having 4 to 7 carbons in normal or branched arrangement (optionally interrupted by oxygen, sulfur or hydroxyl group). The principal patent DE 2,321,752, teaches that alkyl aldonamides having long chained radical (R) groups such as lauryl (12 carbons), cetyl (16 carbons) or stearyl (18 carbons), do not form stable water emulsions. Therefore, it was surprising to find that the liquid personal product compositions of the invention, which comprise heteroatom containing alkyl aldonamide compounds having R groups of 12 carbons or greater, provide clear compositions with improved foam, viscosity and conditioning benefits.

Japanese Patent 1-168653 again recognizes that the monosaccharide aldonamides of the art (e.g., N-alkyl gluconamides) do not show sufficient emulsifying properties (poor surface-activity). Again, there is a recognition that such compounds are poor emulsifiers and are therefore not expected to be useful as ingredients in liquid personal product compositions.

The Japanese patent seeks to address this problem by using N,N-dialkyl polyhydroxyamide compounds where one alkyl group (R) is $C_8$–$C_{18}$ and the other is $C_1$–$C_4$. There is clearly no teaching or suggestion of using heteroatom containing alkyl aldonamide compounds of the invention in liquid personal product compositions for improved foam, viscosity, clarity and conditioning benefits.

French Patent No. 2,523,962 to Monsigny teaches the compounds:

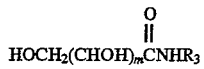

wherein m is 2 to 6 and $R_3$ is a linear or branched alkyl group containing 6 to 18 carbons. The patent further teaches polyoxyethylene, polyoxypropylene or polyglycerol derivatives of the formula. Again, however, there is no teaching of a hydrocarbon radical (R) when interrupted by a heteroatom, would provide personal product compositions with improved foam, viscosity, clarity and conditioning benefits.

U.S. Pat. No. 4,973,473 to Schneider, et al. teaches skin treatment compositions in which the primary moisturizing agent may be a gluconamide compound. Methyloxypropyl gluconamide is the only example of this ingredient which has the formula:

Since this compound is clearly hydrophilic (not surface-active), it cannot be used as a foam stabilizer, viscosity modifier or conditioning agent. There is no suggestion to utilize alkyl chains greater than methyl and there is clearly no teaching or suggestion that aldonamides with interrupted long alkyl chains can provide improved foam, viscosity, clarity and conditioning benefits in personal product compositions.

Schneider et al. in Hoppe-Seyler's Z. Physiol. Chem. 330:182 (1963) teaches alkyl gluconyl glycinate compounds having the formula:

wherein $R_4=C_8$ to $C_{10}$

While this paper does teach monosaccharide aldonamides containing an alkyl group interrupted with an ester functionality, there is no teaching or suggestion that such alkyl groups may be interrupted with, for example, an ether, sulfide or amine or that the use of such groups will provide improved foam, viscosity, clarity and conditioning benefits in personal product compositions.

Geyer in Chemische Berichte 97:2271 (1964) describes the preparation of N-alkanoyl-N-gluconoyl ethylene diamide compounds having the structure:

wherein $R_5=C_{15}$, $C_6$; and Pfannemueller, et al. in Chemistry and Physics of Lipids 517:227 (1985) describes the preparation of N-alkanoyl-N-methyl-N'-gluconyl ethylene diamide compounds of the formula:

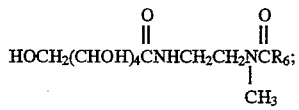

wherein $R_6=C_8$

These references teach monosaccharide aldonamides containing an alkyl group that is interrupted with an amide group, not an amine group. Again, there is no teaching or suggestion of alkyl aldonamides with alkyl groups interrupted with an ether, sulfide or amine linkage or that such interrupting groups provide greater foam, viscosity, clarity and conditioning benefits than others. Furthermore, there is clearly no teaching or suggestion of using sugar compounds having two saccharide units or greater (e.g., lactobionanides) together within an interrupted alkyl group for providing improved foam, viscosity, clarity and conditioning benefits in personal product compositions.

U.S. Pat. No. 5,037,973 to Meinetsbeger teaches a series of bis-alkyl aldonamide compounds as intermediates for pharmacological applications. While this paper does teach bis-alkyl aldonamide compounds containing heteroatoms, there is no teaching or suggestion that the use of such radicals will provide improved foam, viscosity, clarity and conditioning benefits in personal product compositions. In addition, the heteroatom containing alkyl aldonamides of this invention are monomeric in nature (structurally very different) whereas the bis-alkyl aldonamide compounds of U.S. Pat. No. 5,037,973 are dimeric in nature and would not be considered as useful ingredients in personal product compositions.

U.S. Pat. Nos. 3,766,367 and 3,855,290 to Zak, et al. as well as U.S. Pat. Nos. 4,038,294 and 4,342,706 to Conner, et al. teach quaternary halide gluconamide compounds of the formulas;

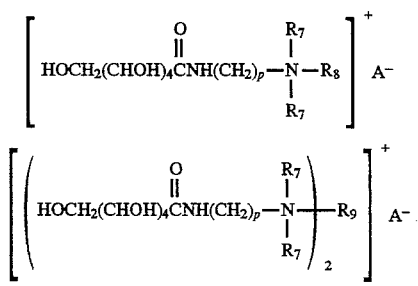

wherein;

$R_7=C_1-C_2$, $CH_2CH_2OH$

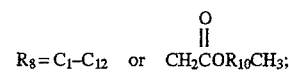

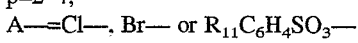
$q=1-3$;
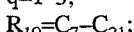
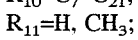

These compounds are said to be useful as emollients which are substantive to skin or hair and are further taught in U.S. Pat. Nos. 3,990,991 to Gerstein, 4,534,964 to Herstein et al. and 4,529,588 to Smith et al. which all describe conditioning shampoo compositions comprising quaternary halide gluconamide compounds. There is clearly no teaching or suggestion in any of these references, of using heteroatom containing alkyl aldonamide compounds of the invention in personal product compositions for improved foam, viscosity, clarity and conditioning benefits. Also the heteroatom containing alkyl aldonamide compounds of the present invention are structurally very different and do not contain a quaternary ammonium functional group which is responsible for the emolliency and conditioning effect.

Finally, there are several references teaching the molecular and liquid crystal structure of alkyl aldonamides, see for example, J. Am. Chem. Soc. 109(11):3387 (1987), 110:2861 (1988) and 112:1768 (1990) to Fuhrhop, et al.; Mol. Cryst. Liq. Cryst. 135:93 (1986) to Baeyens-Volant, et al., 185:209 (1990) to Jeffery and 198:381 (1991) to Van Doren, et al.; Chemistry and Physics of Lipids 39:313 (1986) to Zabel, et al.; Liquid Crystals 1(4):357 (1986) and Makrolmol. Chem. 189:2433 (1988) to Pfannemueller, et al.; Carbohydrate Research 176:165 (1988) to Fahrnow, et al. and J. Am Chem. Soc. 113:7436 (1991) to Frankel, et al.. There is clearly no teaching or suggestion in any of these references, of using heteroatom containing alkyl aldonamide compounds of the invention in personal product compositions for improved foam, viscosity, clarity and conditioning benefits.

Alkyl Aldobionamides

U.S. Pat. No. 2,752,334 to Walton and U.S. Pat. No. 2,785,152 to Jones teach aldobionamide compounds prepared by the reaction of aldobionic acids or aldobionolactones with fatty amines or fatty amino acid esters. The compounds are said to be useful as an emulsifier in food compositions and as antimycotic agents. There is no teaching or suggestion that the use of a heteroatom (e.g., oxygen, nitrogen or sulfur) in the aliphatic hydrocarbon radical of an alkyl aldobionamide compound can improve foam, viscosity, clarity and conditioning benefits in personal product compositions.

Williams, et al. in Archives of Biochem. and Biophysics, 195(1):145 (1979) and Carbohydrate Research 67:$C_1-C_3$ (1978) teach aldobionamide compounds prepared by the reaction of aldobionic acids with alkyl amines. Again, there is no teaching or suggestion that the alkyl group of the alkyl amine may contain a heteroatom, nor is there any teaching or suggestion of using heteroatom containing alkyl aldobionamide compounds for enhanced foam, viscosity, clarity and conditioning benefits in liquid personal product compositions.

Scholnick, et al. in J. Dairy Sci. 63(3):471 (1980) teach aldobionamide compounds as effective chelating agents of ferric ion. There is clearly no teaching or suggestion of using heteroatom containing alkyl aldobionamide compounds of the invention in personal product compositions for improved foam, viscosity, clarity and conditioning benefits.

In copending U.S. Ser. No. 816,419, the assignee of the subject application has filed an application directed to the use of the broad class of aldonamide surfactants in personal products or detergent compositions. The application, U.S. Ser. No. 981,644, has been filed as a separate application on the same date as U.S. Ser. No. 816,419. These applications have a few examples of using a heteroatom (i.e., ether and ester in the aliphatic hydrocarbon), however there is no teaching or suggestion that this heteroatom is responsible for improved foam, viscosity, clarity and conditioning characteristics in personal product compositions. Also, U.S. Ser. No. 981,644 has been filed as world application WO 94/12511. On page 17 of WO 94/12511 it is mentioned, along with a broad recital of multiple product types, that aldonamide compounds may be used as surfactants in personal product compositions. There is absolutely no exemplification or teaching of the heteroatom containing alkyl aldonamide compounds of the invention in compositions with for example, certain essential ingredients such as cosurfactants, skin conditioning agents, skin feel mildness agents, suspending agents, hydroxy acids, auxiliary thickening agents and auxiliary agents (see claim 4). There is also clearly no teaching of improved foam, viscosity, clarity and conditioning characteristics that are provided when heteroatom containing alkyl aldonamide compounds of the invention are formulated in personal product compositions. The individual ingredients have to fulfill, in part, wholly different functions while at the same time each ingredient must complement and increase the effect of other substances. This has always been a difficult challenge to meet and finding the right combination of ingredients for improved foam, viscosity, clarity and conditioning is a significant achievement.

Finally, there are several references teaching the molecular and micellar structure of alkyl aldobionamides generally, but are otherwise unrelated to the compounds of the invention, see for example, J. Phys. Chem. 9314):1482 (1989) and Colloid Poylm. Sci. 268(6).:513 (1990) to Denkinger, et al. and Polym. Bull. (Berlin) 6(5–6):305 (1982) to Emmerling. Since most personal product compositions are based on petrochemical ingredients, it would be most desirable to use materials which are instead naturally derived, such as carbohydrates. These renewable raw materials have the distinct advantage of being readily available, inexpensive, biodegradable, aquatically favorable and optically pure.

Thus the ability to find a naturally derived, environmentally friendly compound, that simultaneously provides an enhanced copious persistent lather, thick viscosity, clarity and conditioning effect in clear liquid personal product compositions is a significant achievement.

Accordingly, it is an object of the present invention to provide personal product compositions that have excellent lathering and foaming characteristics.

It is another object of the present invention to provide personal product compositions that have stiff consistencies which allow effective bottle and tube packaging.

It is another object of the present invention to provide viscous personal product compositions which are resist to spillage and effectively cling to the hand before cleansing.

It is another object of the present invention to provide stable clear personal product compositions comprising of a heteroatom containing alkyl aldonamide compound which do not become turbid or produce sedimentation upon standing.

It is still another object of the present invention to provide mild personal product compositions that efficiently remove surface grease and dirt from the skin.

It is still another object of the present invention to provide new and improved personal product compositions that leave the skin feeling fragrant, soft, smooth, silky and moisturized.

It is a final object of the present invention to provide an improved method of cleansing and conditioning the skin. These and other objects will become readily apparent from the detailed description which follows.

SUMMARY OF THE INVENTION

The present invention provides new personal product compositions for use in home cleansing and conditioning operations. The present invention is based on the discovery that heteroatom containing alkyl aldonamide compounds are useful as foam stabilizers, viscosity modifiers and conditioning agents in a variety of personal product compositions.

Included among the personal product compositions of the present invention are bubble baths, shower gels, facial cleansers or lotions, hand cleansers or lotions, body shampoos, syndet or toilet bars, shaving creams, deodorants or antiperspirants and the like. The components found in such compositions are described in the detailed description that follows.

DETAILED DESCRIPTION OF THE INVENTION

The present invention provides new personal product compositions that have improved foam, viscosity, clarity and conditioning characteristics due to the inclusion of a new type of alkyl aldonamide compound, specifically heteroatom containing alkyl aldonamide compounds of the formula:

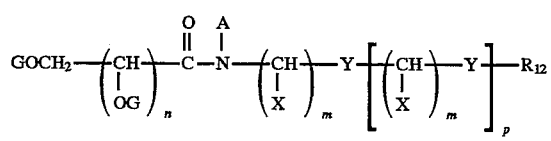

wherein:
n=1–6;
m=1–5;
X=H, a $C_1$–$C_4$ alkyl group or mixtures thereof;
Y=NA, $^+NH_2$, $^+NHA$, O, S, SO, $SO_2$,

or mixtures thereof;
p=0–25;
G=H, a mono-, di-, oligo-, polysaccharide group, a $(CH_2CH_2O)_q$-H, $(CH_2CHCH_3O)_r$-H group or mixtures thereof;
q=1–50;
r=1–50;
A=H, a hydroxy $C_1$–$C_{18}$ alkyl group, a $C_1$–$C_{18}$ straight or branched chain, saturated or unsaturated hydrocarbon which may be unsubstituted or substituted with an aromatic, cycloaliphatic, mixed aromatic aliphatic radical or a

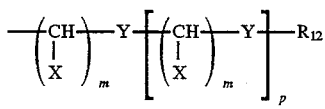

group or mixtures thereof; wherein X, m, Y and p are defined as above; and $R_{12}$ is a straight or branched chain, saturated or unsaturated hydrocarbon which may be unsubstituted or substituted with an aromatic, cycloaliphatic, or mixed aromatic aliphatic radical composing one or more carbon atoms, preferably from about 1 to about 28 carbon atoms. Preferably, n=2–5;
m=2–4;
X=H, a $C_1$ alkyl group or mixtures thereof;
Y=NA, $^+$NH$_2$, $^+$NHA, O,

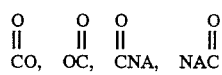

or mixtures thereof;
p=0–8;
G=H, a monosaccharide group, a $(CH_2CH_2O)_q$-H, $(CH_2CHCH_3O)_r$-H group or mixtures thereof;
q=1–25;
r=1–25;
A=H, a hydroxy $C_1$–$C_8$ alkyl group, a $C_1$–$C_8$ straight or branched chain, saturated or unsaturated hydrocarbon group or mixtures thereof; and $R_{12}$ is a straight or branched chain, saturated or unsaturated hydrocarbon which may be unsubstituted or substituted with an aromatic, cycloaliphatic, or mixed aromatic aliphatic radical comprising from about 7 to about 24 carbon atoms.
Most preferably,
n=3–5;
m=2–3;
X=H, a $C_1$ alkyl group or mixtures thereof;
Y=NA, $^+$NH$_2$, $^+$NHA, O,

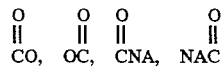

or mixtures thereof;
p=0–6;
G=H, a monosaccharide group, a $(CH_2CH_2O)_q$-H, $(CH_2CHCH_3O)_r$-H group or mixtures thereof;
q=1–15;
r=1–15;
A=H, a hydroxy $C_1$–$C_6$ alkyl group, a $C_1$–$C_6$ straight or branched chain, saturated or unsaturated hydrocarbon group or mixtures thereof; and $R_{12}$ is a straight or branched chain, saturated or unsaturated hydrocarbon radical comprising from about 8 to about 22 carbon atoms.

A specific example of a monosaccharide heteroatom containing alkyl aldonamide compound of the invention is $C_8/C_{10}$ oxypropyl D-gluconamide having the formula:

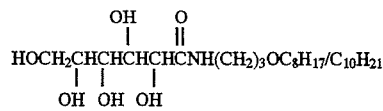

wherein:
n=4;
m=3;
X=hydrogen (H);
Y=oxygen (O);
p=0;
G=hydrogen;
A=hydrogen; and
$R_{12}=C_6H_{13}(1\%)$, $C_8H_{17}(59\%)$, $C_{10}H_{21}$ (39%), $C_{12}H_{25}$ (1%).

Another specific example of a monosaccharide heteroatom containing alkyl aldonamide compound of the invention is $C_{12}$–$C_{15}$ oxypropylaminopropyl D-glucoheptonamide having the formula:

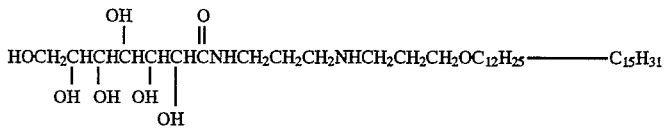

wherein:
n=5;
m=3;
X=hydrogen (H);
Y=oxygen (O) or nitrogen (NH);
p=1;
G=hydrogen;
A=hydrogen; and
$R_{12}=C_{12}H_{25}$ (25%), $C_{13}H_{27}$ (39%), $C_{14}H_{29}$ (21%), $C_{15}H_{31}$ (15%).

Yet another specific example of a monosaccharide heteroatom containing alkyl aldonamide compound of the invention is N-gluconyl dodecyldi(oxyethyl) glycinate, also known as N-gluconyl dodecyl(diethylene glycol) ether glycinate, N-gluconyl (diethylene glycol) monododecyl ether glycinate and as N-gluconyl dodecyl(dioxyethylene) glycinate having the formula:

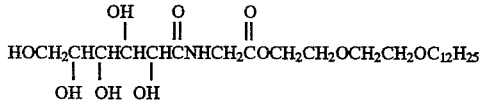

wherein:
n=4;
m=1 or 2;
X=hydrogen (H);
Y=ester (COO) or oxygen (O);
p=2;
G=hydrogen;
A=hydrogen; and
$R_{12}=C_{12}H_{25}$.

A specific example of a disaccharide heteroatom containing alkyl aldonamide compound of the invention is dodecyloxypropyl D-lactobionamide having the formula:

$HOCH_2CHCHCHCHCNH(CH_2)_3OC_{12}H_{25}$ (with OH, OH, OH, O substituents shown)

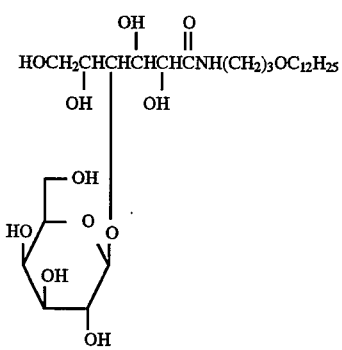

wherein:
n=4;
m=3;
X=hydrogen;
Y=oxygen (O);
p=0;
G=hydrogen or galactose;
A=hydrogen; and
$R_{12}=C_{12}H_{25}$.

Another specific example of a disaccharide heteroatom containing alkyl aldonamide compound of the invention is dodecyltri(oxyethyl)-oxypropyl D-glucopyranosyl-(1–5)-D-arabinonamide, also known as dodecyl (triethylene glycol) propylene glycol ether D-glucopyranosyl-(1–5)-D-arabinonamide, (triethylene glycol)propylene glycol monododecyl ether D-gluco-pyranosyl-(1–5)-D-arabinonamide and as dodecyl(trioxyethylene)oxypropylene D-glucopyranosyl-(1–5)-D-arabinonamide having the formula:

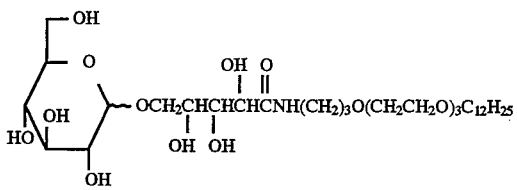

wherein:
n=3;
m=3 or 2;
X=hydrogen;
Y=oxygen (O);
p=3;
G=hydrogen or glucose;
A=hydrogen; and
$R_{12}=C_{12}H_{25}$.

D-Glucopyranosyl-(1–5)-D-arabinonic acid and its lactone are readily prepared from isomaltulose (also known as palatinose) by aqueous alkaline oxidation with oxygen or air [see DE-OS 3,248,404 (1982),. EP 114,954 (1983), U.S. Pat. No. 4,618,715 (1986) and Chem. Abstr. 102, 7034x (1985) to Lichtenthaler et al.], and isomaltulose is obtained commercially by biochemical dehydrogenation of sucrose with Agrobacterium Tumefaciens [see Zuckerind. 115:20 (1990) to Buchholz et al.].

Other examples of compounds of the invention are set forth below:
alkyloxymethyl D-gluconamide
alkyloxyethyl D-gluconamide
alkyloxybutyl D-gluconamide
alkyloxypentyl D-gluconamide
alkyloxyethyloxymethyl D-gluconamide
alkyldi(oxyethyl)oxymethyl D-gluconamide
alkyldi(oxyethyl) D-gluconamide
alkyltri(oxyethyl) D-gluconamide
alkyltetra(oxyethyl) D-gluconamide
alkylpenta(oxyethyl) D-gluconamide
alkylhexa(oxyethyl) D-gluconamide
alkylhepta(oxyethyl) D-gluconamide
alkylocta(oxyethyl) D-gluconamide
alkyldi(oxypropyl)oxyethyl D-gluconamide
alkyltri(oxypropyl)oxyethyl D-gluconamide
alkylocta(oxypropyl) oxyethyl D-gluconamide
alkyldi(oxyethyl)oxypropyl D-gluconamide
alkyltri(oxyethyl) oxypropyl D-gluconamide
alkyltetra(oxyethyl)oxypropyl D-gluconamide
alkylpenta(oxyethyl)oxypropyl D-gluconamide
alkylhexa(oxyethyl)oxypropyl D-gluconamide
alkylhepta(oxyethyl)oxypropyl D-gluconamide
alkylocta(oxyethyl)oxypropyl D-gluconamide
alkyloxymethyl D-lactobionamide
alkyloxyethyl D-lactobionamide
alkyloxybutyl D-lactobionamide
alkyloxypentyl D-lactobionamide
alkyl(oxyethyl)oxymethyl D-lactobionamide
alkyldi(oxyethyl)oxymethyl D-lactobionamide
alkyldi(oxyethyl) D-lactobionamide
alkyltri(oxyethyl) D-lactobionamide
alkyltetra(oxyethyl) D-lactobionamide
alkylpenta(oxyethyl) D-lactobionamide
alkylhexa(oxyethyl) D-lactobionamide
alkylhepta(oxyethyl) D-lactobionamide
alkylocta(oxyethyl) D-lactobionamide
alkyldi(oxypropyl)oxyethyl D-lactobionamide
alkyltri(oxypropyl)oxyethyl D-lactobionamide
alkylocta(oxypropyl)oxyethyl D-lactobionamide
alkyldi(oxyethyl)oxypropyl D-lactobionamide
alkyltri(oxyethyl)oxypropyl D-lactobionamide
alkyltetra(oxyethyl)oxypropyl D-lactobionamide
alkylpenta(oxyethyl)oxypropyl D-lactobionamide
alkylhexa(oxyethyl)oxypropyl D-lactobionamide
alkylhepta(oxyethyl) oxypropyl D-lactobionamide
alkylocta(oxyethyl)oxypropyl D-lactobionamide
alkyloxyethyl D-maltobionamide
alkyloxyethyloxymethyl D-maltobionamide
alkylhexa(oxyethyl) D-maltobionamide
alkyloxyethyl D-glucoheptonamide
alkyloxyethyl D-melibionamide
alkyloxyethyl D-cellobionamide
alkyloxyethyl D-gentiobionamide
alkyloxyethyl D-glucopyranosyl-(1–5)-D-arabinonamide
N-gluconyl alkyl(oxyethyl) glycinate
N-gluconyl alkyltri(oxyethyl) glycinate
N-gluconyl alkyltetra(oxyethyl) glycinate
N-gluconyl alkyltri(oxyethyl) N-methylglycinate
N-gluconyl dialkyldi(oxyethyl) aspartate
N-gluconyl alkyldi(oxyethyl) alaninate
N-gluconyl alkyltetra(oxyethyl) β-alaninate
N-gluconyl alkyldi(oxypropyl) N-methylalaninate N-gluconyl alkyltri(oxyethyl) α-aminobutyrate
N-gluconyl alkyl(oxyethyl) sarcosinate
N-gluconyl alkyldi(oxyethyl) sarcosinate
N-gluconyl alkyltri(oxyethyl) sarcosinate
N-gluconyl alkyltri(oxyethyl) leucinate
N-lactobionyl alkyldi(oxyethyl) glycinate
N-lactobionyl alkyltri(oxyethyl) alaninate
N-lactobionyl alkyltetra(oxyethyl) β-alaninate
N-lactobionyl alkyldi(oxyethyl) N-methylalaninate
N-lactobionyl alkyltri(oxyethyl) α-aminobutyrate
N-lactobionyl alkyltri(oxyethyl) α-aminoisobutyrate
N-lactobionyl alkyltri(oxyethyl) ε-aminocarproate
N-lactobionyl alkyldi(oxyethyl) sarcosinate
N-lactobionyl alkyltri(oxyethyl) leucinate
N-glucoheptonyl alkyl(oxyethyl) glycinate
N-maltobionyl alkyl(oxyethyl) glycinate
N-cellobionyl alkyl(oxyethyl) glycinate
alkyloxypropyl D-gluconamide monooxyethylene ether
alkyloxypropyl D-gluconamide dioxyethylene ether
alkyloxypropyl D-gluconamide trioxyethylene ether
alkyloxypropyl D-gluconamide tetraoxyethylene ether
alkyloxypropyl D-gluconamide pentaoxyethylene ether
alkyloxypropyl D-gluconamide hexaoxyethylene ether
alkyloxypropyl D-gluconamide heptaoxyethylene ether
alkyloxypropyl D-gluconamide octaoxyethylene ether
alkyloxypropyl D-gluconamide nonaoxyethylene ether
alkyloxypropyl D-gluconamide decaoxyethylene ether
alkyloxypropyl D-gluconamide trioxypropylene ether
alkyloxypropyl D-gluconamide oxyethylenedioxypropylene ether
alkyloxyethyl D-gluconamide dioxyethylenetrioxypropylene ether
alkyloxyethyl D-gluconamide trioxypropylenedioxyethylene ether
alkyloxypropyl D-lactobionamide monooxyethylene ether
alkyloxypropyl D-lactobionamide dioxyethylene ether
alkyloxypropyl D-lactobionamide trioxyethylene ether
alkyloxypropyl D-lactobionamide tetraoxyethylene ether
alkyloxypropyl D-maltobionamide dioxyethylene ether
alkyloxypropyl D-maltobionamide pentaoxypropylene ether
alkyloxypropyl D-maltobionamide decaoxypropylene ether Wherein the alkyl group contains from about 1 to about 28 carbon atoms, preferably from about 7 to about 24 carbon atoms and even more preferably from about 8 to about 22 carbon atoms.

The A group is preferably hydrogen, although it may be a hydroxy $C_1$–$C_4$ alkyl group or a $C_1$ to $C_{18}$ straight or branched chain, saturated or unsaturated hydrocarbon radical. The A group may also be interrupted by a heteroatom and may have the same structure as the group attached to the nitrogen atom.

If the A or $R_{12}$ group is an aliphatic radical, suitable examples include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, coco, soya, tallow, tall oil, castor, corn, cottonseed, palm, rapeseed, safflower, sesame, sunflower, fish oil, allyl, octenyl, nonenyl, decenyl, undecenyl, dodecenyl, tridecenyl, tetradecenyl, pentadecenyl, hexadecenyl, heptadecenyl, octadecenyl (oleyl), linoleyl and linolenyl.

If the A or $R_{12}$ group is interrupted by an aromatic radical, the aromatic group may be for example, benzyl or aniline. Cycloaliphatic radicals are exemplified but are not limited to cyclopentyl and cyclohexyl. Suitable mixed aromatic aliphatic radicals are exemplified by benzylpropyl, phenylethyl, phenoxyethyl and vinylbenzyl.

The G group may be hydrogen or an attached mono-, di-, oligo- or polysaccharide. Examples of suitable saccharides that can be oxidized to sugar acids $[GOCH_2(CHOG)_n COOH]$ include but are not limited to, erythrose, threose, ribose, arabinose, xylose, lyxose, allose, altrose, idose, talose, glucose, galactose, mannose, gulose, fructose, sorbose, sucrose, isomaltose, isomalt, isomaltulose (palatinose), trehalulose, 3-ketosucrose, leucrose, lactulose, gentiobiose, maltose, lactose, melibose, cellobiose, triglucose, tetraglucose, starch and cellulose.

When an amino group is present it may be converted to the corresponding salt by reaction with, for example an organic or inorganic acid such as hydrochloric acid, sulfuric acid, phosphoric acid, boric acid, oxalic acid, malonic acid, glutaric acid, adipic acid, sebacic acid, tricarballylic acid, butanetetracarboxylic acid, itaconic acid, maleic acid, malic acid, fumaric acid, citraconic acid, glutaconic acid, bis(hydroxymethyl)propionic acid, tartaric acid, citric acid, formic acid, lactic acid, acetic acid, benzoic acid, methanesulfonic acid, ethanesulfonic acid, toluenesulfonic acid and mixtures thereof or by reaction with, for example an alkylating agent such as chloromethane, dimethyl sulfate, diethyl sulfate and benzyl chloride.

The heteroatom containing alkyl aldonamide compounds of the present invention can also be ethoxylated, propoxylated or butoxylated with ethylene oxide, propylene oxide, butylene oxide or mixtures thereof to give a series of polyoxy ether sugar surfactants.

Typical levels of heteroatom containing alkyl aldonamide compound are from about 0.1% to about 45%, preferably from about 0.2% to about 40%, even more preferably from about 0.3% to about 35% by weight of the composition.

There are a wide variety of essential ingredients that can be used in personal product compositions depending on the characteristics and end purpose sought. Such ingredients are well known to those skilled in the art and include, but are not limited to cosurfactants, skin conditioning agents, skin feel mildness agents, suspending agents, hydroxy acids, auxiliary thickening agents, water and other optional ingredients (auxilary agents).

The individual ingredients have to fulfill, in part, wholly different functions while at the same time each ingredient must complement and increase the effect of other substances. This has always been a difficult challenge to meet and finding the right combination of ingredients for improved foam, viscosity, clarity and conditioning is a significant achievement.

COMPOSITIONS

The essential and optional ingredients of the present invention are given in the following paragraphs.

Cosurfactants (Cleansing Agents)

An essential component of the present invention is a cosurfactant. The term "cosurfactant" is used to denote both soap and nonsoap surface-active agents. The nonsoap surface-active agents include anionic, nonionic, amphoteric, zwitterionic and cationic surfactants.

Soaps

Suitable soaps are exemplified as alkali metal, ammonium m: alkanolammonium salts of aliphatic alkane or alkene monocarboxylic acids having about 8 to about 18 carbon atoms. Sodium, potassium, ammonium, mono-, di-, and triethanolammonium cations or combinations thereof, are preferred. Soaps may be prepared by either direct saponification of fats and oils or by neutralization of free fatty acids. Particularly useful are the sodium, potassium, ammonium and alkanolammonium salts of lauric acid, myristic acid, palmitic acid, stearic acid, oleic acid, linoleic acid, ricinoleic acid, coconut fatty acid, palm kernel fatty acid and tallow fatty acid.

Anionic Surfactants

Suitable anionic surfactants are broadly exemplified as alkali metal, ammonium or alkanolammonium salts of organic reaction products having an aliphatic alkyl, alkene or alkyl aromatic group with about 8 to about 18 carbon atoms and at least one water solubilizing radical selected from the, group consisting of phosphate, phosphonate, sulfonate, sulfate or carboxylate. Examples of suitable anionic surfactants useful in the present invention include the sodium, potassium, ammonium, mono-, di- and triethanolammonium salts of; $C_8$–$C_{18}$ alkyl phosphates, $C_8$–$C_{18}$ alkyl ether phosphates with about 1 to about 25 moles of alkylene oxide, $C_8$–$C_{18}$ acyl isethionates, $C_8$–$C_{18}$ acyl ether isethionates with about 1 to about 25 moles of alkylene ozide, $C_8$–$C_{18}$ acyl taurinates, $C_8$–$C_{18}$ acyl ether taurinates with about 1 to about 25 moles of alkylene oxide, $C_8$–$C_{18}$ alkyl benzene sulfonates, $C_8$–$C_{18}$ alkyl ether benzene sulfates with about 1 to about 25 moles of alkylene oxide, $C_8$–$C_{18}$ alkyl paraffin sulfonates (primary and secondary), $C_8$–$C_{18}$ alkanolamide sulfates, $C_8$–$C_{18}$ alkanolamide ether sulfates with about 1 to about 25 moles of alkylene oxide, $C_8$–$C_{18}$ alkyl α-sulfomonocarboxylates, $C_8$–$C_{18}$ is alkyl glyceryl sulfates, $C_8$–$C_{18}$ is alkyl glyceryl ether sulfates with about 1 to about 25 moles of alkylene oxide, $C_8$–$C_{18}$ alkyl glyceryl sulfonates, $C_8$–$C_{18}$ alkyl glyceryl ether sulfonates with about 1 to about 25 moles of alkylene oxide, $C_8$–$C_{18}$ alkyl ether methyl-carboxylates with about 1 to about 25 moles of alkylene oxide, $C_8$–$C_{18}$ alkyl sarcosinates/glycinates/hydrolysates, $C_8$–$C_{18}$ is monoalkyl sulfosuccinates, $C_8$–$C_{18}$ monoalkyl sulfosuccinamates, $C_5$–$C_{10}$ dialkyl sulfosuccinates, $C_5$–$C_{10}$ dialkyl sulfosuccinamates, $C_8$–$C_{18}$ α-olefin sulfonates, $C_8$–$C_{18}$ alkyl sulfates and $C_8$–$C_{18}$ alkyl ether sulfates with about 1 to about 25 moles of alkylene oxide.

Description of Anionic Surfactants

The sodium, potassium and ammonium salts of alkyl phosphates and alkyl ether phosphates having about 8 to about 18 carbon atoms and about 1 to about 25 moles of alkylene oxide represent a suitable class of anionic surfactant useful in the present invention. Alkyl phosphates and alkyl ether phosphates are prepared by reacting $C_8$–$C_{18}$ alkyl fatty alcohols, $C_8$–$C_{18}$ alkyl fatty alcohol alkoxylates or $C_8$–$C_{18}$ alkyl phenol alkoxylates with either phosphorous pentoxide, phosphorous oxychloride, phosphoric acid or polyphosphoric acid to give a mixture of monoalkyl and dialkyl phosphate esters that may be neutralized with base. Preferred alkyl ether phosphates are those comprising an average alkyl chain length of about 10 to about 16 carbon atoms and an average degree of alkoxylation of about 1 to about 16 moles of ethylene oxide propylene oxide or mixtures thereof. Specific examples of alkyl phosphate esters and alkyl ether phosphates useful in the present invention include sodium dodecyl phosphate, ammonium dodecyl phosphate, ammonium tetradecyl phosphate, sodium $C_{10}$–$C_{16}$ alkyl phosphate, sodium dodecyl(diethylene glycol) ether phosphate, sodium tetradecyl(triethylene glycol) ether phosphate, PPG-5 ceteth-10 phosphate, oleth-10 phosphate, potassium $C_9$–$C_{15}$ alkyl phosphate, triethanolamine lauryl phosphate, diethanolamine oleth-10 phosphate, diethanolamine cetyl phosphate and mixtures thereof.

The sodium, potassium and ammonium salts of alkyl isethionates, alkyl ether isethionates, alkyl taurinates and alkyl ether taurinates having about 8 to about 18 carbon atoms and about 1 to about 25 moles of alkylene oxide represent another suitable class of anionic surfactant useful in the present invention. Alkyl isethionates, alkyl ether isethionates, alkyl taurinates and alkyl ether taurinates are prepared by reacting $C_8$–$C_{18}$ alkyl fatty acids, $C_8$–$C_{18}$ alkyl fatty acid halides, $C_8$–$C_{18}$ alkyl ether $C_1$–$C_3$ alkylcarboxylic acids or $C_8$–$C_{18}$ alkyl ether $C_1$–$C_3$ alkylcarboxylic acid halides with either the sodium, potassium or ammonium salts of isethionate, polyoxyalkylene isethionate, taurine, polyoxyalkylene taurine, N-methyl taurine or polyoxyalkylene N-methyl taurine. Preferred alkyl ether isethionates and alkyl ether taurinates are those comprising an average alkyl chain length of about 10 to about 16 carbon atoms and an average degree of alkoxylation of about 1 to about 6 moles of ethylene oxide. Specific examples of alkyl isethionates, alkyl ether isethionates, alkyl taurinates and alkyl ether taurinates useful in the present invention include sodium dodecyl isethionate, potassium dodecyl isethionate, ammonium dodecyl isethionate, sodium tetradecyl isethionate, ammonium tetradecyl isethionate, sodium coconut isethionate, ammonium coconut isethionate, sodium dodecyl (ethylene glycol) ether isethionate, sodium coconut (diethylene glycol) ether isethionate, sodium dodecyl taurinate, sodium coconut(ethylene glycol) ether taurinate, sodium dodecyl N-methyl taurinate, ammonium dodecyl N-methyl taurinate, sodium tetradecyl N-methyl taurinate, sodium coconut N-methyl taurinate, ammonium coconut N-methyl taurinate, sodium tetradecyl(ethylene glycol) ether taurinate, ammonium coconut(triethylene glycol) ether N-methyl taurinate and mixtures thereof.

Another suitable class of anionic surfactant useful in the present invention are the sodium, potassium and ammonium salts of alkyl benzene sulfonates in which the alkyl group contains from about 8 to about 18 carbon atoms in branched or preferably in straight chain configuration. Alkyl benzene sulfonates are prepared by sulfonation of linear $C_8$–$C_{18}$ alkyl benzenes with sulfur trioxide in a falling film or tube bundle reactor followed by neutralization with base. Other suitable sulfonating agents used to prepare $C_8$–$C_{18}$ alkyl benzene sulfonates include oleum, chlorosulfonic acid, sulfuric acid or sulfur trioxide complexes. Examples of suitable alkali metal, ammonium and alkanolammonium salts of alkyl benzene sulfonates are disclosed in U.S. Pat. Nos. 2,220,099 and 2,477,383 both of which are incorporated herein by reference. Specific examples of alkyl benzene sulfonates useful in the present invention include sodium dodecyl benzene sulfonate, potassium dodecyl benzene sulfonate, ammonium dodecyl benzene sulfonate, sodium $C_{11}$–$C_{13}$ alkyl benzene sulfonate, sodium tetradecyl benzene sulfonate, ammonium tetradecyl benzene sulfonate and mixtures thereof.

Another suitable class of anionic surfactant useful in the present invention are the sodium, potassium and ammonium salts of alkyl benzene ether sulfates in which the alkyl group contains from about 8 to about 18 carbon atoms in branched or preferably in straight chain configuration with about 1 to about 25 moles of alkylene oxide. Alkyl benzene ether sulfates are prepared by sulfation of linear $C_8$–$C_{18}$ alkyl phenol alkoxylates with sulfur trioxide, oleum, chlorosulfonic acid, sulfuric acid or sulfur trioxide complexes followed by neutralization with base. Preferred alkyl benzene ether sulfates are those comprising an average alkyl chain length of about 10 to about 16 carbon atoms and an average degree of alkoxylation of about 1 to about 6 moles of ethylene oxide. Specific examples of alkyl benzene ether sulfates useful in the present invention include sodium nonylphenol(diethylene glycol) ether sulfate, sodium nonylphenol(triethylene glycol) ether sulfate, sodium dinonylphenol(triethylene glycol) ether sulfate, sodium dodecylphenol(tetraethylene glycol) ether sulfate, ammonium dodecylphenol(diethylene glycol) ether sulfate and mixtures thereof.

Still another suitable class of anionic surfactant useful in the present invention are the sodium, potassium and ammonium salts of paraffin sulfonates having about 8 to about 18 carbon atoms, more desirably from about 12 to about 16 carbon atoms. Paraffin sulfonates are preferably prepared by sulfoxidation of a specific cut of paraffin with sulfur dioxide and oxygen. The product consists mainly of secondary sulfonic acids along with some primary sulfonic acids which are neutralized with a suitable base to provide a water soluble paraffin sulfonate. Similarly, paraffin sulfonates may also be obtained by sulfochlorination which utilizes a mixture of sulfur dioxide, chlorine and actinic light as the sulfonating agent. It is most desirable to prepare paraffin sulfonates as the monosulfonate, having no unreacted starting paraffin hydrocarbon (or having a limited portion thereof present) and little or no inorganic salt by-product. Similarly the proportions of disulfonate or higher sulfonate should be minimized, although some may be present. Specific examples of paraffin sulfonate useful in the present invention include sodium $C_{12}$–$C_{13}$ paraffin sulfonate, sodium $C_{12}$–$C_{14}$ paraffin sulfonate, sodium $C_{12}$–$C_{15}$ paraffin sulfonate, sodium $C_{13}$–$C_{15}$ paraffin sulfonate potassium $C_{12}$–$C_{15}$ paraffin sulfonate, ammonium $C_{13}$–$C_{15}$ paraffin sulfonate, sodium $C_{12}$–$C_{16}$ paraffin sulfonate and mixtures thereof.

Still another suitable class of anionic surfactant useful in the present invention are the sodium, potassium and ammonium salts of alkanolamide sulfates and alkanolamide ether sulfates having about 8 to about 18 carbon atoms with about 1 to about 25 moles of alkylene oxide. Alkanolamide sulfates and alkanolamide ether sulfates are prepared by sulfating $C_8$–$C_{18}$ alkanolamides or $C_8$–$C_{18}$ alkanolamide alkoxylates with sulfur trioxide, oleum, chlorosulfonic acid, sulfuric acid or sulfur trioxide complexes followed by neutralization with base. Specific examples of alkanolamide sulfates and alkanolamide ether sulfates useful in the present invention include sodium dodecyl monoethanolamide sulfate, sodium tetradecyl diethanolamide monosulfate, sodium tetradecyl diethanolamide disulfate, sodium coconut monoethanolamide sulfate, ammonium coconut diethanolamide monosulfate, sodium coconut diethanolamide sesquisulfate, sodium coconut monoethanolamide (diethylene glycol) ether sulfate, sodium coconut monoethanolamide(triethylene glycol) ether sulfate and mixtures thereof.

Still another suitable class of anionic surfactant useful in the present invention are the sodium, potassium and ammonium salts of alkyl α-sulfomonocarboxylates having about 8 to about 18 carbon atoms. Alkyl α-sulfomonocarboxylates are prepared by sulfonation of $C_8$–$C_{18}$ alkyl fatty acids, $C_8$–$C_{18}$ alkyl fatty acid esters with sulfur trioxide, oleum, chlorosulfonic acid, sulfuric acid or sulfur trioxide complexes followed by neutralization with base; or by esterification of sulfoacetic acid, α-sulfopropionic acid or α-sulfobutyric acid with higher $C_8$–$C_{18}$ alkyl alcohols followed by neutralization with base. Specific examples of alkyl α-sulfomonocarboxylates useful in the present invention include sodium methyl α-sulfolaurate, potassium ethyl α-sulfolaurate, sodium methyl α-sulfomyristate, ammonium ethyl α-sulfomyristate, sodium decyl α-sulfobutyrate, sodium dodecyl sulfoacetate, sodium coconut sulfoacetate, ammonium dodecyl α-sulfopropionate and mixtures thereof.

Still another suitable class of anionic surfactant useful in the present invention are the sodium, potassium and ammonium salts of alkyl glyceryl sulfates and alkyl glyceryl ether sulfates having about 8 to about 18 carbon atoms and about 1 to about 25 moles of alkylene oxide. Alkyl glyceryl sulfates and alkyl glyceryl ether sulfates are prepared by sulfation of $C_8$–$C_{18}$ alkyl monoglycerides, $C_5$–$C_{14}$ dialkyl glycerides, $C_8$–$C_{18}$ alkyl monoglyceride alkoxylates, fats or oils with sulfuric acid. Suitable examples of fats and oils include coconut, soya, tallow, castor, corn, cottonseed, palm, rapeseed, safflower, sesame, sunflower, fish, and tall oil. Preferred alkyl glyceryl ether sulfates are those comprising an average chain length of about 10 to about 16 carbon atoms and an average degree of alkoxylation of about 1 to about 6 moles of ethylene oxide. Specific examples of alkyl glyceryl sulfates useful in the present invention include sodium dodecyl glyceryl sulfate, potassium dodecyl glyceryl sulfate, ammonium dodecyl glyceryl sulfate, sodium tetradecyl glyceryl sulfate, ammonium oleyl glyceryl sulfate, ammonium tetradecyl glyceryl sulfate, sodium coconut glyceryl sulfate, sodium coconut(ethylene glycol) glyceryl ether sulfate, sodium coconut-(diethylene glycol) glyceryl ether sulfate, sodium coconut(triethylene glycol) glyceryl ether sulfate and mixtures thereof.

Still another suitable class of anionic surfactant useful in the present invention are the sodium, potassium and ammonium salts of alkyl glyceryl sulfonates and alkyl glyceryl ether sulfonates having about 8 to about 18 carbon atoms and about 1 to about 25 moles of alkylene oxide. Alkyl glyceryl sulfonates and alkyl glyceryl ether sulfonates are prepared by the Strecker reaction of a higher $C_8$–$C_{18}$ alkyl chlorohydrin ether or $C_8$–$C_{18}$ alkyl polyoxyalkylene chlorohydrin ether with alkali sulfite, alkali bisulfite or analogous type salt. Preferred alkyl glyceryl sulfonates are those comprising an average chain length of about 10 to about 16 carbon atoms and an average degree of alkoxylation of about 1 to about 6 moles of ethylene oxide. Specific examples of alkyl glyceryl sulfonates useful in the present invention include sodium dodecyl glyceryl sulfonate, potassium dodecyl glyceryl sulfonate, ammonium dodecyl glyceryl sulfonate, sodium tetradecyl glyceryl sulfonate, ammonium oleyl glyceryl sulfonate, ammonium tetradecyl glyceryl sulfonate, sodium coconut glyceryl sulfonate, sodium coconut(ethylene glycol) glyceryl ether sulfonate, sodium coconut(diethylene glycol) glyceryl ether sulfonate, sodium coconut(triethylene glycol) glyceryl ether sulfonate and mixtures thereof.

Still another suitable class of anionic surfactant useful in the present invention are the sodium, potassium and ammonium salts of alkyl ether methylcarboxylates having about 8 to about 18 carbon atoms and about 1 to about 25 moles of alkylene oxide. Alkyl ether methylcarboxylates are prepared by carboxymethylating the condensation products of alkylene oxide and higher $C_8$–$C_{18}$ alkyl alcohols with halo-acetic acid salts or by chemical oxidation. The alcohols can be derived synthetically or naturally from fats or oils. Dodecyl alcohol, tetradecyl alcohol and coconut oil are preferred herein. Such alcohols are reacted with about 1 to about 25 moles of alkylene oxide followed by carboxymethylation and neutralization with base. Preferred alkyl ether methylcarboxylates are those comprising an average alkyl chain length of about 10 to about 16 carbon atoms and an average degree of alkoxylation of about 1 to about 15 moles of ethylene oxide, propylene oxide or mixtures thereof. Specific examples of alkyl ether methylcarboxylates useful in the present invention include sodium dodecyl ether methylcarboxylate, sodium dodecyl(ethylene glycol) ether methylcarboxylate, sodium dodecyl(diethylene glycol) ether methylcarboxylate, ammonium dodecyl(triethylene glycol) ether methylcarboxylate, sodium tetradecyl(triethylene glycol) ether methylcarboxylate, sodium tetradecyl-(tetraethylene glycol) ether methylcarboxylate, trideceth-7 carboxylate, laureth-13 carboxylate and mixtures thereof.

Still another suitable class of anionic surfactant useful in the present invention are the sodium, potassium, ammonium and alkanolammonium salts of alkyl sarcosinates having about 8 to about 18 carbon atoms. Alkyl sarcosinates are generally considered to be acylated amino acid salts prepared by amidation of $C_8$–$C_{18}$ alkyl fatty acids, $C_8$–$C_{18}$ alkyl fatty acid esters or $C_8$–$C_{18}$ alkyl fatty acid halides with an amino acid sarcosine salt. Specific examples of alkyl sarcosinates useful in the present invention include sodium dodecyl sarcosinate, potassium dodecyl sarcosinate, ammonium dodecyl sarcosinate, sodium tetradecyl sarcosinate, ammonium tetradecyl sarcosinate, sodium coconut sarcosinate, ammonium coconut sarcosinate triethanolamine oleyl sarcosinate and mixtures thereof. Examples of other suitable acylated amino acid salts useful in the present invention include the sodium, potassium and ammonium salts of $C_8$–$C_{18}$ alkyl alaninate, $C_8$–$C_{18}$ alkyl β-alaninate, $C_8$–$C_{18}$ alkyl N-methyl alaninate, $C_8$–$C_{18}$ alkyl α-aminoisobutyrate, $C_8$–$C_{18}$ alkyl α-aminobutyrate, $C_8$–$C_{18}$ alkyl α-aminocaproicate, $C_8$–$C_{18}$ alkyl glycinate, $C_8$–$C_{18}$ alkyl N-ethyl glycinate, $C_8$–$C_{18}$ alkyl N-propyl glycinate, $C_8$–$C_{18}$ alkyl N-butyl glycinate, $C_8$–$C_{18}$ alkyl leucinate, $C_8$–$C_{18}$ alkyl methioninate, $C_8$–$C_{18}$ alkyl serinate, $C_8$–$C_{18}$ alkyl dl-norvalinate, $C_8$–$C_{18}$ alkyl aspartate, $C_8$–$C_{18}$ alkyl glutamate and mixtures thereof. Preferred acylated amino acid salts useful in the present invention include the sodium, potassium and ammonium salts of dodecyl, tetradecyl and coconut glycinate, sarcosinate and mixtures thereof. Besides amidating amino acids salts, mixtures of amino acids or polypeptides, obtained by hydrolyzing proteins, may be amidated with $C_8$–$C_{18}$ alkyl fatty acids, $C_8$–$C_{18}$ alkyl fatty acid esters or $C_8$–$C_{18}$ alkyl fatty acid halides. Suitable examples of hydrolyzable proteins include collagen, corn, keratin, silk, soy, scrapleather, wheat gluten and albumin. Preferred polypeptide amino acid salts useful in the present invention include the sodium, potassium and ammonium salts of dodecyl, tetradecyl, coconut and oleyl leather hydrolysate or collagen hydrolysate (animal protein).

Yet another suitable class of anionic surfactant useful in the present invention are the sodium, potassium and ammonium salts of alkyl or dialkyl sulfosuccinates and sulfosuccinamates having from about 8 to about 18 carbon atoms. Alkyl sulfosuccinates and sulfosuccinamates are prepared by the reaction of maleic anhydride, maleic and/or fumaric acid with one or two equivalents of an appropriate reactive moiety containing a labile hydrogen, followed by sulfonation with sodium bisulfite, sodium sulfite, sodium metabisulfite or analogous type salt. Suitable examples of appropriate labile reactants are the $C_8$–$C_{18}$ alkyl fatty amines, $C_8$–$C_{18}$ alkyl fatty alcohols, $C_8$–$C_{18}$ alkyl fatty alcohol alkoxylates, $C_8$–$C_{18}$ alkyl fatty amides, $C_8$–$C_{18}$ alkyl fatty alkanolamides and $C_8$–$C_{18}$ alkyl fatty alkanolamide alkoxylates. Preferred are the alkyl sulfosuccinates, particularly sodium dioctyl sulfosuccinate, disodium dodecyl sulfosuccinate, diammonium tetradecyl sulfosuccinate, disodium dodecyl(diethylene glycol) ether sulfosuccinate, disodium coconut (triethylene glycol) ether sulfosuccinate, disodium undecylenamido MEA sulfosuccinate, disodium laurethsulfosuccinate, disodium lauramido MEA sulfosuccinate, disodium cocoamidosulfosuccinate, disodium cocoamido MIPA sulfosuccinate, disodium oleamido MEA sulfosuccinate, disodium oleamido PEG-2 Sulfosuccinate, disodium oleamidosulfosuccinate, disodium cocoamido(tetraethylene glycol) ether sulfosuccinate, disodium ricinoleylamido MEA sulfosuccinate, disodium cocoamido MEA sulfosuccinate and mixtures thereof.

Yet another suitable class of anionic surfactant useful in the present invention are the sodium, potassium and ammonium salts of α-olefin sulfonates having about 8 to about 18 carbon atoms. α-Olefin sulfonates are prepared by continuous sulfonation of 1-alkenes with liquid or gaseous sulfur trioxide. The 1-alkenes are derived from oligomerization of ethylene or from thermocracking of certain hydrocarbons. Suitable examples of 1-alkenes include 1-dodecene, 1-tetradecene and 1-hexadecene. The sulfonation of 1-alkenes results in a fairly complex mixture of products comprised of alkene sulfonate, hydroxyalkane sulfonate and alkyl disulfonate in a ratio of about (60–70):(20–30):(4–12) respectively. Preferred α-olefin sulfonates are those comprising a mixture of individual compounds having an average chain length of about 12 to about 16 carbon atoms. Such mixtures can comprise from about 0% to about 30% by weight $C_{12}$ olefin sulfonate, from about 55% to about 75% by weight $C_{14}$ olefin sulfonate and from about 25% to about 45% by weight $C_{16}$ olefin sulfonate. Specific examples of α-olefin sulfonates useful in the present invention include sodium $C_{12}$–$C_{13}$ α-olefin sulfonate, sodium $C_{12}$–$C_{14}$ α-olefin sulfonate, sodium $C_{13}$–$C_{14}$ α-olefin sulfonate, sodium $C_{13}$–$C_{15}$ olefin sulfonate, sodium $C_{12}$–$C_{16}$ α-olefin sulfonate, potassium $C_{12}$–$C_{16}$ α-olefin sulfonate, ammonium $C_{12}$–$C_{16}$ α-olefin sulfonate and mixtures thereof. Further examples of α-olefin sulfonates are described more fully in U.S. Pat. No. 3,332,880 which is incorporated herein by reference.

A preferred class of anionic surfactant found to be useful in the present invention are the sodium, potassium and ammonium salts of alkyl sulfates, especially those obtained by sulfating higher $C_8$–$C_{18}$ alkyl alcohols produced naturally from coconut oil or those prepared synthetically from petroleum sources. Specific examples of alkyl sulfates useful in the present invention include sodium dodecyl sulfate, potassium dodecyl sulfate, ammonium dodecyl sulfate, monoethanolammonium dodecyl sulfate, diethanolammonium dodecyl sulfate, triethanolammonium dodecyl sulfate, sodium tetradecyl sulfate, potassium tetradecyl sulfate, ammonium tetradecyl sulfate, monoethanolammonium tetradecyl sulfate, triethanolammonium tetradecyl sulfate, sodium hexadecyl sulfate, ammonium hexadecyl sulfate, sodium coconut sulfate, sodium $C_{12}$–$C_{15}$ alkyl sulfate and mixtures thereof. Alkyl sulfates are sold commercially under several trade names which includes Carsonol ALS and Carsonol DLS, Carsonol SLS and Carsonol sold by Lonza Inc.; Duponol QC, Duponol D Paste, Duponol EP, Duponol G, Duponol LS Paste and Duponol WA Paste sold by Witco Corporation; Rhodapon CAV, Rhodapon L22, Rhodapon LSB, Rhodapon LT-6 and Rhodapon TDS sold by Rhone-Poulenc; Standpol A and Standpol DEA sold by Henkel Corporation; Sulfochem ALS, Sulfochem DLS, Sulfochem TLS and Sulfochem SLS sold by Chemron.

Another preferred class of anionic surfactant found to be most useful in the present invention are the sodium, potassium and ammonium salts of alkyl ether sulfates which are obtained by sulfating the higher $C_8$–$C_{18}$ alcohol ethoxylates. Such alcohols are reacted with about 1 to about 25 moles of alkylene oxide followed by sulfation and neutralization with base. Most highly preferred alkyl ether sulfates useful in the present invention include those comprising a mixture of individual compounds having an average chain length of about 10 to about 18 carbon atoms and an average degree of alkoxylation of about 1 to about 4 moles of ethylene oxide. Such a mixture can comprise from about 0% to about 50% by weight $C_{10}$–$C_{11}$ alkyl ether sulfate, from about 20% to about 100% by weight $C_{12}$ alkyl ether sulfate, from about 0% to about 80% by weight $C_{13}$–$C_{14}$–$C_{15}$–$C_{16}$ alkyl ether sulfates and from about 0% to about 30% by weight $C_{17}$–$C_{18}$ alkyl ether sulfates; and from about 5% to about 90% by weight of compounds having a degree of alkoxylation of 0; from about 7% to about 95% by weight of compounds having a degree of alkoxylation of 1 to 4; and from about 0% to about 35% by weight of compounds having a degree of alkoxylation greater than 5. Specific examples of alkyl ether sulfates useful in the present invention include sodium laureth-1 sulfate, sodium laureth-2 sulfate, sodium laureth-3 sulfate, potassium laureth-1 sulfate, potassium laureth-2 sulfate, potassium laureth-3 sulfate, ammonium laureth-1 sulfate, ammonium laureth-2 sulfate, ammonium laureth-3 sulfate, monoethanolammonium laureth-1 sulfate, monoethanolammonium laureth-2 sulfate, monoethanolammonium laureth-3 sulfate, diethanolammonium laureth-1 sulfate, diethanolammonium laureth-2 sulfate, diethanolammonium laureth-3 sulfate, triethanolammonium laureth-1 sulfate, triethanolammonium laureth-2 sulfate, triethanolammonium laureth-3 sulfate, sodium myreth-1 sulfate, sodium myreth-2 sulfate, sodium myreth-3 sulfate, ammonium myreth-1 sulfate, ammonium myreth-2 sulfate, ammonium myreth-3 sulfate, sodium $C_{10}$–$C_{16}$ alkyl (1) ether sulfate, sodium $C_{10}$–$C_{16}$ alkyl (2) ether sulfate, sodium $C_{10}$–$C_{16}$ alkyl (3) ether sulfate and mixtures thereof. Alkyl ether sulfates are sold commercially under several trade names which includes Carson SLES-2 and Carson SES-A sold by Lonza Inc.; Duponol FAS sold by Witco Corporation; Norfox SLES-03 and Norfox SLES-60 sold by Norman, Fox & Co.; Standpol EA-1, Standpol EA-2, Standpol EA-3, Standpol EA-40, Standpol ES-1, Standpol ES-2, Standpol ES-3, Standpol ES-40, Standpol ES-50, Standpol ES-250 and Standpol 350 sold by Henkel Corporation; Sulfochem EA-1, Sulfochem EA-2, Sulfochem EA-3, Sulfochem EA-60, Sulfochem EA-70, Sulfochem ES-i, Sulfochem ES-2, Sulfochem ES-3, Sulfochem ES-60, Sulfochem ES-70 and Sulfochem K sold by Chemron.

Nonionic Surfactants

Suitable commercial nonionic surfactants are broadly exemplified as the polyoxyalkylene oxide condensation products of hydrophobic alkyl, alkene, or alkyl aromatic functional groups having a free reactive hydrogen available for condensation with hydrophilic alkylene oxide, such as ethylene oxide, propylene oxide, butylene oxide, polyethylene oxide or polyethylene glycol to form nonionic surfactants. Examples of such hydrophobic functional groups include hydroxy, carboxy, mercapto, amino or amido groups.

The overall reaction may be expressed as:

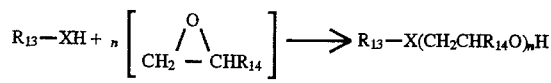

wherein $R_{13}$ is a hydrophobic alkene or alkane group having about 8 to about 18 carbon atoms; $R_{14}$ is hydrogen or an alkyl group with about 1 to about 2 carbon atoms; n is from about 1 to about 100; X is selected from the group consisting of O, $C_6H_4O$, $C_6H_3R_{13}O$, COO, S, NH, $NR_{15}$, CONH, $CONR_{15}$, $CONR_{15}(CH_2)_a(NR_{15})_2$ and $CONR_{15}(CH_2)_b NR_{15}(CH_2)_c N(R_{15})_2$; where $R_{15}$ is selected from the group consisting of H, $(CH_2CH_2O)_d$, $(CH_2CHCH_3O)_e$ and mixtures thereof; a+b+c is from about 1 to about 10; and d+e is from about 1 to about 200.

Examples of useful hydrophobes of commercial nonionic surfactants include higher $C_8$–$C_{18}$ alkyl fatty alcohols, middle $C_8$–$C_{14}$ alkylphenols, higher $C_8$–$C_{18}$ alkyl fatty acids, higher $C_8$–$C_{18}$ alkyl mercaptans, higher $C_8$–$C_{18}$ alkyl fatty amines, higher $C_8$–$C_{18}$ alkyl amides and higher $C_8$–$C_{18}$ alkyl fatty alkanolamides. The polyoxyalkylene oxide condensate products of such materials may comprise from about 1 to about 100 moles of alkylene oxide, preferably from about 2 to about 60 moles of alkylene oxide, even more preferably from about 3 to about 25 moles alkylene oxide.

Description of Nonionic Surfactants

The polyoxyalkylene esters of alkyl fatty acids, the polyoxyalkylene alkyl mercaptans, the polyoxyalkylene alkyl fatty amides and the polyoxyalkylene alkyl fatty alkanolamides having an average alkyl chain length of about 8 to about 18 carbon atoms and from about 3 to about 25 moles of ethylene oxide represent a suitable class of nonionic surfactant useful in the present invention. Specific examples of such surfactants useful in the present invention include polyoxyethylene (8) lauryl mercaptan, polyoxyethylene (6) lauryl ester, polyoxyethylene (8) lauryl ester, polyoxyethylene (8) myristyl ester, polyoxyethylene (10) myristyl ester, polyoxyethylene (14) myristyl ester, polyoxyethylene (15) coconut ester, polyoxyethylene (7) laurylamide, polyoxyethylene (10) laurylamide, polyoxyethylene (20) laurylamide, polyoxyethylene (16) myristylamide, polyoxyethylene (12) cocoamide, polyoxyethylene (20) cocodiethanolamide and mixtures thereof.

Another suitable class of nonionic surfactant useful in the present invention are the polyoxyalkylene oxide block copolymers such as those obtained by the condensation of hydrophilic ethylene oxide with hydrophobic polyoxypropylene glycol. The hydrophobic portion of these compounds preferably has a molecular weight of about 1500 to about 1800 and exhibits water insolubility. The addition of polyoxyethylene units to this hydrophobic portion tends to increase the water solubility of the molecule as a whole as well as the liquid character of the product. Preferred surfactancy is retained up to the point where the polyoxyethylene content is from about 10% to about 50% by weight of the total condensation product. This corresponds to condensation of about 4 moles to about 40 moles ethylene oxide. Specific examples of commercially available polyoxyalkylene oxide block copolymers useful in the present invention include Pluronic L61, Pluronic L62, Pluronic L62D, Pluronic L62LF, Pluronic L63, Pluronic L64, Pluronic P65, and Pluronic F68 sold by BASF wherein the prefixes L, P and F before the numbers represent liquid, paste or flake form respectively. (Pluronic L62D is a low foaming version of Pluronic L62 and Pluronic L62LF is a mixture of 10% Pluronic L61 and 90% Pluronic L62).

Another suitable class of nonionic surfactant useful in the present invention are the polyoxyalkylene oxide block copolymers such as those obtained by the condensation of hydrophilic ethylene oxide with hydrophobic polyoxypropylene ethylenediamine or polyoxypropylene triethylenetetramine The hydrophobic portion of these compounds preferably has a molecular weight of about 2500 to about 4500 and exhibits water insolubility. The addition of polyoxyethylene units to this hydrophobic portion tends to increase the water solubility of the molecule as a whole as well as the liquid character of the product. Preferred surfactancy is retained up to the point where the polyoxyethylene content is from about 20% to about 90% by weight of the total condensation product. Specific examples of commercially available polyoxyethylene-polyoxypropylene ethylenediamines useful in the present invention includes Tetronic 702, Tetronic 704 and Tetronic 804 sold by BASF having the formula:

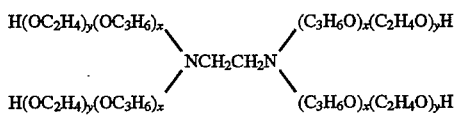

wherein x is from about 43 to about 78 of a polyoxypropylene group, which corresponds to an average molecular weight of about 2500 to about 4500; and y is from about 14 to about 920 of a polyoxyethylene group, which corresponds to an average molecular weight of about 625 to about 40,500 or about 20% to about 90% by weight of the total product.

Still another suitable class of nonionic surfactant useful in the present invention are the alkylmonoglycosides and alkylpolyglycosides as those disclosed in U.S. Pat. No. 4,565,647 having the formula $R_{16}O(C_nH_{2n}O)_x(\text{glycosyl})_y$ wherein $R_{16}$ is selected from the group consisting of alkyl, alkene, alkylphenyl, hydroxyalkyl, hydroxyalkylphenyl and mixtures thereof containing from about 8 to about 18 carbon atoms; preferably containing from about 10 to about 16 carbon atoms; n is 2 or 3, preferably n is 2; x is from about 0 to about 15, preferably x is 0; and y is from about 1 to about 8, preferably y is from about 1.1 to about 5, most preferably y is from about 1.2 to about 2.5. The glycosyl group may be derived from glucose, galactose, lactose, maltose, sucrose, starch, cellulose, fructose and mixtures thereof; preferably, however, the glycosyl is derived from high dextrose corn syrup, glucose or starch. Alkylpolyglycosides are prepared by the reaction of $C_8$–$C_{18}$ alkyl alcohols or $C_8$–$C_{18}$ alkylpolyoxyalkylene alcohols with glucose or a source of glucose at the anomeric position (carbon 1 hydroxyl group position) to form a glycoside. Additional glycosyl units can then be attached to the 2, 3, 4, and/or 6 hydroxyl group position of the newly formed glycoside to produce an alkylpolyglycoside. Optionally and less desirably the alkylpolyglycoside may be alkoxylated with alkylene oxide to form a polyoxyalkylene alkylpolyglycoside with about 8 to about 18 carbon atoms and about 1 to about 100 moles of ethylene oxide, preferably from about 2 to about 7 moles of ethylene oxide. Specific examples of alkylmonoglycosides useful in the present invention include dodecyl glucoside, tetradecyl glucoside and coconut glucoside. Specific examples of alkylpolyglycosides useful in the present invention include dodecyl polyglucoside with a degree of polymerization of 1.2, dodecyl polyglucoside with a degree of polymerization of 1.3, dodecyl polyglucoside with a degree of polymerization of 1.5, tetradecyl polyglucoside with a degree of polymerization of 1.2, tetradecyl polyglucoside with a degree of polymerization of 1.4, tetradecyl polyglucoside with a degree of polymerization of 1.6, coconut polyglucoside with a degree of polymerization of 1.2, $C_{10}$–$C_{16}$ alkyl polyglucoside with a degree of polymerization of 1.2, $C_{10}$–$C_{16}$ alkyl polyglucoside with a degree of polymerization of 1.4, coconut polyglucoside with a degree of polymerization of 1.3, coconut polyglucoside with a degree of polymerization of 1.5, coconut polyglucoside with a degree of polymerization of 2.1 and mixtures thereof.

Still another suitable class of nonionic surfactant useful in the present invention are the alkene oxide condensation products of polyhydroxyalkyl esters having about 8 to about 18 carbon atoms and about 1 to about 200 moles of ethylene or propylene oxide, preferably from about 3 to about 45 moles of ethylene or propylene oxide. Examples of polyhydroxyalkyl esters include those having about 2 to about 7 hydroxyl groups per alkyl chain such as ethylene glycol esters, propylene glycol esters, glycerol esters, polyglycerol esters, erythritol esters, xylitol esters, pentaerythritol esters, sorbitol/sorbitan esters, mannitol/mannitan esters, alkyl glucoside esters, glucose esters and sucrose esters. Specific examples include, but are not limited to PEG-12 glyceryl laurate, PEG-7 glyceryl cocoate, PEG-30 glyceryl cocoate, PEG-25 glyceryl oleate, PEG-200 glyceryl tallowate, PEG-200 glyceryl palmirate, PEG-4 glyceryl caprylate/caprate, PEG-8 glyceryl caprylate/caprate, PEG-55 propylene glycol oleate, PEG-55 propylene glycol oleate, sucrose stearate, sucrose distearate and the like.

Preferred polyhydroxypolyoxyalkylene alkyl esters useful in the present invention include the polyoxyalkylene sorbitan, and mannitan esters having about 8 to about 18 carbon atoms and about 3 to about 100 moles of ethylene oxide. Specific examples of polyoxyalkylene sorbitan and mannitan esters include the Tweens, such as polyoxyethylene (10) sorbitan monolaurate, polyoxyethylene (20) sorbitan monolaurate, polyoxyethylene (44) sorbitan monolaurate, polyoxyethylene (20) monopalmitate, polyoxyethylene (20) sorbitan monostearate, polyoxyethylene (10) sorbitan monococoate, polyoxyethylene (20) sorbitan monococoate, polyoxyethylene (30) marmitan dilaurate, polysorbate 20, polysorbate 21, polysorbate 60, polysorbate 61, polysorbate 65, polysorbate 80, polysorbate 85 and mixtures thereof.

Still another suitable class of nonionic surfactant useful in the present invention are the amine oxides of the formula:

$R_{17}(OR_{18})_x(R_{19})_2N\rightarrow O$ wherein $R_{17}$ is alkyl, alkene, hydroxyalkyl, acylamidopropyl and alkylphenyl group or mixtures thereof, containing about 8 to about 18 carbon atoms, preferably from about 10 to about 18 carbon atoms; $R_{18}$ is an alkylene or hydroxyalkylene group containing from about 2 to about 3 carbon atoms, preferably 2 carbon atoms; x is from about 0 to about 3, preferably x is 0; and each $R_{19}$ is an alkyl or hydroxyalkyl group containing from about 1 to about 3 carbon atoms, preferably from about 1 to about 2 carbon atoms, or a polyoxyethylene group having about 1 to about 3 moles of ethylene oxide, preferably from about 1 mole of ethylene oxide. The $R_{19}$ group can also be attached to each other e.g., through an oxygen or nitrogen atom to form a ring structure. Specific examples of amine oxides useful in the present invention include dimethyloctylamine oxide, diethyldecylamine oxide, dimethyldodecylamine oxide, diethyldodecylamine oxide, dimethyltetradecylamine oxide, dimethyl Alfol 1214 amine oxide, methylethylhexadecylamine oxide, diethyloctadecylamine oxide, dimethylcocoamine oxide, dimethyl-2-hydroxydodecylamine oxide, bis(2-hydroxyethyl)dodecylamine oxide, bis(2-hydroxyethyl)

cocoamine oxide, bis(2-hydroxyethyl) oleylamine oxide, bis(2-hydroxyethyl) $C_{12}$–$C_{15}$ alkoxypropylamine oxide, dimethyldodecyloxyethylamine oxide, dodecylamidopropyldimethylamine oxide, tetradecylamidopropyldimethylamine oxide, cocoamidopropyldimethylamine oxide and mixtures thereof. Preferred amine oxide are the $C_{10}$–$C_{18}$ alkyldimethylamine oxides and the $C_{10}$–$C_{18}$ acylamidoalkyldimethylamine oxides.

Still another suitable class of nonionic surfactant useful in the present invention are the polyhydroxy fatty acid amides of the formula:

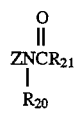

wherein $R_{20}$ is H, a $C_1$–$C_4$ alkyl, 2-hydroxyethyl, 2-hydroxypropyl group or mixtures thereof, preferably $R_{20}$ is methyl; and $R_{21}$ is a straight or branched chain $C_5$–$C_{31}$ alkyl, alkenyl, alkylphenyl, hydroxyalkyl, hydroxyalkylphenyl group, preferably a straight chain $C_9$–$C_{17}$ alkyl or alkene group; and Z is a polyhydroxy group containing at least 2 hydroxyl groups or an alkoxylated derivative thereof (preferably an ethoxylated or propoxylated derivative). Z may be derived from a reducing sugar in a reductive amination reaction and is preferably a glycityl. Examples of suitable reducing sugars include glucose, fructose, sucrose, maltose, lactose, galactose, mannose, xylose, starch and cellulose. As for commercial raw materials, high dextrose corn syrup, high fructose corn syrup and high maltose corn syrup can be utilized and may be preferred in some cases over the individual sugar components. Z may be selected from the group consisting of $HOCH_2(CHOH)_nCH_2$- or $HOCH_2(CHOH)CHOR_{22}$-$(CHOH)_2CH_2$— where n is an integer from about 2 to about 6, inclusive, and $R_{22}$ is H or a cyclic or aliphatic monosaccharide. Most preferred are glycityls wherein n is 4, particularly $HOCH_2(CHOH)_4CH_2$-. Examples of $R_{20}$ include N-methyl, N-ethyl, N-propyl, N-isopropyl, N-butyl, N-2-hydroxyethyl and N-2-hydroxypropyl. Examples of >$NCOR_{21}$ include lauramide, myristamide, palmitamide, stearamide, oleamide, cocoamide and tallowamide. Examples of Z include .1-deoxyglucityl, 2-deoxyfructityl, 1-deoxymaltityl, 1-deoxylactityl, 1-deoxygalactityl, 1-deoxymannityl and 1-deoxymaltotriotityl. Optionally the polyhydroxy fatty acid amide may be alkoxylated with alkylene oxide to form a polyoxyalkylene polyhydroxy fatty acid amide with about 8 to about 18 carbon atoms and about 1 to about 100 moles of ethylene oxide, preferably from about 2 to about 7 moles of ethylene oxide. Methods for making polyhydroxy fatty acid amides are known in the art. In general, they are prepared by the reaction of an alkyl amine with a reducing sugar followed by reductive amination to form the corresponding N-alkyl polyhydroxyamine, which is then reacted with a fatty aliphatic ester or triglyceride in a condensation/amidation step to form the final N-alkyl N-polyhydroxy fatty acid amide product. Processes for making polyhydroxy fatty acid amides are disclosed in for example, U.S. Pat. No. 1,985,424 to Piggott, U.S. Pat. No. 2,703,798 to Schwartz and U.S. Pat. No. 2,965,576 to Wilson all of which are incorporated herein by reference.

Yet another suitable class of nonionic surfactant useful in the present invention are the non-heteroatom containing alkyl aldonamides and aldobionamides having about 8 to about 18 carbon atoms. Alkyl aldonamides and aldobionamides are prepared by the reaction of an aldonic acid, aldobionic acid, aldonolactone or aldobionolactone with a non-heteroatom containing alkyl amine such as decylamine, dodecylamine, tetradecylamine, hexadecylamine, octadecylamine, oleylamine and cocoamine in an organic solvent. Specific examples of alkyl aldonamides and aldobionamides useful in the present invention include dodecyl gluconamide, tetradecyl gluconamide, coco gluconamide, coco glucoheptonamide, decyl lactobionamide, dodecyl lactobionamide, tetradecyl lactobionamide, hexadecyl lactobionamide, octadecyl lactobionamide, oleyl lactobionamide, coco lactobionamide, coco maltobionamide and mixtures thereof.

Yet another suitable class of nonionic surfactant useful in the present invention are the alkyl glycoside esters having the formula:

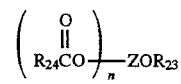

wherein $R_{23}$ is H, a $C_1$–$C_6$ alkyl, hydroxyethyl or hydroxypropyl group; preferably $R_{23}$ is methyl or ethyl; n is from about 1 to about 3; $R_{24}$ is a straight or branched chain alkyl, alkene, alkylphenyl, hydroxyalkyl, hydroxyalkylphenyl group having about 7 to about 17 carbon atoms and $ZOR_{23}$ is a polyhydroxy sugar group derived from the glycosidation of reducing sugars. Examples of suitable reducing sugars include glucose, fructose, sucrose, maltose, lactose, galactose, mannose, xylose, starch and cellulose. As for commercial raw materials, high dextrose corn syrup, high fructose corn syrup and high maltose corn syrup can be utilized and may be preferred in some cases over the individual sugar components. Examples of $ZOR_{23}$ include glucose, methyl glucoside, ethyl glucoside, hydroxyethyl glucoside, methyl galactoside, methyl fructoside, ethyl fructoside, methyl lactoside and ethyl sucroside. Alkyl glycoside esters are prepared by enzymatic esterification of $C_8$–$C_{18}$ fatty acids or by alkaline transesterification of $C_8$–$C_{18}$ fatty acid esters/triglycerides with alkyl glycosides such as methyl or ethyl glucoside at elevated temperature. The alkyl glycoside esters may also be ethoxylated or propoxylated with about 1 to about 150 moles of ethylene oxide, propylene oxide or mixtures thereof. Specific examples of alkyl glycoside esters useful in the present invention include methyl glucoside monococoate, ethyl glucoside monolaurate, ethyl glucoside monomyristrate, ethyl glucoside monococoate, ethyl glucose sesquicocoate, ethyl glucose dicocoate, methyl fructoside monococoate, methyl lactoside monococoate, methyl sucroside monococoate, sucrose cocoate, methyl gluceth-20 sesquistearate, PEG-120 methyl glucose dioleate, methyl gluceth-10, methyl gluceth-20, PPG-20 methyl glucose ether and mixtures thereof.

A preferred class of nonionic surfactant found to be useful in the present invention are the polyoxyalkylene alkyl alcohols having about 8 to about 18 carbon atoms in either branched or preferably straight chain configuration and about 1 to about 100 moles of ethylene oxide. Particularly preferred are the condensation products of alcohols having an alkyl group containing about 10 to about 16 carbon atoms with from about 3 to about 40 moles of ethylene oxide per mole of alcohol. Specific examples of commercially available nonionic surfactants of this type include Tergitol 15-S-9 (the condensation product of $C_{11}$–$C_{15}$ linear secondary alcohol with 9 moles of ethylene oxide and a narrow molecular weight distribution) and Tergitol 24-L-6 NMW (the condensation product of $C_{12}$–$C_{14}$ primary alcohol with 6 moles of ethylene oxide) both sold by Union Carbide Corporation;

Neodol 45-7 (the condensation product of $C_{14}$–$C_{15}$ linear alcohol with 7 moles of ethylene oxide), Neodol 45-9 (the condensation product of $C_{14}$–$C_{15}$ linear alcohol with 9 moles of ethylene oxide), Neodol 23-6.5 (the condensation product of $C_{12}$–$C_{13}$ linear alcohol with 6.5 moles of ethylene oxide), Neodol 45-4 (the condensation product of $C_{14}$–$C_{15}$ linear alcohol with 4 moles of ethylene oxide), Neodol 25-7 (the condensation product of $C_{12}$–$C_{15}$ linear alcohol with 7 moles of ethylene oxide and Neodol 25-9 (the condensation product of $C_{12}$–$C_{15}$ linear alcohol with 9 moles of ethylene oxide) all sold by Shell Chemical Company. The CTFA adopted name for this class of nonionic surfactant is laureth-x (PEG-x lauryl ether), isolaureth-x (PEG-x isolauryl ether), myreth-x (PEG-x myristyl ether), ceteth-x (PEG-x cetyl ether), steareth-x (PEG-x stearyl ether), oleth-x (PEG-x oleyl ether), cetoleth-x (PEG-x cetyl/oleyl ether) and ceteareth-x (PEG-x cethyl/stearyl ether) wherein x is about 1 to about 100 and represents the degree of ethoxylation. Preferred are laureth-4 through 25, myreth-4 through 10, ceteth-5 through 30 and stearth-3 through 40. The polyoxyalkylene alkyl alcohols having about 4 to about 18 carbon atoms in either branched or preferably straight chain configuration and about 1 to about 100 moles of propylene oxide are useful as well. Particularly preferred are the condensation products of alcohols having an alkyl group containing about 10 to about 16 carbon atoms with from about 3 to about 40 moles of propylene oxide per mole of alcohol. Specific examples of commercially available nonionic surfactants of this type include PPG-y butyl ether, PPG-y decyl ether, PPG-y lauryl ether, PPG-y isolauryl ether, PPG-y myristyl ether, PPG-y cetyl ether, PPG-y stearyl ether, PPG-y oleyl ether, PPG-y cetyl/oleyl ether and PPG-y cethyl/stearyl ether wherein y is about 1 to about 100 and represents the degree of propoxylation.

Yet, another class of nonionic surfactant found to be useful in the present invention are the polyoxyalkylene alkylphenols having about 8 to about 14 carbon atoms in either branched or preferably straight chain configuration and about 1 to about 100 moles of ethylene oxide, preferably from about 5 to about 23 moles of ethylene oxide. Specific examples of commercially available nonionic surfactants of this type include Igepal CO-610 (the condensation product of nonylphenol with about 7 to about 8.5 moles of ethylene oxide), Igepal CO-630 (the condensation product of nonylphenol with 9 moles of ethylene oxide), Igepal RC-620 (the condensation product of dodecylphenol with about 10 moles of ethylene oxide, Igepal RC-630 (the condensation product of dodecylphenol with about 12 moles of ethylene oxide), Igepal DM-710 (the condensation product of dinonylphenol with about 15 moles of ethylene oxide) all sold by GAF Corporation and Triton X-114 (the condensation product of octylphenol with about 7 to about 8 moles of ethylene oxide), Triton X-100 (the condensation product of octylphenol with about 9 to about 10 moles of ethylene oxide) and Triton X-102 (the condensation product of octylphenol with about 12 to about 13 moles of ethylene oxide) all sold by Rohm & Haas Company. The CTFA adopted name for this class of nonionic surfactant is octoxynol, nonoxynol and dodoxynol. Preferred are octoxynol-5 through 20, nonoxynol-5 through 23 and dodoxynol-5 through 12.

Amphoteric Surfactants

There are two classes of amphoteric surfactant; those that are pH sensitive (amphoteric) and those that are pH insensitive (zwitterionic).

Suitable amphoteric surfactants are exemplified as those which can be broadly classified as derivatives of aliphatic secondary and tertiary amines which contain a quaternary ammonium or non-quaternary ammonium group and one long chained alkyl or alkene group having about 8 to about 18 carbon atoms and at least water solubilizing radical selected from the group consisting of sulfates, sulfonates, carboxylates, phosphates or phosphonates.

Examples of such amphoteric surfactants include the N-alkyl β-amino propionates, such as sodium(dodecyl β-amino)propionate (sodium lauraminopropionate), diethanolamine lauraminopropionate and sodium cocoaminopropionate; the N-alkyl β-imino dipropionates, such as disodium-(dodecyl β-imino)dipropionate (sodium lauriminodipropionate) and cocoiminodipropionate; the alkyl taurinates, such as monoethanolammonium coconut taurinate as taught in U.S. Pat. No. 2,658,072 which is incorporated herein by reference and the derivatives derived from 2-alkyl-2-imidazoline, such as those sold under the trade name Miranol as taught in U.S. Pat. Nos. 2,528,378, 2,773,068, 2,781,354 and 2,781,357 all of which are incorporated herein by reference. The amphoteric imidazoline derived surfactants are a preferred class of amphoteric surfactant and are prepared by condensing aminoethylethanolamine, diethylenetriamine or ethylenediamine with a fatty acid having about 8 to about 18 carbon atoms to form a five-membered imidazoline ring which may be ionized by an anionizable alkylating agent such as sodium chloroacetate, methyl or ethyl acrylate, acrylic acid, 2-hydroxy- 1,3-propane sultone, 3-chloro-2-hydroxypropane sulfonic acid and 1,3-propane sultone on or near the cyclic portion or cationic portion of the molecule. Alkylations may be done with or without solvent or in aqueous solution. In aqueous solution, the imidazoline ring may be hydrolytically opened to form a mixture of imidazoline and linear amide. Specific examples of amphoteric imidazoline-derived surfactants useful in the present invention include lauroamphocarboxypropionate, lauroamphopropionate, lauroamphoglycinate, lauroamphocarboxyglycinate, lauroamphopropylsulfonate, lauroamphocarboxypropionic acid, myristoamphocarboxypropionate, myristoamphopropionate, myristoamphoglycinate, myristoamphocarboxyglycinate, myristoamphopropylsulfonate, myristoamphocarboxypropionic acid, cocoamphocarboxypropionate, cocoamphopropionate, cocoamphoglycinate, cocoamphocarboxyglycinate, cocoamphopropylsulfonate, cocoamphocarboxypropionic acid and mixtures thereof. The CTFA adopted name for this class of amphoteric surfactant is amphoteric-1 through 20. Preferred are amphoteric-1, 2, 6, 10, 12, 17, 18, 19, 20 and mixtures thereof.

Zwitterionic Surfactants

Suitable zwitterionic surfactants are exemplified as those which can be broadly described as derivatives of aliphatic quaternary ammonium, sulfonium and phosphonium compounds with one long chain group having about 8 to about 18 carbon atoms and at least one water solubilizing radical selected from the group consisting of sulfate, sulfonate, carboxylate, phosphate or phosphonate. A general formula for these compounds is:

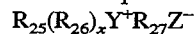

wherein $R_{25}$ contains an alkyl, alkene or hydroxyalkyl group with about 8 to about 18 carbon atoms, from about 0 to about 10 moles of ethylene oxide and from about 0 to about 2 glyceryl units; Y is a nitrogen, sulfur or phosphorous atom; $R_{26}$ is an alkyl or hydroxyalkyl group with about 1 to about 3 carbon atoms; x is i when Y is a sulfur atom and 2 when Y is a nitrogen or phosphorous atom; $R_{27}$ is an alkyl or hydroxyalkyl group with about 1 to about 5 carbon atoms and Z is radical selected from the group consisting of sulfate, sulfonate, carboxylate, phosphate or phosphonate. Examples of such zwitterionic surfactants include the sulfatobetaines, such as 3-(dodecyldimethylammonio)-1-propane sulfate and 2-(cocodimethyl-ammonio)-1-ethane sulfate, soyaamidopropylethyldimonium ethosulfate; the sulfobetaines, such as 3-(dodecyldimethylammonio)-2-hydroxy-1-propane sulfonate, 3-(tetradecyldimethylammonio)-1-propane sulfonate, 3-($C_{12}$–$C_{14}$ alkylamidopropyldimethylammonio) -2-hydroxy-1-propane sulfonate, 3-(cocodimethylammonio) -1-propane sulfonate; the carboxybetaines such as (dodecyldimethylammonio)acetate (lauryl betaine), (tetradecyldimethylammonio)acetate (myristyl betaine), (cocodimethylammonio)acetate (coconut betaine), (oleyldimethylammonio)acetate (oleyl betaine), (dodecyloxymethyldimethylammonio)acetate, (tetradecyloxyhydroxylpropyldimethylammonio)acetate, [cocodi(polyethoxyethanol) ammonio] acetate, (dodecyldimethylammonio)propionate, (dodecylamidopropyldimethylammonio)acetate, (cocoamidopropyldimethylammonio)acetate (also known as cocoamidopropyl betaine); the sulfoniobetaines such as (dodecyldimethylsulfonio)acetate and 3-(cocodimethylsulfonio)-1-propane sulfonate and the phosphoniobetaines such as 4-(trimethylphosphonio)-1-hexadecane sulfonate, 3-(dodecyldimethylphosphonio)-1-propane sulfonate, 2-dodecyldimethylphosphonio)-1-ethane sulfite, myristamidopropyldimethylamine phosphate and mixtures thereof.

Means for preparing many of the surfactant compounds of this class are described in U.S. Pat. Nos. 2,129,264, 2,697,656, 2,774,786, 2,813,898, 2,828,332, 3,265,719, 3,529,521 and German Pat. No. 1,018,421 all of which are incorporated herein by reference.

Of all the above described types of zwitterionic surfactants, preferred compounds include the sulfobetaines such as 3-(cocodimethylammonio)-1-propanesulfonate, 3-(cocodimethylammonio)-2-hydroxy-1-propanesulfonate and the carboxybetaines such as (cocodimethylammonio) acetate, (dodecyl-amidopropylammonio)acetate and (cocoamidopropylammonio)acetate, (cocoamidopropyl betaine).

Cationic Surfactants

Cationic surfactants have been taught in the art as conditioning agents for the skin. Suitable cationic surfactants are broadly exemplified as those of the general formula:

$[R_{28}R_{29}N^+R_{30}R_{31}]A^-$ wherein $R_{28}$ contains an alkyl, alkene or alkylphenyl group with about 10 to about 24 carbon atoms; $R_{29}$, $R_{30}$ and $R_{31}$ contains an alkyl, alkene or alkylphenyl group with about 10 to about 24 carbon atoms, or an alkyl or alkylhydroxy group with about 1 to about 5 carbon atoms; and A- can be any salt forming anion such as halide, hydroxide, sulfate, carbonate and phosphate.

Examples of such cationic surfactants include myristyltrimethyl ammonium chloride, cetyltrimethylammonium chloride, stearyltrimethylammonium chloride, oleyltrimethylammonium chloride, tallowtrimethylammonium chloride, dimyristyldimethylammonium chloride, dicetyldimethylammonium chloride, distearyldimethylammonium chloride, distearyldiethylammonium bromide, dioleyldimethylammonium chloride, ditallowdimethylammonium chloride, stearyldimethylbenzyl ammonium chloride (stearalkonium chloride), PPG-9 diethylmonium chloride, PPG-25 diethylmonium chloride, PPG-40 diethylmonium chloride, trimyristylmethyl ammonium chloride, tricetylmethylammonium chloride, tristearylmethylammonium chloride, bishydroxyethyl dihydroxypropyl steraminium chloride, gaur hydroxypropyltrimonium chloride, benzyl trimethylammonium hydrolyzed animal protein, stearamidopropyl PG dimonium chloride, stearamidopropyl PG dimonium phosphate, panthenyl hydroxypropyl steardimonium chloride or mixtures thereof. The CTFA adopted name for this class of cationic surfactant is quaternium. Preferred cationic surfactants are quaternium-1 through 84, most preferably quaternium-6, quaternium- 15, quaternium- 19, quaternium-20, quaternium-22, quaternium-23, quaternium-26, quaternium-32, quaternium-33, quaternium-41, quaternium-60 and quaternium-70. The polymeric cationic surfactants such as polyquaternium-1 through 39 are useful as well, preferably polyquaternium-4, polyquaternium-7, polyquaternium-8, polyquaternium-10, polyquaternium- 11 and polyquaternium-24.

Many additional non-soap surfactants are described in McCutcheon's Detergents and Emulsifiers (Vol. 1) and McCutcheon's Functional Materials (Vol. 2), 1992 Annual, published by MC Publishing Co. as well as the CTFA (Cosmetic, Toiletry and Fragrance Association) 1992 International Buyers Guide, published by CTFA Publications and OPD 1993 Chemical Buyers Directory 80th Annual Edition, published by Schnell Publishing Co. which are all incorporated herein by reference.

The above mentioned cosurfactants (anionic, nonionic, amphoteric, zwitterionic, cationic surfactant and mixtures thereof) are used in combination with the heteroatom containing alkyl aldonamides in personal product compositions of the present invention. The anionic surfactants, particularly the alkyl sulfates, the alkyl ether sulfates and the alkyl isethionates, the nonionic surfactants, particularly the alkyl polyoxyalkylene sorbitan esters and the alkyl polyglycosides, and the amphoteric surfactants particularly, the alkyl carboxybetaines are preferred for use herein.

Typical levels of cosurfactant are from about 0% to about 50%, preferably from about 0.1% to about 45%, even more preferably from about 0.2% to about 40% by weight of the composition.

Skin Conditioning Agents (Moisturizers/Emollients)

Various materials have been taught in the art for use as agents that condition the skin. In general, such conditioning agents are designed to make the skin feel soft, smooth, silky and moisturized.

The term moisturizer is often used synonymously with the term emollient, and is meant to describe a material which imparts a soft, smooth, silky and moisturized feeling to the skin surface.

One way of moisturizing is to reduce the rate of water loss from the stratum corneum (skin surface) by depositing an occlusive material (emollient or emulsifier) on the skin surface which prevents water evaporation. Mother technique is to add hygroscopic nonocclusive substances (humectants), which will retain water to the stratum corneum, making water available to the skin surface thereby producing the desired cosmetic effect. Nonocclusive moisturizers also function by improving the lubricity of the skin. Both occlusive and nonocclusive moisterizers as well as mixtures thereof are operative in the present invention. Examples of occulusive moisturizers, (emollients or emulsifiers) include, lanolin and its derivatives, long chain esters, waxes, saturated and unsaturated fatty alcohols, conditioning oils and extracts, phospholipids, sterols, ceramides and silicones.

Examples nonocculusive moisturizers (humectants) include polyols, fatty acids, certain alkanolamides, pyrrolidone carboxylic acid and their derivatives. It is to be understood that any such skin conditioning agent or mixtures thereof can be employed herein, depending on the formulations desires.

Examples of lanolin derivatives useful in the present invention include, but are not limited to lanolin, lanolin oil, lanolin fatty acid, sodium lanolate, potassium lanolate, ammonium lanolate, monoethanolamine lanolate, diethanolamine lanolate, triethanolamine lanolate, lanolin alcohol, acetylated lanolin, acetylated lanolin alcohol, ethoxylated lanolin such as PEG-75 lanolin, propoxylated/ethoxylated lanolin oil such as PPG-12/PEG-65 lanolin oil, ethoxylated sorbitol lanolin, propoxylated lanolin, ethoxylated lanolin alcohol, lanolin alcohol ricinoleate, lanolin alcohol linoleate, acetate of lanolin alcohol ricinoleate, hydrogenated lanolin, ethoxylated hydrogenated lanolin and the like.

Examples of long chain esters useful in the present invention include, but are not limited to cetyl acetate, stearyl acetate, oleyl acetate, lauryl lactate, myristyl lactate, cetyl lactate, stearyl lactate, decyl neopentanoate, myristyl propionate, decyl oleate, isopropyl myristate, lauryl myristate, myristyl myristate, myreth-3-myristate, palmityl myristate, stearyl myristate, isopropyl palmirate, octyl palmitate, 2-ethylhexyl palmirate, lauryl palmitate, myristyl palmirate, palmityl palmitate, stearyl palmirate, butyl stearate, myristyl stearate, palmityl stearate, isocetyl stearate, isostearyl isostearate, oleyl myristate, oleyl stearate, oleyl oleate, methyl cocoate, isopropyl cocoate, butyl cocoate, cetearyl octanoate; butyloxyethyl stearate, isopropyl lanolate, cetyl octanoate, coconut caprate/caprylate, hydroxyoctacosanyl hydroxystearate, cetyl ricinoleate, decyl oleate, butyl oleate, octyl/lauryl myristate, PPG-2 myristyl ether propionate, PPG-10 butanediol, PPG-8-$C_{12}$–$C_{20}$ alkyl ester, Peg-45 palm kernel glyceride, neopentylglycol dicaprylate/dicaprate, $C_{12}$–$C_{15}$ alcohol benzoate, diisoarachidyl dilinoleate, dioctyl maleate, ascorbyl palmitate, diisopropyl adipate, diisohexyl adipate, dihexadecyl adipate, diisopropyl sebacate, dioctyl succinate, didecyl succinate, jojoba esters and the like.

Examples of waxes useful in the present invention include, but are not limited to beeswax, white beeswax, polyoxyethylene sorbitol beeswax, paraffin wax, ceresin wax, lanolin wax, polyethylene wax, microcrystalline wax, spermaceti, carnauba wax, candelilla wax, wool wax alcohols, petroleum wax, ozokerite wax, glyceride wax, castor wax, emulsifying wax polydecene and the like.

Examples of saturated and unsaturated fatty alcohols useful in the present invention include, but are not limited to carbitol, lauryl alcohol, myristyl alcohol, cetyl alcohol, isocetyl alcohol, stearyl alcohol, isostearyl alcohol, hydroxystearyl alcohol, oleyl alcohol, ricinoleyl alcohol, behenyl alcohol, erucyl alcohol, 2-octyldodecanyl alcohol, cetearyl alcohol, lanolin alcohol and the like.

Examples of conditioning emollient oils useful in the present invention include arnica blossom oil, apricot kernel oil, avocado oil, babassa oil, balm mint oil, basil oil, bergamot oil, bitter almond oil, bitter orange oil, castor oil, calendula oil, coconut oil, collagen/lanolin oil, cod liver oil, cucumber oil, corn oil, carrot oil, egg oil, eucalyptus oil, evening primrose oil, geranium oil, gardenia oil, grapefruit oil, grape seed oil, hybrid safflower oil, jasmine oil, jojoba oil, kiwi oil, light mineral oil, lemon oil, mandarin orange oil, orange flower oil, orange oil, mink oil, olive oil, palm oil, peach kernel oil, passionflower oil, rapeseed oil, sesame oil, soybean oil, safflower oil, sunflower oil, sweet almond oil, vegetable oil, wheat germ oil, petrolatum, squalene, squalane, ozokerite, hydrogenated castor oil, hydrogenated sunflower seed oil, hydrogenated peanut oil, hybrid sunflower seed oil, borage oil, PEG-40 hydrogenated castor oil and the like.

Examples of conditioning extracts useful in the present invention include aloe extract, aloe flower extract, aloe vera gel extract, apple extract, apple leaf extract, apple pectin extract, balsam canada extract, balsam oregon extract, balsam peru extract, balsam tolu extract, balm mint extract, black walnut extract, birch leaf extract, birch sap extract, calendula extract, chamomile extract, colocynth extract, comfrey extract, comfrey leaf extract, coltsfoot extract, clover blossom extract, custard apple extract, egg extract, fennel extract, gelatin extract, geranium extract, grapefruit extract, horsetail extract, henna extract, hazel extract, hops extract, honey extract, indian cress extract, kelp extract, lemon extract, lemon juice extract, lemon peel extract, lime extract, malt extract, mandarin orange extract, matricaria extract, mint extract, nettle extract, oakmoss extract, orange extract, orange peel extract, ponkan extract, papaya extract, pummelo extract, red raspberry extract, red raspberry leaf extract, rhubarb extract, rosemary extract, thyme extract, tamarind extract, tangerine extract, sage extract, strawberry extract, strawberry leaf extract, valerian extract, witch hazel extract, autolyzed yeast extract, yarrow extract, thistle extract, passion fruit extract, ivy extract, seaweed extract, aqua hamamelis and the like.

Suitable phospholipids are exemplified as complex fat soluble substances that contain in their molecule, in addition to fatty acids and glycerol, a nitrgenous base such as choline or ethanolamine, two long alkyl chains having about 10 to about 18 carbon atoms and phosphoric acid. These compounds are found universally in living cells and are either completely absent or present in low concentrations in surface lipids. Specific examples of phospholipids useful in the present invention include, but are not limited to lecithin, cephalin (phosphatidylethanolamine), phosphatidylinositol and the like.

Examples of sterols useful in the present invention include, but are not limited to cholesterol, ethoxylated cholesterol, propoxylated cholesterol, cholesteryl acetate, cholesteryl benzoate, cholesteryl heptanoate, cholesteryl octanoate, cholesteryl nonanoate, cholesteryl palmirate, cholesteryl stearate, cholesteryl oleate, cholesteryl linoleate, cholesteryl oleyl carbonate, cholesteryl hydrocinnamate, cholesteryl chloride, 7-dehydrocholesterol, lumisterol, tachysterol, pyrocalciferol, lanosterol, lathosterol, ergosterol, stigmasterol, sitosterol, asterosterol, PEG-25 soya sterol and the like.

Examples of ceramides (sphingolipides) useful in the present invention are those disclosed in EP Application Nos. 0,556,957, 0,227,994, 0,282,816 and 0,097,059, JP-A-63-192,703, U.S. Pat. Nos. 4,778,823, 4,985,546, 5,175,321, 5,198,210 and 5,206,020 and J. Soc. Cosmet. Chem. 40, 273–285 (1989) all of which are incorporated herein by reference. Both natural ceramides and synthetic pseudoceramides can be used, however the synthetic pseudoceramides are preferred because they are relatively cheaper to produce. Examples of ceramides or pseudoceramides that are useful in the present invention include, but are not limited to ceramide 1, ceramide 2, ceramide 3, ceramide 4, ceramide 5, ceramide 6, ceramide 7, lactosyl ceramide, ceramide trihexoside (globotriosyl ceramide), globoside (globotetraosyl ceramide), sphingomyelin, psychosine (ceramide galactoside), kerasin (ceramide galactoside with an amidated fatty acid), phrenosin (ceramide galactoside with an amidated 2-hydroxy fatty acid), bovine sulfatide (ceramide galactoside 3-sulfate with an amidated fatty acid), glucocerebrosides (ceramide glucoside), gangliotetraosyl ceramide, monosialoganglioside, disialoganglioside, trisialoganglioside, N-(2-hydroxyoctadecyl)-N-(2-hydroxyethyl)-2-hydroxyhexadecamide, N-(2-hydroxyoctadecyl)-N-(2-O-glucopyranosyl)ethyl-2-hydroxyhexadecamide, N-(2-hydroxyoctadecyl)-N-(2-hydroxyethyl)-2-hydroxy-ω-O-linoleoyldocosamide, N-(2-hydroxyoctadecyl)-N-(2-hydroxyethyl)-2-hydroxy-ω-O-linoleoylhexadecamide, N-(2,3-di-hydroxyoctadecyl)-N-(2-hydoxyethyl)-2-hydroxyhexadecamide, N-(2,3-di-hydroxyoctadecyl)-N-(2-hydroxyethyl)-2-hydroxy-ω-O-linoleoyldocosamide, N-(2-hydroxyoctadecyl)-N-(2-sulphoethyl)-2-hydroxyhexadecamide, N-(2-hydroxyoctadecyl)-N-(2-phosphoethyl)-2-hydroxyhexadecamide, N-(2,3 -dihydroxypropyl) -N-dodecyl hexadecanamide, N-(2,3-dihydroxypropyl) -N-tetradecyl hexadecanamide, N-(2,3-dihydroxypropyl)-N-hexadecyl hexadecanamide, N-(2,3-dihydroxypropyl)-N-octadecyl hexadecanamide, N-(2,3-dihydroxypropyl)-N-hexadecyl octanamide, N-(2,3-dihydroxypropyl)-N-dodecyl-2-hydroxyhexadecanamide, N-(2,3 -dihydroxypropyl)-N-hexadecyl-2 -hydroxyhexadecanamide, N- (2 -hydroxy-3-hexadecyloxylpropyl)-N-(2-phosphoethyl) hexadecamide, N-(2-hydroxyoctadecyl)-N-(2-sulphoethyl) hexadecamide, N-(2-hydroxy-3-hexadecyl-oxypropyl)-N-(2-phosphoethyl) -ω-O-linoleoyldocosamide and mixtures thereof.

Suitable non-volatile silicone fluids are exemplified as polyalkylsiloxane, polyarylsiloxane, polyalkylarylsiloxane and polyethersiloxane copolymers. Mixtures of these fluids may also be used and are preferred in certain executions. The silicone fluid should be insoluble in the personal product matrix and present as a dispersion.

Examples of non-volatile polyalkylsiloxane fluids useful in the present invention include, for example, the polydimethylsiloxanes having viscosities from about 5 to about 600,000 centistokes at 25° C., preferably from about 350 to about 100,000 centistokes at 25° C.

Examples of non-volatile polyalkylarylsiloxane fluids useful in the present invention include, for example, the polymethylphenylsiloxanes having viscosities from about 15 to about 30,000 centistokes at 25° C.

Examples of non-volatile polyethersiloxane copolymer fluids useful in the present invention include, for example, the polyethylene oxide modified dimethylpolysiloxanes (dimethicone copolyol), polypropylene oxide modified dimethylpolysiloxanes and polyethylene oxide/polypropylene oxide modified dimethylpolysiloxanes, simethicone, cyclomethicone, cetyl dimethicone and mixtures thereof.

Other silicone materials useful in the present compositions are the silicone gums as described in U.S. Pat. No. 4,152,416 and in Chemistry and Technology of Silicones published by Academic Press (1968) both of which are incorporated herein by reference. Silicone gums are generally high molecular weight polydiorganosiloxanes having a mean molecular weight from about 200,000 to about 1,000,000. Specific examples of silicone gums include polydimethylsiloxane, (polydimethylsiloxane) (methylvinylsiloxane) copolymer, poly (dimethylsiloxanediphenyl)(methylvinylsiloxane) copolymer and mixtures thereof. References that describe suitable silicone fluids include U.S. Pat. Nos. 2,826,551, 3,964,500, 4,364,837, British Pat. No. 849,433 and Silicon Compounds distributed by Petrarch Systems, Inc. all of which are incorporated herein by reference.

Examples of polyols useful in the present invention include, but are not limited to propylene glycol (PG), dipropylene glycol, pentapropylene glycol, polypropylene glycol 2000 to 4000, polypropylene glycol 2000 to 4000 fatty acid esters, polyoxyethylene/polyoxypropylene glycols, polyoxypropylene/polyoxyethylene glycols, ethylene glycol, diethylene glycol, diethylene glycol mono/di-fatty acid esters, polyethylene glycol 200 to 6000 (PEG), polyethylene glycol 200 to 6000 mono/di-fatty acid esters, methoxy polyethylene glycol 350 to 5000, ethylene glycol mono/di-fatty acid esters, glycerol (glycerin), ethoxylated glycerol, propoxylated glycerol, glycerol mono/di/tri-fatty acid esters, polyglycerol, polyglycerol mono/di-fatty acid esters, erythritol, xylitol, sorbitol, sorbitan, ethoxylated sorbitol, hydroxypropyl sorbitol, mannitol, lactitol, hydrogenated starch hydrolyzates, 1,3-butylene glycol, 1,3-butylene glycol mono/di-esters, 1,2,6-hexane-triol, 2-ethyl-1,3-hexanediol, $C_{15}$–$C_{18}$ vincinal glycol, trimethanolethane, trimethyl-olpropane, ethoxylated trimethylolpropane, pentaerythritol, ethoxylated pentaerythritol, fructose, dextrin, glucose and the like. Preferred polyols are propylene glycol, propylene glycol stearate, propylene glycol dipelargonate, PEG-55 propylene glycol oleate, PEG-75, PEG-150, PEG-400, PPG-5 ceteth-20, ethylene glycol monostearate, ethylene glycol distearate, PEG-6 stearate, PEG-8 distearate, PEG-25 stearate, PEG-100 stearate, PEG-150 distearate, PEG-400 stearate, glycerin, diglycerin, decaglyceryl diisostearate, glyceryl laurate, glyceryl myristate, PEG-26 glycerate, caprylic/capric triglyceride, pentaerythrityl tetralaurate, sorbitan stearate, glycereth-7 and mixtures thereof.

Examples of fatty acids useful in the present invention include, but are not limited to pelargonic acid, lauric acid, myristic acid, palmitic acid, stearic acid, stearic acid (xxx), isostearic acid, hydroxystearic acid, oleic acid, linoleic acid, ricinoleic acid, arachidic acid, behenic acid, erucic acid, coconut fatty acid, soya fatty acid, tallow fatty acid, tall oil fatty acid, castor fatty acid, corn fatty acid, cottonseed fatty acid, palm fatty acid, rapeseed fatty acid, safflower fatty acid, sesame fatty acid, sunflower fatty acid and the like.

Examples of hygroscopic alkanolamides useful in the present invention include, but are not limited to acetamide MEA, acetamide DEA, lactamide MEA, lactamide DEA, lactaglucamide, lactamethylglucamide and the like.

Example of pyrrolidone carboxylic acids useful in the present invention include but are not limited to sodium, potassium, ammonium and alkanol ammonium salts of pyrrolidone carboxylic acid, ethyl pyrrolidone carboxylic acid and the like. Typical levels of skin conditioning agent are from about 1% to about 40%, preferably from about 2% to about 30%, even more preferably from about 3% to about 25% by weight of the composition.

Skin Feel Mildness Agents

The skin feel mildness agents useful in the present invention include, but are not limited to the cationic, anionic, amphoteric and nonionic polymers used in the cosmetic field. Reduced skin irritation benefits of cationic and nonionic polymers are described in Polymer JR for Skin Care Bulletin, by Union Carbide in (1977). The cationic polymers also provide a desirable soft, smooth and silky feeling to the skin. While wishing not to be bound to theory, it is believed that cationic polymers chemically interact with anionic surfactants to form complexes which may enhance overall mildness to skin characteristics. Also, there is a reason to believe that positively charged cationic polymers can bind with negatively charged sites on the skin to provide a softer skin feel after use. The cationic polymers are most preferred because they provide the best skin feel benefits.

Examples of cationic and nonionic polymers include Polymer JR-400 sold by Union Carbide, Merquat 100 and 550 sold by Merck and Company Inc., Jaguar C14-S and Jaguar HP-60 sold by Stein Hall, Mirapol A15 sold by Miranol Chemical Company Inc., Galactasol 811 sold by Henkel Inc. and Stalok 300 and 400 sold by Staley Inc., as well as hydroxypropyl gaur gum, carboxymethyl cellulose, hydroxyethyl cellulose, sodium isethionate, acrylates/octylpropenamide copolymer, copolymers of dimethylaminoethylmethacrylate and acrylamide, copolymers of dimethyldiallylammonium chloride and acrylamide and the like. A more complete list of cationic polymers useful in the present invention is discribed in U.S. Patent No. 4,438,095 which is incorporated herein by reference. Typical levels of skin conditioning agent are from about 0% to about 5%, preferably from about 0% to about 4%, even more preferably from about 0% to about 3% by weight of the composition.

Hydroxy Acids

Hydroxy acids have been taught in the art for use as agents that exfoliate dead skin cells leaving skin smoother and tighter with a more youthful appearance. In addition, hydroxy acid treatments help reduce liver and sun spots as well as diminution of wrinkles. Examples of hydroxy acids useful in the present invention include the α-hydroxy acids (2-hydroxy acids) which may be isolated from natural sources or prepared by the hydrolysis of a α-halo acids, or by acid hydrolysis of cyanohydrins of aldehydes or ketones, or by the hydrolysis of α-nitrato acids with aqueous sulfite solutions. Specific examples of α-hydroxy acids include, but are not limited glycolic acid (hydroxyacetic acid), DL-lactic acid (2-hydroxypropionic acid), D-lactic acid, L-lactic acid, 2-hydroxybutyric acid, 2-hydroxycaproic acid, 2-hydroxycaprylic acid, 2-hydroxycapric acid, 2-hydroxylauric acid, 2-hydroxymyristic acid, 2-hydroxypalmitic acid, 2-hydroxypalmiticoleic acid, 2-hydroxystearic acid, 2-hydroxyoleic acid, 2-hydroxylinoleic acid, 2-hydroxylinolenic acid, 2-hydroxyricinoleic acid, 2-hydroxygadoleic acid, 2-hydroxyarachidonic acid, 2-hydroxybehenic acid, 2-hydroxycetoleic acid, 2-hydroxyerucic acid and mixtures thereof.

Other examples of hydroxy acids useful in the present invention include the β-Hydroxy acids (3-hydroxy acids) which are prepared by catalytic reduction of β-keto esters followed by hydrolysis or by the Reformatsky Reaction. Specific examples of β-hydroxy acids include, but are not limited 3-hydroxypropionic acid, 3-hydroxybutyric acid, 3-hydroxycaproic acid, 3-hydroxycaprylic acid, 3-hydroxycapric acid, 3-hydroxylauric acid, 3-hydroxymyristic acid, 3-hydroxypalmitic acid, 3-hydroxypalmitictoleic acid, 3-hydroxystearic acid, 3-hydroxyoleic acid, 3-hydroxylinoleic acid, 3-hydroxylinolenic acid, 3-hydroxyricinoleic acid, 3-hydroxygadoleic acid, 3-hydroxyarachidonic acid, 3-hydroxybehenic acid, 3-hydroxycetoleic acid, 3-hydroxyerucic acid and mixtures thereof.

Still other examples of hydroxy acids useful in the present invention include the γ-hydroxy acids (4-hydroxy acids), δ-hydroxy acids (5-hydroxy acids), aldonic acids, aldoheptonic acids, aldobionic acids, mevalonic acid and thier lactones as well as the hydroxydicarboxylic acids such as maleic acid, malic acid, tataric acid, tartronic acid (hydroxypropanedioic acid), phloionic acid (9,10-hydroxyoctadecanedioic acid) and the like.

The natural and synthetic fruit acids such as glycolic acid (from sugar cane or sugar beet or by reaction of formaldehyde with carbon monoxide), malic acid (from apples and grapes or from maleic anhydride and water), lactic acid (from sour milk or by fermentation of corn or sugar substrates) and citric acid (from fruits and vegetables or by fermentation of corn or sugar substrates) and the like are useful as well. Typical levels of skin conditioning agent are from about 0% to about 10%, preferably from about 0% to about 8%, even more preferably from about 0% to about 6% by weight of the composition.

Auxiliary Thickening Agents

Various materials have been taught in the art as auxiliary thickening agents, which are useful in combination with heteroatom containing alkyl aldonamide compounds of the present invention for enhancing viscosity and rendering the composition more acceptable.

Examples of common thickening agents include fumed silica, bentonite (hydrated aluminum silicone dioxide), PEG 55 propylene glycol oleate, PEG 6000 distearate, cellulose gum, hydroxypropyl cellulose, hydroxyethyl cellulose, hydroxypropyl methyl cellulose, sodium carboxymethyl cellulose, carrageenan, veegum (magnesium aluminum silicate), xanthan gum, gaur hydroxypropyltrimonium chloride, gaur gum, pectin, amine oxides, glucose glutamate, stearamidopropyldimethylamine lactate, carbomer 934 (acrylic acid polymer with an average molecular weight of 3,000,000), carbomer 941 (acrylic acid polymer with an average molecular weight of 1,250,000), polyvinylpyrrolidone (PVP) and the alkanolamides.

Examples of another type of thickening agent (gelling agent/viscosity control agent) found to be useful in the present invention include the poly(oxyethylene)-poly(oxypropylene) block copolymers such as poloxamer 101 through 941 sold by BASF, ICI Americas and Hodag. Of this class of thickening agent, poloxamer 101, poloxamer 182, poloxamer 238, poloxamer 934 and poloxamer 941 and mixtures thereof are preferred and poloxamer 188, poloxamer 237, poloxamer 338, poloxamer 407 and mixtures thereof are highly preferred. The poly(oxyethylene)-poly(oxypropylene) block polymers are of the formula:

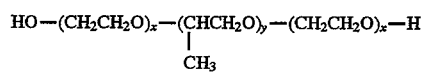

wherein:
X=75 and Y=30 for poloxamer 188
X=62 and Y=39 for poloxamer 237
X=128 and Y=54 for poloxamer 338
X=98 and Y=67 for poloxamer 407

These products are complex mixtures of copolymer produced in a wide range of molecular weights (1,100–14,000) with varying degrees of ethylene oxide and propylene oxide. The block polymers are prepared by polymerizing propylene oxide in a controlled fashion to give a desired weight followed by ethoxylation with ethylene oxide. The ethoxylated portions of the block polymer can provide from about 10% to about 80% by weight of the final product.

Preferred are the alkanolamides which are prepared by the reaction of a $C_8$–$C_{18}$ alkyl fatty acid, $C_8$–$C_{18}$ alkyl fatty acid ester or $C_8$–$C_{18}$ alkyl fatty acid halide with a hydroxyl alkylamine such as monoethanolamine or diethanolamine. Suitable examples of alkanolamides useful as auxiliary thickening agents include lauric monoethanolamide, lauric diethanolamide, myristic monoethanolamide, myristic diethanolamide, coco monoethanolamide, coco diethanolamide, palmitic monoethanolamide, linoleic monoethanolamide, linoleic diethanolamide, hydroxystearyl monoethanolamide, almond diethanolamide, palm kernel diethanolamide, oleic monoethanolamide and mixtures thereof. Most highly preferred auxiliary thickening agent useful in the present invention include are lauric monoethanolamide (lauramide MEA), lauric diethanolamide (lauramide DEA), coco monoethanolarnide (cocoamide MEA) and coco diethanolamide (cocoamide DEA) which may be present from about 0% to about 10%, preferably from about 0% to about 8%, even more preferably from about 0% to about 6% by weight of the composition.

Typical levels of carbohydrate thickeners are from about 0% to about 5%, preferably from about 0% to about 4%, even more preferably from about 0% to about 3% by weight of the composition.

Suspending Agents

Various materials have been taught in the art as agents that are useful in suspending certain performance ingredients such as skin feel mildness agents, silicone fluids, and the like, uniformly, thereby assisting in the delivery of the desirable performance attributes associated with these ingredients. The suspending agent useful in the present invention can be any of several long chain acyl derivatives or mixtures thereof. Included are the glycol mono-, di- and triesters having about 14 to about 22 carbon atoms. Preferred glycol esters include the ethylene glycol mono- and distearates, glyceryl stearates, palm oil glyceride, tripalmitin, tristearin and mixtures thereof.

Another example of a suspending agent useful in the present invention include the alkanolamides having from about 14 to about 22 carbon atoms. Preferred alkanolamides are stearic monoethanolamide, steric diethanolamide, stearic monoisopropanolamide, stearic monoethanolamide stearate and mixtures thereof.

Still another example of a suspending agent useful in the present invention include the long chain fatty acid esters such as stearyl stearate, stearyl palmirate and palmityl palmirate.

Still another example of a suitable suspending agent useful in the present invention include the long chain amine oxides having from about 14 to about 22 carbon atoms. Preferred amine oxides are hexadecyldimethylamine oxide and octadecyldimethylamine oxide.

Yet another example of a suitable suspending agent (or thickening agent) useful in the present invention include the carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, hydroxymethyl carboxypropyl cellulose, methyl cellulose, ethyl cellulose, guar gum, gum karaya, gum tragacanth, gum arabic, gum acacia, gum agar, xanthan gum and mixtures thereof. Preferred carbohydrate gums are the cellulose gums and xanthan gum. The carbohydrate gums also have a smoothing, noninsulating, film-forming and moisturizing effect.

Of all the above described types of suspending agents, preferred compounds include the long chain glycol esters and the carbohydrate gums.

The suspending agent or mixtures of agent may be present from about 0% to about 10%, preferably from about 0% to about 8%, even more preferably from about 0% to about 6% by weight of the composition.

Water

Water is the last essential component of the present invention and forms the remainder of the composition.

Water is generally present from about 1% to about 95%, preferably from about 10% to about 80%.

Optional Ingredients (Auxilary Agents)

The personal product compositions herein can contain a variety of less essential optional ingredients (auxilary agents) suitable for rendering such compositions more acceptable. Such ingredients are well known to those skilled in the art and include, but are not limited to viscosity control agents, dispersants, solubilizing/clarifying agents, stabilizers, sunscreens/UV absorbers, opacifiers/pearlescent agents, vitamins, amino acids, proteins, chelating/sequestering agents, hydrotropes, preservatives/antimicrobial agents, bactericides/fungicides, antioxidants, pH control agents, buffering agents, antiperspirant/deodorant agents, heeling agents, colorants and perfumes/fragrances. These ingredients, when used, are added at their usual levels, each generally up to about 10% by weight of the composition and usually totaling up to about 0.001% to about 45% by weight of the composition.

Examples of organic viscosity modifying agents useful in the present invention include $C_8$–$C_{18}$ alkyl fatty alcohols, $C_8$–$C_{18}$ alkyl fatty acids, $C_8$–$C_{18}$ alkyl fatty esters, ethanol, isopropanol and benzyl alcohol. Examples of inorganic viscosity modifying agents include ionizable salts such as sodium chloride, potassium chloride, calcium chloride, magnesium chloride, potassium bromide, ammonium chloride, sodium sulfate, potassium sulfate, magnesium sulfate, sodium isethionate and sodium thiosulfate. The ionizable salts are particularly useful for obtaining or modifying a desired viscosity. The amount of ionizable salt used depends on the amount of active ingredient present and can be adjusted according to the formulators desires. Typical levels of salt used to control composition viscosity are from about 0.1% to about 10% by weight of the composition.

Examples of solubilizing or clarifying agents useful in the present invention which assist in maintaining composition clarity by solubilizing poorly soluble ingredients include methanol, ethanol, propanol, isopropanol, butanol, ethoxydiglycol, phenyl ethanol, phenyl propanol, benzyl alcohol, ethyl buyrate, isopropyl butyrate, diethyl phthalate, phenylethyldimethyl carbinol, ethyl-6-acetoxyhexanoate, methyl(2-pentanyl-3-oxy)cyclopentylacetate, ethylene glycol, diethylene glycol, triethylene glycol, polyethylene glycol having a molecular weight of about 200 to about 1000, propylene glycol, glycerol, 3,6-dimethyl-4-octyne-3, 6-diol, 2-methyl-2,4-pentanediol, 2-ethyl- 1,3-hexanediol and nonionic surfactants particularly polyoxyethylene nonionic surfactants. Typical levels of solubilizing or clarifying agent are from about 0% to about 10% by weight of the composition.

Examples of sunscreens or UV absorbers useful in the present invention which protect the skin and certain sensitive ingredients from harmful sunlight include dipropyleneglycol salicylate, octyl salicylate, 2-ethylhexyl p-dimethylaminobenzoate (octyldimethyl-PABA), polyoxyethylene p-dimethylaminobenzoate (PEG-25 PABA), Tri-PABA-panthenol, dromtrizole, 2-ethylhexyl p-methoxycinnamate, DEA p-methoxycinnamate, butyl methoxybenzoylmethane, benzophenones 1 through 12 particularly, 2,4-dihydroxybenophenone (benzophenone 1), 2,2',4,4'-tetrahydroxybenzophenone (benzophenone 2), 2-hydroxy-4-methoxybenzophenone (benzophenone 3), 2-hydroxy-4-methoxybenzophenone-5-sulfonic acid (benzophenone 4), 2,2'-dihydroxy-4,4'-dimethoxybenzophenone (benzophenone 6), 2,2'-dihydroxy-4-methoxybenzophenone (benzophenone 8), disodium2,2'-dihydroxy-4,4'-dimethoxy-5,5'-disulfobenzophenone (benzophenone 9), 2-hydroxy-4-n-octoxybenzophenone, methyl anthranilate, 2-(2-hydroxy-5'-methylphenyl)benzotriazole, 2-phenylbenzimidazole-5-sulfonic acid, 2-hexanolethyl salicylate, octyl methoxycinnamate, butyl metoxydibenzoylmethane, ethyl p-amino benzoate and mixtures thereof. Preferred sunscreens are the benzophenones 1 through 6, 8, 9 and 11. Typical levels of sunscreen or UV absorber are from about 0% to about 8% by weight of the composition.

Examples of opacifiers and pearlescent agents useful in the present invention which provide a soft, silvery and pearly luster to personal product compositions include hexadecanol, octadecanol, tallow alcohol, oleyl alcohol, ethylene glycol monostearate, ethylene glycol distearate, diethylene glycol distearate, triethylene glycol distearate, glycerol mono/distearate, PEG 400 stearate, PEG 600 oleate, PEG-4 to PEG 150 laurate/dilaurate, PEG 4 to PEG 150 stearate/distearate, PEG-4 to PEG 150 oleate/dioleate, coco gluconamide, tallow gluconamide, dodecyl gluconamide, hexadecyl gluconamide, octadecyl gluconamide, coco glucoheptonamide, tallow lactobionamide, octadecyl lactobionamide, tallow maltobionamide, octadecyl glucoheptonamide, tallow glucoheptonamide, bismuthoxychloride, spermaceti, magnesium silicate, calcium silicate, guanine, zinc oxide, titanium dioxide (anatose form or rutile form), titanium dioxide coated mica, iron oxide, talc, silica, bentone EW clay and coloured pigments coated mica and as well as the zinc, calcium and magnesium salts of fatty acids such as myristic acid, palmitic acid, stearic acid, behenic acid, coconut fatty acid. Preferred are the non-heteroatom containing alkyl aldonamides/aldobionamides and the ethylene glycol esters such as ethylene glycol monostearate and distearate. Typical levels of opacifiers or pearlescent agent are from about 0% to about 7% by weight of the composition.

Examples of vitamins useful in the present invention which provide the hair with valuble nutrition include vitamin A (as retinyl acetate, propionate or palmitate) provitamin A (based on carrot extract, as β-carotene), vitamin $B_1$ (as thiamine mononitrate), vitamin $B_2$ (as riboflavin), vitamin $B_3$ (as niacinamide), vitamin $B_5$ (as pantothenic acid), provitamin $B_5$ (as panthenol), vitamin $B_6$ (as pyridoxine hydrochloride, dioctenoate, dilaurate, dipalmitate or tripalmitate), vitamin $B_{12}$ (as cyanocobalamin), vitamin $B_{15}$ (as pangamic acid), vitamin C (as ascorbic acid), vitamin $D_2$ (as ergocalciferol), vitamin $D_3$ (as cholecalciferol), vitamin E (as dl-α-tocopherol acetate, linoleate or nicotinate,), vitamin F (as glyceryl linoleate and glyceryl linolenate), vitamin $K_1$ (as phytonadione), vitamin $K_3$ (as menadione), paba (p-aminobenzoic acid), choline, folic acid, biotin, allantoin biotin, retinol, inositol, allantoin calcium pantothenate, licithin (choline di-$C_{16}$–$C_{18}$ glycerophosphate), cholesterol, PEG 16 soya sterol, bisabolol, bioflavoniod and mixtures thereof. Preferred vitamins are provitamin A, vitamin $B_1$, vitamin $B_2$, provitamin $B_5$, vitamin $B_6$, vitamin $B_{12}$ and vitamin E. Typical levels of vitamin are from about 0% to about 7% by weight of the composition.

Examples of amino acids useful in the present invention which provide the skin with valuble nutrition include alanine, β-alanine, N-methylalanine, N-phenylalanine, α-aminoisobutyric acid, α-aminobutyric acid, α-aminocaproic acid, ε-aminocaproic acid, glycine, N-ethylglycine, N-propylglycine, N-butylglycine, leucine, methionine, derivatives of methionine, sarcosine, serine, norvaline, tryptophan, lysine, aspartic acid, glutamic acid, iminodiacetic acid, keratin amino acids (keratin polypeptides), silk amino acids, allantoin acetyl methionine, allantoin, deoxyribonucleic acid, protamine/nucleic acid complex, nucleic acid, collagen amino acids, retinyl palmitate polypeptide, proline, polyglucan and mixtures thereof. Preferred amino acids are glycine, methionine, sarcosine, keratin amino acids and silk amino acids. Typical levels of amino acid are from about 0% to about 7% by weight of the composition.

Examples of proteins useful in the present invention which provide the skin with valuble nutrition include hydrolyzed casein, hydrolyzed collagen (hydrolyzed animal protein), myristoyl hydrolyzed animal protein, hydrolyzed corn protein, hydrolyzed glycosaminoglycans, hydrolyzed keratin (keratin protein), hydrolyzed milk protein, hydrolyzed pea protein, hydrolyzed potato protein, hydrolyzed rice protein, hydrolyzed silk (silk protein), hydrolyzed soy protein, hydrolyzed vegetable protein, hydrolyzed wheat gluten, hydrolyzed wheat protein, hydrolyzed yeast protein and mixtures thereof. Preferred proteins are hydrolyzed collagen, hydrolyzed keratin protein, hydrolyzed silk protein, hydrolyzed soy protein, TEA coco hydrolyzed animal protein, potassium coco hydrolyzed animal protein, propyltrimonium hydrolyzed collagen and hydrolyzed animal elastin. Typical levels of protein are from about 0% to about 7% by weight of the composition.

Examples of chelating or sequestering agents (builders) useful in the present invention include the sodium, potassium and ammonium salts of diphosphoric acid, triphosphoric acid, pyrophosphoric acid, orthophosphoric acid, hexametaphosphoric acid, 1-hydroxyethane-1,1-phosphonic acid, diethylenetriamine penta(methylene diphosphonic acid), ethylenediamine tetraacetic acid (EDTA), diethylenetriamine pentaacetic acid (DTPA), N-(hydroxyethyl) ethylenediamine triacetic acid (HEDTA), propylenediamine tetraacetic acid (PDTA), nitrilotriacetic acid (NTA), mellitic acid, 1,2,3,4-cyclopentane tetracarboxylic acid, succinic acid, lauryl succinic acid, oxydisuccinic acid (ODS), carboxymethyloxysuccinic acid, citric acid, lactic acid, tartaric acid, O-carboxymethyltartronic acid, polyacrylic acid, poly (α-hydroxyacrylic acid), poly(tetramethylene-1,2-dicarboxylic acid), poly(4-methoxytetramethylene-1,2-dicarboxylic acid), acrylic acid/maleic acid copolymer (polycarboxylate), acrylic acid/allyl alcohol copolymer (polycarboxylate), sodium PCA, gluconic acid, glucoheptonic acid, lactobionic acid, maltobionic acid, 1-hydroxyethylidene biphosphate, etidronic acid and mixtures thereof. Preferred are the sodium, potassium and ammonium salts of ethylenediamine tetraacetic acid and diethylenetriamine pentaacetic acid. Typical levels of chelating or sequestering agent useful for complexing hard ions such as calcium and magnesium are from about 0% to about 6% by weight of the composition.

Examples of hydrotropes useful in the present invention which assist in maintaining personal product composition clarity include the sodium, potassium and ammonium salts of toluenesulfonic acid, ethylbenzenesulfonic acid, xylenesulfonic acid, cumenesulfonic acid, urea, and mixtures thereof. Preferred are the sodium, potassium and ammonium salts of toluenesulfonic acid and xylenesulfonic acid. Typical levels of hydrotrope are from about 0% to about 6% by weight of the composition.

Examples of preservatives or antimicrobial agents that function as bactericides and/or fungicides useful in the present invention include glutaraldehyde, formaldehyde, paraformaldehyde, glyoxal, benzoic acid, salicylic acid, sorbic acid, dehydroacetic acid, benzyl alcohol, ethanol, 2-phenoxyethanol, chlorohexidine hydrochloride, triclosan, chloroacetamide, p-chloro-m-xylenol, 1-(3-chloroallyl)-3, 5,7-triaza-1-azoniaadamantane chloride, methyl paraben, propyl paraben, butyl paraben, benzyl paraben, imidazolidinyl urea, diazolidinyl urea, monomethylol dimethyl hydantoin (MDM hydantoin), dimethylol dimethyl hydantoin (DMDM hydantoin), iodopropylnyl butylcarbamate, 2-bromo-2-nitropropane-1,3-diol, 2-octyl-4-isothiazolin-3-one, 5-chloro-2-methyl-4-isothiazolin-3-one (methylchloroisothiazoline), 2-methyl-4-isothiazolin-3-one (methylisothaizoline), N-(3-chloroallyl) hexaminium chloride and dicocodimethylammonium chloride. Preferred is a combination of methyl isothiazoline and chloromethyl isothiazoline as described in U.S. Pat. No. 4,265,899 sold under the trade name Kathon CG by Rohm and Haas Company which is incorporated herein by reference. Typical levels of preservative used to control bacterial or fungal action are from about 0.001% to about 4% by weight of the composition.

Examples of antioxidants useful in the present invention which prevent the oxidation of certain ingredients by air and prevent the development of unpleasant, rancid odors include vitamin E (tocopherol), lecithin, wheat germ oil, sodium sulfite, sodium bisulfite, uric acid, propyl gallate, butylated hydroxyanisole (BHA), toluhydroquinone (THQ) sold as Tenox PG, Tenox BHA and Tenox THQ by Eastman Chemical Products Inc., and butylated hydroxytoluene (BHT) sold as Sustane BHT by UOP Process Division. Typical levels of antioxidant used to prevent oxidation, are from about 0% to about 4% by weight of the composition.

Examples of pH-control agents useful in the present invention include citric acid, tartaric acid, lactic acid, gluconic acid, lactobionic acid, glycolic acid, propionic acid, succinic acid, maleic acid, hydrochloric acid, phosphoric acid, nitric acid, sulfuric acid, formic acid, boric acid, acetic acid, benzoic acid, methylsulfonic acid, ethylsulfonic acid, palmitic acid, stearic acid, hexadecylamine, octadecylamine, dimethylstearylamine, stearylamidopropyldimethylamine, sodium hydroxide, sodium carbonate, potassium hydroxide, triethanolamine, borax, sodium lactate, sodium benzoate and mixtures thereof. The amount of pH-control agent used will be that which is sufficient to provide the desired pH.

Examples of buffering agents useful in the present invention which resist changes in their hydrogen-ion concentration resulting in a constant pH include mixtures of weak acids (or their salts) and weak bases (or their salts) such as citric acid/disodium phosphate, citric acid/sodium citrate, acetic acid/sodium acetate and citric acid/borax (sodium tetraborate). The composition of the salt pair is highly variable and one skilled in the art can with simple experimentation arrive at various salt pairs that will be functional and that will not detract from the overall compositions. The pH of the present compositions may be in the range of about 5 to about 9, preferably from about 5.5 to about 8.5, even more preferably from about 6 to about 8. In practice however, a personal product composition is adjusted to a pH of about less than 7 to provide a composition that is non-irritating and non-damaging to the skin of the consumer. The amount of buffering agent used will be that which is sufficient to provide the desired buffered pH.

Examples of antiperspirant/deodorant agents which inhibit the flow of perspiration and reduce mal-odor include, but are not limited to well known antiperspirant metal salts of aluminum, zinc, zirconium and zirconium aluminum mixtures of sulfates, chlorides, chlorohydroxides, tetrachlorohydrex glycinates, alums, formates, lactates, benzyl sulfonates, succinates, phenol sulfonates and the like. Preferably the antiperspirant metallic salt of choice is aluminum chlorohydrate and aluminum zirconium tetrachlorohydrex glycine. The use of this salt as an antiperspirant agent and a method for making the same is described in U.S. Pat. No. 3,904,741 to Jones. Such compounds are of the general formula $Al_2(OH)_xCl_{(6-x)}$ wherein x is an interger or non-integer between 0 and 6 giving a product which may be a mixture of varied proportions of such compounds as $Al_5OH_5Cl_{14}$, $Al_2OH_5Cl_2$, $Al_5OH_5Cl_4$ and the like. Typical levels of antiperspirant/deodorant agent are from about 0% to about 35%, preferably from about 0% to about 25% by weight of the composition.

The composition may further include a complexing agent such as an organic acid or derivative thereof that are capable of forming complexes with the anti-perspirant metallic salt. Examples of such complexing agents include, but are not limited to acetic acid, propionic acid, oxalic acid, malonic acid, succinic acid, tartaric acid, glycine and the like acid, together with their cosmetically acceptable salts. Typical levels of complexing agent are from about 0% to about 15%, preferably from about 0% to about 10%, by weight of the composition.

The composition may also further include a hardening agent selected from the group consisting of lower alkanol amines, diamines and amides wherein such materials comprise at least two lower alkanol groups, preferably from about two to about four lower alkanol groups having from about 2 to about 4 carbon atoms. Examples of such hardening agents include, but are not limited to tetrahydroxy-alkyldiamine compounds such as tetrahydroxypropylethylene diamine, polyoxamine compounds such as polyoxyethylene, polyoxypropylene block copolymers of ethylene diamine and alkanolamide compounds such as coconut diethanolamide and lauryl monoethanolamide. Typical levels of harding agent are from about 0% to about 5% by weight of the composition.

Examples of heeling agents which function to stimulate the growth of healthy skin tissue include allantion, aluminum dihydroxy allantoinate, urea, uric acid, aloe vera gel, methyl manuronate, uronic acids, sucrose octaacetate, menthol, hydrolyzed elastin, sodium hyaluronate, mucopolysacharides, chitosans, sodium alginate and mixtures thereof. Typical levels of heeling agent are from about 0% to about 6% by weight of the composition.

Examples of colorant which provide color to the personal product compositions of the invention include D&C blue #1, D&C blue #4, D&C brown #1, D&C green #5 through #8, D&C orange #4 through #11, D&C yellow #2 through #11, D&C red #6 through #40, D&C violet #2, FD&C blue #1, FD&C blue #2, FD&C blue #4, FD&C red #3, FD&C red #4, FD&C red #33, FD&C red #40, FD&C yellow #5, FD&C yellow #6, FD&C yellow #10, FD&C orange #4, FD&C green #3, carmine and mixtures thereof. Typical levels of colorant are from about 0% to about 2% by weight of the composition.

Other minor components include perfumes or fragrances which may be present from about 0.1% to about 4% by weight of the composition.

Many additional optional ingredients that are useful in the present invention are described in McCutcheon's, Detergents and Emulsifiers (Vol 1) and McCutcheon's, Functional Materials (Vol 2), 1992 Annual Edition, published by McCutcheon's MC Publishing Co. as well as the CTFA (Cosmetic, Toiletry and Fragrance Association) 1992 International Buyers Guide, published by CTFA Publications and OPD 1993 Chemical Buyers Directory 80th Annual Edition, published by Schnell Publishing Co. which are all incorporated herein by reference.

According to the present invention, a personal product composition comprises the following ingredients:

(a) from about 0.1% to about 45% by weight of the composition is a heteroatom containing alkyl aldonamide compound;

(b) from about 0% to about 50% by weight of the composition is a cosurfactant (cleansing agent) selected from the group consisting of soap, anionic, nonionic, amphoteric, zwitterionic, cationic and mixtures thereof;

(c) from about 1% to about 40% by weight of the composition is a skin conditioning agent;

(d) from about 0% to about 5% by weight of the composition is a skin feel mildness agent;

(e) from about 0% to about 10% by weight of the composition is a hydroxy acid;

(fi from about 0% to about 10% by weight of the composition is an auxiliary thickening agent;

(g) from about 0% to about 10% by weight of the composition is a suspending agent;

(h) from about 0.1% to about 10% by weight of the composition is a viscosity control agent;

(i) from about 0% to about 10% by weight of the composition is a solubilizing/clarifying agent;

(j) from about 0% to about 8% by weight of the composition is a sunscreen/UV absorber;

(k) from about 0% to about 7% by weight of the composition is an opacifier/pearlescent agent;

(l) from about 0% to about 7% by weight of the composition is a vitamin;

(m) from about 0% to about 7% by weight of the composition is an amino acid;

(n) from about 0% to about 7% by weight of the composition is a protein;

(o) from about 0% to about 6% by weight of the composition is a chelating/sequestering agent;

(p) from about 0% to about 6% by weight of the composition is an hydrotrope;

(q) from about 0.001% to about 4% by weight of the composition is a preservative/antimicrobial agent;

(r) from about 0% to about 4% by weight of the composition is an antioxidant;

(s) a pH control agent or buffering salt pair in an amount sufficient to provide a pH in the rage of about 5 to about 9

(t) from about 0% to about 35% by weight of the composition is an antiperspirant/deodorant agent;

(u) from about 0% to about 15% by weight of the composition is an complexing agent;

(v) from about 0% to about 5% by weight of the composition is an hardening agent;

(w) from about 0% to about 4% by weight of the composition is a heeling agent;

(x) from about 0% to about 2% by weight of the composition is a colorant;

(y) from about 0.1% to about 4% by weight of the composition is a perfume/fragrance; and (z) the remainder is water.

In a more narrow aspect of the present invention, a personal product composition comprises the following ingredients:

(a) from about 0.2% to about 40% by weight of the composition is a heteroatom containing alkyl aldonamide compound;

(b) from about 0.1% to about 45% by weight of the composition is a cosurfactant (cleansing agent) selected from the group consisting of soap, anionic, nonionic, amphoteric, zwitterionic, cationic and mixtures thereof;

(c) from about 2% to about 30% by weight of the composition is a skin conditioning agent;

(d) from about 0% to about 4% by weight of the composition is a skin feel mildness agent;

(e) from about 0% to about 8% by weight of the composition is a hydroxy acid;

(f) from about 0% to about 8% by weight of the composition is an auxiliary thickening agent;

(g) from about 0% to about 8% by weight of the composition is a suspending agent;

(h) from about 0.2% to about 8% by weight of the composition is a viscosity control agent;

(i) from about 0% to about 8% by weight of the composition is a solubilizing/clarifying agent;

(j) from about 0% to about 7% by weight of the composition is a sunscreen/UV absorber;

(k) from about 0% to about 6% by weight of the composition is an opacifier/pearlescent agent;

(l) from about 0% to about 5% by weight of the composition is a vitamin;

(m) from about 0% to about 5% by weight of the composition is an amino acid;

(n) from about 0% to about 5% by weight of the composition is a protein;

(o) from about 0% to about 4% by weight of the composition is a chelating/sequestering agent;

(p) from about 0% to about 4% by weight of the composition is an hydrotrope;

(q) from about 0.002% to about 2% by weight of the composition is a preservative/antimicrobial agent;

(r) from about 0% to about 2% by weight of the composition is an antioxidant;

(s) a pH control agent or buffering salt pair in an amount sufficient to provide a pH in the range of about 5.5 to about 8.5

(t) from about 0% to about 25% by weight of the composition is an antiperspirant/deodorant agent;

(u) from about 0% to about 10% by weight of the composition is an complexing agent;

(v) from about 0% to about 4% by weight of the composition is an hardening agent;

(w) from about 0% to about 3% by weight of the composition is a heeling agent;

(x) from about 0% to about 0.5% by weight of the composition is a colorant;

(y) from about 0.1% to about 3% by weight of the composition is a perfume/fragrance; and (z) the remainder is water.

In a even more narrow aspect of the present invention, a personal product composition comprises the following ingredients:

(a) from about 0.3% to about 35% by weight of the composition is a heteroatom containing alkyl aldonamide compound;

(b) from about 0.2% to about 40% by weight of the composition is a cosurfactant (cleansing agent) selected from the group consisting of soap, anionic, nonionic, amphoteric, zwitterionic, cationic and mixtures thereof;

(c) from about 3% to about 25% by weight of the composition is a skin conditioning agent;

(d) from about 0% to about 3% by weight of the composition is a skin feel mildness agent;

(e) from about 0% to about 6% by weight of the composition is a hydroxy acid;

(f) from about 0% to about 6% by weight of the composition is an auxiliary thickening agent;

(g) from about 0% to about 6% by weight of the composition is a suspending agent;

(h) from about 0.001% to about 45% by weight of the composition is an optional ingredient(s); and (i) the remainder is water.

In the most narrow aspect of the present invention, a personal product composition comprises the following ingredients:

(a) from about 0.4% to about :30% by weight of the composition is a heteroatom containing alkyl aldonamide compound;

(b) from about 0.3% to about 35% by weight of the composition is a cosurfactant (cleansing agent) selected from the group consisting of soap, anionic, nonionic, amphoteric, zwitterionic, cationic and mixtures thereof;

(c) from about 3.1% to about 25% by weight of the composition is a skin conditioning agent;

(d) from about 0% to about 3% by weight of the composition is a skin feel mildness agent;

(e) from about 0% to about 5% by weight of the composition is a hydroxy acid;

(f) from about 0% to about 4% by weight of the composition is an auxiliary thickening agent;

(g) from about 0% to about 4% by weight of the composition is a suspending agent;

(h) from about 0.01% to about 35% by weight of the composition is an optional ingredient(s); and (i) the remainder is water.

Method of Manufacture

Aldonic acids, aldobionic acids and their lactones are prepared by microbial fermentation, chemical oxidation or enzymatic oxidation of sugars. (See for example, EP 142, 725 (1985) to Saito, et al.; EP 232,202 (1986) and EP 233,816 (1987) to Fuertes et al.; JP 62/269728 (1987) to Kimura, et al.; Biotechnology Letters 6:487 (1984) to Chang, et al.; Biotechnology Letters 9:252 (1987) to Burdick, et al.; German Pat. No. 2,911,192 (1980) and U.S. Pat. No. 4,460,686 (1984) to Hartmeier and Appl. Microbiol. Biotechnol. 21:356 (1985) to Seiskari, et al. all of which are incorporated herein by reference). Examples of aldonic acids, aldobionic acids and their lactones suitable for the preparation of heteroatom containing alkyl aldonamide compounds include but are not limited to threonic acid, arabinonic acid, lyxonic acid, allonic acid, altronic acid, idonic acid, talonic acid, gluconic acid, galactonic acid, mannonic acid, lactobionic acid, maltobionic acid, cellobionic acid, gentiobionic acid, melibionic acid, glucopyranosyl-(1-5)-arabinonic acid, erythronolactone, ribonolactone, xylonolactone, gluconolactone, galactonolactone, mannonolactone, gulonolactone, glucoheptonolactone, lactobionolactone and maltobionolactone.

Heteroatom containing alkyl aldonamide compounds of the invention are prepared by reaction of the appropriate heteroatom containing amine with an aldonic acid or aldobionic acid (preferably with the corresponding aldonolactone or aldobionolactone) in an organic solvent (such as methanol) with or without an acid catalyst (such as methanesulfonic acid) at about 0° C. to about 90° C., preferably at about 20° C. to about 70° C., even more preferably at about 30° C. to about 60° C.

Heteroatom containing alkyl aldonamide salt compounds of the invention are prepared by reaction of an alkylaminoalkyl aldonamide or aldobionamide compound with an organic or inorganic acid in water or organic solvent at about 0° C. to about 100° C., preferably at about 20° C. to about 70° C., even more preferably at about 25° C. to about 55° C.

All raw materials such as D-gluconolactone, D-lactobionolactone alkyloxypropylamine, alkylaminopropylamine and alkyloxypropylaminopropylamine are available in bulk and the end products are easily prepared by the commercially feasible process described above.

The compositions of the present invention can be prepared by adding the appropriate amount of water and admixing the active ingredients with appropriate stirring at about 40° C. to about 100° C., preferably from about 50° C. to about 80° C., even more preferably from about 60° C. to about 75° C. Ingredients may be added as a main mix, partial mix or as a premix. When the conditioning agent silicone is used, it is sometimes added as the last ingredient and it is sheared with a high shear mixer until the silicone particle size has an average diameter of 10 microns or less. All temperature sensitive components are added after the composition has cooled from about 21° C. to about 38° C. after which the composition is stirred until homogeneous. Commercial quantities of the compositions of the present invention can be easily prepared in a stainless steel or glass lined kettle equipped with a provision for agitation, heating and cooling. Processing may be continuous or batch wise, however cost savings may be further increased through continuous processing by virtue of economy of scale.

Personal Product Types and Form

Personal products are available in a variety of types and forms. A classification according to product type would consist of bath products, cleansing products, skin care products, shaving products and deodorant/antiperspirant products.

Examples of bath products include, but are not limited to bath oils, foam or bubble bathes, theraputic bathes, after bath products, after bath splash products and the like.

Examples of cleansing products include, but are not limited to shower cleansers, shower gels, body shampoos, hand/body/facial cleansers, abrasive scrub cleansing products, astringent cleansers, makeup cleansers, liquid soaps, toilet soap bars, syndet bars and the like.

Examples of skin care products include, but are not limited to hand/body/facial moisturizers, hand/body/facial creams, massage creams, hand/body/facial lotions, sunscreen products, tanning products, self-tanning products, aftersun products, masking products, lipsticks, lip gloss products, rejuvenating products, antiaging products, antiwrinkle products, anticellulite products, antiacne products and the like.

Examples of shaving products include, but are not limited to shaving creams, aftershave products, preshave products and the like.

Examples of deodorant/antiperspirant products include, but are not limited to deodorant products, antiperspirant products and the like.

A classification according to product form would consist of aersols, liquids, gels, creams, lotions, sprays, pastes, roll-on, stick, tablet, powdered and bar form. Preferred are the gel, creme (cream) and liquid forms.

Industrial Application and Use

The heteroatom containing alkyl aldonamide compounds of the invention are useful as surfactants that may be used alone or in combination with other surfactants to provide improved foam, viscosity, clarity and conditioning characteristics. More specifically, the heteroatom containing alkyl aldonamide compounds of the invention are useful as foam stabilizing agents, thickening agents, solubilizing agents and skin conditioning agents. In addition, it has been found that the heteroatom containing alkyl aldonamide compounds of the invention are also useful as gelling agents, foam boosting agents, detergency enhancing agents, soil release agents, lime soap dispersants, wetting agents and stabilizing agents. Furthermore, certain long chain heteroatom containing alkyl aldonamide compounds of the invention wherein the alkyl group contains 12 carbons or more ($Kf>600°$ C.) were found to be useful as pearlescent agents (opacifiers), suspending agents, emollients (moisturizers/humectants) and emulsifying agents.

The non-heteroatom containing alkyl aldonamide compounds of the invention wherein the alkyl group contains 10 carbons or more have poor water solubility ($Kf>60°$ C.) and were found to be useful as pearlescent agents (opacifiers) and suspending agents.

Home Application and Use

The present compositions are used in a conventional manner for cleaning and/or conditioning the skin. From about 0.1 g to about 15 g of a composition is applied to the skin that may or may not be thoroughly wetted with water. The composition is worked unto the skin from about 30 seconds to about five minutes and then rinsed off or left on.

The following Examples further describe and demonstrate the preferred embodiments that are within the scope of the present invention. The Examples are given solely for the purpose of illustration and are not to be construed as being limiting to the present invention since many variations are possible without departing from the spirit and scope of the invention.

EXAMPLES

Analysis of Monosaccharide Aldonamides by Gas Chromatography

Gas chromatography was found to be a convenient method for the examination of monosaccharide aldonamide compounds. The method of persilylation with hexamethyldisilazane (HMDS) and trimethylchlorosilane (TMCS) in pyridine is the simplest way for producing sufficiently stable and volatile derivatives for analysis. The mixture of both agents are more reactive than either reagent alone, and the by-products combine to form neutral ammonium chloride ($NH_4Cl$) or pyridine hydrochloride ($C_5H_5N \cdot HCl$).

The purity of several monosaccharide aldonamides were determined and found to be 97–99.9%. All products were well separated from starting materials, however aldonamides with alkyl chains containing eighteen carbons or more were not volatile enough for analysis.

Approximately 7–10 mg of a monosaccharide aldonamide compound was treated with 1 ml of sil-prep reagent (pyridine:HMDS:TMCS=9:3:1) in a 1 dram stoppered vial containing a magnetic stirring bar. The mixture was stirred vigorously at room temperature for about a hour or longer prior to chromatography. The solution became cloudy owing to precipitation of $NH_4Cl$ and $C_5H_5N \cdot HCl$ which was filtered through a CAMEO II 25 mm filter. From about 1.0 μl to about 1.1 μl of the resulting mixture was injected into the gas chromatograph.

All gas chromatography was conducted on a Hewlett Packard 5890 Series II Gas Chromatograph. All sample components were detected by a flame ionization detector using a split ratio of 100:1 and separated on a crosslinked 5% phenylmethyl silicone capillary column 25 m×0.32 mm'0.53 μm. The carrier gas was helium at 1 ml/minute and the temperature program was 3 minutes at 140° C. then 30° C./minute to 250° C. for 75 minutes.

Example 1 (No Heteroatom)

Preparation of Dodecyl D-Ribonamide (Used for Comparative Purposes)

A 200 ml four necked round bottom flask equipped with a condenser, addition funnel, thermometer and mechanical stirrer was charged with D-ribono-1,4-lactone (15.0 g, 0.10 mole) and methanol (45 g, for 43% total solids). The suspension was heated to 40°–43° C. for 15 minutes and the heating mantle removed. Dodecylamine (18.8 g, 0.10 mole) containing methanol (5 ml) was added dropwise over ½ hour. The reaction mixture was allowed to cool to room temperature (about 21° C.) followed by stirring overnight to allow complete crystallization. The white product was filtered, washed with methanol (3×20 ml) and dried under vacuum at 40°–45° C. giving 31.5 g (93% yield) of dodecyl D-ribonamide with a melting point of 101°–102° C. and 99.9% purity.

Example 2 (No Heteroatom)

Preparation of Coco D-Gluconamide (Used for Comparative Purposes)

A 5 liter four necked round bottom flask equipped with a condenser, addition funnel, thermometer and mechanical stirrer was charged with D-glucono-1,5-lactone (480.0 g, 2.69 moles) and methanol (2752 g, for 27% total solids). The suspension was heated to 40°–50° C. for 15 minutes and the heating mantle removed. Cocoamine (538.0 g, 2.69 moles) containing methanol (80 ml) was added dropwise over ½ hour. The reaction mixture was allowed to cool to room temperature (about 21° C.) followed by stirring overnight to allow complete crystallization. The white product was filtered, washed with methanol (3×500 ml) and dried under vacuum at 40°–45° C. giving 947.0 g (93% yield) of coco D-gluconamide with a melting point of 147°–148° C.

Examples 3–22 (No Heteroatom)

The monosaccharide alkyl aldonamides (Examples 3–22) in Table 1 were prepared in a similar manner as in Example 2.

TABLE 1

Monosaccharide Alkyl Aldonamides
(Compounds Without Heteroatom for Comparative Purposes)

| Example | Structure | Attached Hydrocarbon | MP (°C.) | % Yield | % Purity |
|---|---|---|---|---|---|
| 3 | HOCH$_2$CHCHCHCHCNH— with OH, OH, OH, OH and C=O (D-Gluconamide) | C$_7$H$_{15}$ | 159–160 | 93 | 99.7 |
| 4 | D-Gluconamide | C$_8$H$_{17}$ | 159–160 | 90 | 99.9 |
| 5 | D-Gluconamide | C$_9$H$_{19}$ | 158–159 | 92 | 99.9 |
| 6 | D-Gluconamide | C$_{10}$H$_{21}$ | 157–158 | 91 | 99.9 |
| 7 | D-Gluconamide | C$_{11}$H$_{23}$ | 156–157 | 92 | 99.9 |
| 8 | D-Gluconamide | C$_{12}$H$_{25}$ | 155–156 | 96 | 99.9 |
| 9 | L-Gluconamide | C$_{12}$H$_{25}$ | 154–155 | 95 | 99.9 |
| 10 | D-Gluconamide | C$_{13}$H$_{27}$ | 155–156 | 95 | 99.9 |
| 11 | D-Gluconamide | C$_{14}$H$_{29}$ | 154–155 | 92 | 97.4 |
| 12 | D-Gluconamide | C$_{16}$H$_{33}$ | 152–153 | 94 | 99.9 |
| 13 | D-Gluconamide | C$_{18}$H$_{37}$ | 147–149 | 94 | — |
| 14 | D-Gluconamide | Tallow | 141–142 | 91 | — |
| 15 | D-Gluconamide | Soya | 135–137 | 86 | — |
| 16 | D-Gluconamide | Oleyl | 130–131 | 86 | — |
| 17 | HOCH$_2$CHCHCHCHCNH— with OH, OH, OH, OH and C=O (D-Galactonamide) | C$_{12}$H$_{25}$ | 187–188 (d) | 93 | 99.8 |
| 18 | HOCH$_2$CHCHCHCHCNH— with OH, OH, OH, OH and C=O (L-Galactonamide) | C$_{12}$H$_{25}$ | 187–188 (d) | 95 | 99.7 |
| 19 | HOCH$_2$CHCHCHCHCNH— with OH, OH, OH, OH and C=O (L-Mannonamide) | C$_{12}$H$_{25}$ | 159–160 | 95 | 99.6 |
| 20 | HOCH$_2$CHCHCHCHCHCNH— with OH, OH, OH, OH, OH and C=O (D-Glycero-L-Mannoheptonamide) | C$_{12}$H$_{25}$ | 195–197 (d) | 97 | 98.6 |
| 21 | HOCH$_2$CHCHCHCHCHCNH— with OH, OH, OH, OH, OH and C=O (D-Glucoheptonamide) | C$_{12}$H$_{25}$ | 156–157 | 93 | 99.9 |
| 22 | HOCH$_2$CHCHCHCHCHCHCNH— with OH, OH, OH, OH, OH, OH and C=O (D-Glucooctonamide) | C$_{12}$H$_{25}$ | 156–157 | 93 | 99.9 | d = decomposition occurred during melting.

Example 23 (1 Ether Heteroatom)

Preparation of Octyl/Decyloxypropyl D-Ribonamide

A 250 ml four necked round bottom flask equipped with a condenser, additional funnel, thermometer and mechanical stirrer was charged with ribono-1,4-lactone (10.0 g, 0.07 mole) and methanol (37 g for 40% total solids). The suspension was heated to 40°–50° C. for 15 minutes and heating mantle removed. Octyl/decyloxypropylamine (14.6 g, 0.07 mole) was added dropwise over ½ hour and the reaction mixture stirred for six hours. The white product was filtered, washed with cold acetone (3×10 ml) and dried under vacuum at 40°–45° C. giving 14.0 g (57% yield) of octyl/decyloxypropyl D-ribonamide with a melting point of 71°–72° C. and 98.7% purity (62.8%/35.9%:$C_8$/$C_{10}$).

Examples 24–34 (1 Ether Heteroatom)

The monosaccharide alkyloxypropyl aldonamides (Examples 24–34) in Table 2 were prepared in a similar manner as in Example 23.

Example 36 (1 Ester Heteroatom)

Preparation of N-D-Gluconyl Dodecyl Glycinate

A 100 ml round bottom flask equipped with a condenser, addition funnel, thermometer and mechanical stirrer was charged with D-glucono-1,5-lactone (5.0 g, 0.03 mole) and isopropanol (35 g). The suspension was heated to 50° C. over 15 minutes. A mixture of glycine dodecyl ester p-toluenesulfonate salt (11.7 g, 0.03 mole), triethylamine (2.9 g 0.03 mole) and isopropanol (20 g) were added dropwise over 15 minutes from an addition funnel. The reaction mixture was stirred rapidly for about 2 hrs and then cooled to room temperature. The white product was filtered, washed with chloroform (3×150 ml) and dried under high vacuum at 35° C. giving 7.2 g (61% yield) of N-D-gluconyl dodecyl glycinate with a melting point of 121°–122° C. and 98.6% purity.

Example 37 (1 Ester Heteroatom)

Preparation of N-D-Gluconyl Dodecyl Ester of Ethanolamine

A 100 ml round bottom flask equipped with a condenser, addition funnel, thermometer and mechanical stirrer was

TABLE 2

Monosaccharide Alkyloxypropyl Aldonamides

| Example | Structure | Attached Hydrocarbon | MP (°C.) | % Yield | % Purity |
|---|---|---|---|---|---|
| 24 | HOCH$_2$CHCHCHCHCNH— with OH, OH, OH, OH, O substituents (D-Gluconamide) | $C_3H_6OCH_2CHC_4H_9$ with $C_2H_5$ | 89–90 | 73 | 99.9 |
| 25 | D-Gluconamide | $C_3H_6OC_8H_{17}$/$C_{10}H_{21}$ | 119–120 | 83 | 63.7/35.6 |
| 26 | D-Gluconamide | $C_3H_6O$-Isodecyl | 96–101 | 83 | — |
| 27 | D-Gluconamide | $C_3H_6OC_{12}H_{25}$ | 129–130 | 96 | 99.5 |
| 28 | D-Gluconamide | $C_3H_6O$-Isotridecyl | 81–86 | 74 | — |
| 29 | D-Gluconamide | $C_3H_6OC_{12}H_{25}$ to $C_{15}H_{31}$ | 125–126 | 82 | — |
| 30 | D-Gluconamide | $C_3H_6OC_{14}H_{29}$ | 129–130 | 86 | 99.7 |
| 31 | HOCH$_2$CHCHCHCHCHCNH— with OH, OH, OH, OH, OH, O substituents (D-Glucoheptonamide) | $C_3H_6OC_8H_{17}$/$C_{10}H_{21}$ | 129–130 | 88 | 66.2/33.6 |
| 32 | D-Glucoheptonamide | $C_3H_6O$-Isodecyl | 100–105 | 85 | — |
| 33 | D-Glucoheptonamide | $C_3H_6OC_{12}H_{25}$ | 133–134 | 89 | 99.9 |
| 34 | D-Glucoheptonamide | $C_3H_6OC_{12}H_{25}$ to $C_{15}H_{31}$ | 128–129 | 75 | — |

Example 35 (1 Ether Heteroatom)

Preparation of Octyl/Decyloxypropyl D-Glyceramide (No Solvent)

A 50 ml four necked round bottom flask equipped with a condenser, additional funnel, thermometer and mechanical stirrer was charged with methyl glycerate (5.1 g, 0.04 mole) and octyl/decyloxypropylamine (8.0 g, 0.04 mole). The reaction mixture was heated to 65° C. for 24 hours. Isopropanol was added and the product was recrystallized, filtered, washed with cold isopropanol (3×5 ml) and dried under vacuum at 40°–45° C. giving 3.4 g (29% yield) of octyl/decyloxypropyl D-glyceramide.

charged with D-glucono-1,5-lactone (7.0 g, 0.04 mole) and isopropanol (30 g). The suspension was heated to 65° C. over 15 minutes. A mixture of dodecyl ester of monoethanolamine p-toluenesulfonate salt (16.3 g, 0.04 mole), triethylamine (4.0 g 0.04 mole) and isopropanol (20 g) were added dropwise over 15 minutes from an addition funnel. The reaction mixture was stirred rapidly for about 6 hrs and then cooled to room temperature. The white product was filtered, washed with chloroform (3×150 ml) and dried under high vacuum at 35° C. giving 13.3 g (810/5 yield) of N-D-gluconyl dodecyl ester of ethanolamine with a melting point of 142°–143° C. and 97.4% purity.

Example 38 (1 Ester Heteroatom)

Preparation of N-D-Gluconyl Dodecyl DL-Alaninate

A 100 ml round bottom flask equipped with a condenser, addition funnel, thermometer and mechanical stirrer was charged with D-glucono-1,5-lactone (7.0 g, 0.04 mole) and isopropanol (30 g). The suspension was heated to 60° C. over 15 minutes. A mixture of DL-alanine dodecyl ester p-toluenesulfonate salt (16.9 g, 0.04 mole), triethylamine (4.0 g 0.04 mole) and isopropanol (20 g) were added dropwise over 15 minutes from an addition funnel. The reaction mixture was stirred rapidly for about 6 hrs and then cooled to room temperature. The white product was filtered, washed with chloroform (3×150 ml) and dried under high vacuum at 35° C. giving 12.5 g (73% yield) of N-D-gluconyl dodecyl alaninate with a melting point of 97°–98° C. and 98.8% purity.

Example 39 (1 Ester and 2 Ether Heteroatoms)

Preparation of N-D-Gluconyl Dodecyldi(oxyethyl) Glycinate

A 100 ml round bottom flask equipped with a condenser, addition funnel, thermometer and mechanical stirrer was charged with D-glucono-1,5-lactone (7.0 g, 0.04 mole) and isopropanol (30 g). The suspension was heated to 60° C. over 15 minutes. A mixture of glycine dodecyldi(oxyethyl) ester p-toluenesulfonate salt (20.2 g, 0.04 mole), triethylamine (4.0 g 0.04 mole) and isopropanol (20 g) were added dropwise over 15 minutes from an addition funnel. The reaction mixture was stirred rapidly for about 8 hrs and then cooled to room temperature. The white product was filtered, washed with chloroform (3×150 ml) and dried under high vacuum at 35° C. giving 8.9 g (43% yield) of N-D-gluconyl dodecyldi(oxyethyl) glycinate.

Example 40 (1 Amino Heteroatom)

Preparation of Cocoaminopropyl D-Gluconamide

A 1 liter round bottom flask equipped with a condenser, addition. funnel, thermometer and mechanical stirrer was charged with D-glucono-1,5-lactone (100.0 g, 0.56 mole) and methanol (208 g for 55% total solids). The suspension was heated to 40° C. over 15 minutes and the heating mantle removed. Cocoaminopropylamine (153.8 g, 0.56 mole) was added dropwise over 15 minutes with rapid stirring. The reaction mixture was cooled and placed in a refrigerator at 0° C. overnight. The white product was filtered, washed with cold isopropanol (3×100 ml) and dried under high vacuum at 35° C. giving 206.0 g (81% yield) of cocoaminopropyl D-gluconamide with a melting point of 109°–111° C.

Example 41 (1 Amino Heteroatom)

Preparation of Hydrogenated Tallowaminopropyl D-Gluconamide

A 1 liter round bottom flask equipped with a condenser, addition funnel, thermometer and mechanical stirrer was charged with D-glucono-1,5-lactone (20.0 g, 0.11 mole) and methanol (56 g). The suspension was heated to 40° C. over 15 minutes and the heating mantle removed. Hydrogenated tallowaminopropylamine (36.0 g, 0.11 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 46.2 g (83% yield) of hydrogenated tallowaminopropyl D-gluconamide with a melting point of 112°–115° C.

Example 42 (1 Amino Heteroatom)

Preparation of Soyaaminopropyl D-Gluconamide

A 100 ml round bottom flask equipped with a condenser, addition funnel, thermometer and mechanical stirrer was charged with D-glucono-1,5-lactone (5.4 g, 0.03 mole) and methanol (7 g). The suspension was heated to 40° C. over 15 minutes and the heating mantle removed. Soyaaminopropylamine (10.0 g, 0.03 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 14.1 g (92% yield) of soyaaminopropyl D-gluconamide with a melting point of 97°–100° C.

Example 42b (1 Amino Heteroatom)

Preparation of Oleylaminopropyl D-Gluconamide

A 500 ml round bottom flask equipped with a condenser, addition. funnel, thermometer and mechanical stirrer was charged with D-glucono-1,5-lactone (25.0 g, 0.14 mole) and methanol (31 g). The suspension was heated to 40° C. over 15 minutes and the heating mantle removed. Oleylaminopropylamine (47.7 g, 0.14 mole) was added dropwise over 10 minutes and the reaction stirred for 6 hours. Acetone (300 ml) was added and the flask placed in a refrigerator overnight. The white solid was filtered, washed with cold acetone (3×50 g) and dried under vacuum at 35° C. giving 65.0 g (89% yield) of oleylaminopropyl D-gluconamide with a melting point of 100° C.–103° C.

Examples 43–44 (1 Amino and 1 Ether Heteroatom)

The monosaccharide alkyloxypropylaminopropyl aldonamides (Examples 43–44) in Table 3 were prepared in a similar manner as in Example 42.

TABLE 3

Monosaccharide Alkyloxypropylaminopropyl Aldonamides

| Example | Structure | Attached Hydrocarbon | MP (°C.) | % Yield |
|---------|-----------|----------------------|----------|---------|
| 43 | OH O<br>　\|　\|\|<br>HOCH$_2$CHCHCHCHCNH—<br>　　\|　\|　\|<br>　　OH OH　OH<br><br>D-Gluconamide | C$_3$H$_6$NHC$_3$H$_6$O-Isotridecyl | 70–77 | 84 |
| 44 | D-Gluconamide | C$_3$H$_6$NHC$_3$H$_6$OC$_{12}$H$_{25}$ to C$_{15}$H$_{31}$ | 91–95 | 87 |

Example 45 (1 Amide Heteroatom)

Preparation of Hexylamido-2-Methylpentyl D-Gluconamide and Hexylamido-4-Methylpentyl D-Gluconamide

A 100 ml round bottom flask equipped with a condenser, addition funnel, thermometer and mechanical stirrer was charged with D-glucono-1,5-lactone (6.7 g, 0.04 mole) and isopropanol (35 g). The suspension was heated to 50° C. over 25 minutes and the heating mantle removed. A mixture of hexylamido-2-methylpentylamine and hexylamido-4-methylpentylamine (45%/55%, 8.0 g, 0.04 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 7.6 g (52% yield) of hexylamido-2-methylpentyl D-gluconamide and hexylamido-4-methylpentyl D-gluconamide.

Example 46 (1 Amide and 1 Ether Heteroatom)

Preparation of Dodecyl to Pentadecyloxypropylacetamidopropyl D-Gluconamide

A 50 ml round bottom flask equipped with a condenser, addition funnel, thermometer and mechanical stirrer was charged with dodecyl to pentadecyloxypropylaminopropyl D-gluconamide (1.0 g, 2.93×10$^{-3}$ mole) and methanol (5 g). The suspension was heated to 40° C. and acetic anhydride (1.2 g, 1.18×10$^{-2}$ mole) was added dropwise over 15 minutes with rapid stirring. The reaction mixture was heated at 40° C. for 48 hours and the solvent, acetic acid and excess anhydride was removed by vacuum distillation (1.1 g, 98% yield). Water was added (3.6 g) to the reaction mixture and the product neutralized to a pH of about 7 with 0.1N sodium hydroxide solution. Hydrogen peroxide 3% (0.5 ml) was added and the product stirred for several hours. The sample is a pureable liquid ready for formulation.

Example 47 (1 Amide and 1 Ether Heteroatom)

Preparation of Dodecyl to Pentadecyloxypropylpropionamidopropyl D-Gluconamide

A 50 ml round bottom flask equipped with a condenser, addition funnel, thermometer, pH meter and mechanical stirrer was charged with dodecyl to pentadecyloxypropylaminopropyl D-gluconamide (1.0 g, 2.93×10$^{-3}$ mole) and water (4.0 g). Propionic anhydride (0.95 g, 7.33×10$^{-3}$ mole) is added portionwise along with 1N sodium hydroxide (which is added to maintain a pH of 7) at room temperature (21° C.). The mixture was stirred for 24 hours at room temperature and hydrogen peroxide 3% (0.5 ml) was then added. The sample is a pureable liquid ready for formulation.

Example 48 (1 Amide and 1 Ether Heteroatom)

Preparation of Dodecyl to Pentadecyloxypropyltrifluoroacetamidopropyl D-Gluconamide

A 50 ml plastic beaker equipped with an addition funnel, thermometer and stir bar was charged with dodecyl to pentadecyloxypropylaminopropyl D-gluconamide (1.0 g, 2.93×10$^{-3}$ mole) and methanol (15 g). The suspension was heated to 25° C. and trifloroacetic anhydride (1.2 g, 5.86×10$^{-3}$ mole) was added dropwise over 15 minutes with rapid stirring. The reaction mixture was stirred at room temperature for 8 hours and the solvent, trifluoroacetic acid and excess anhydride was removed by nitrogen sparge (1.4 g). Water (4.6 g) was added to the reaction mixture and the solution neutralized to a pH of about 7 with 0.1N sodium hydroxide solution. Sodium borohydride (0.03 g) was added and the product stirred for several hours. The sample is a pureable liquid ready for formulation.

Example 49 (1 Amide and 1 Ether Heteroatom)

Preparation of Dodecyl to Pentadecyloxypropylcaproamidopropyl D-Gluconamide

A 50 ml round bottom flask equipped with a condenser, addition funnel, thermometer and mechanical stirrer was charged with dodecyl to pentadecyloxypropylaminopropyl D-gluconamide (2.0 g, 5.86×10$^{-3}$ mole) and methanol (30 g). A separate 50 ml round bottom flask equipped with a stir bar and nitrogen blanket was charged with caproic acid (0.68 g, 5.86×10$^{-3}$ mole), triethylamine (0.60 g, 5.86×10$^{-3}$ mole) and diethyl ether (10 g). This mixture was stirred at 0° C. and ethyl chloroformate (0.64 g, 5.91×10$^{-3}$ mole) was added rapidly. After about 0.5 hour the resulting ethyl hydrogen carbonate caproic anhydride was filtered, washed with ether (3 ml) and added to methanolic solution containing dodecyl to pentadecyloxypropylaminopropyl D-gluconamide. The reaction mixture was stirred at 40° C. for 2 hours and the solvent was removed by vacuum distillation (2.3 g 91% yield). Water was added to the reaction mixture and the solution neutralized to a pH of about 7 with 0.1N sodium hydroxide solution. About 0.5 ml of 3% hydrogen peroxide was added and the product stirred for several hours. The sample is a pureable liquid ready for formulation.

Example 50 (1 Amide and 1 Ether Heteroatom)

Preparation of Dodecyl to Pentadecyloxypropylpropionamidopropyl D-Lactobionamide A 50 ml round bottom flask equipped with a condenser, addition funnel, thermometer and mechanical stirrer was charged with dodecyl to pentadecyloxypropylaminopropyl D-lactobionamide (3.0 g, 4.40×10$^{-3}$ mole) and methanol (20 g). The suspension was heated to 35° C. and propionic anhydride (1.7 g, 1.32×10$^{-2}$ mole) was added dropwise over 15 minutes with rapid stirring. The reaction mixture was heated at room temperature for 24 hours and the solvent, propionic acid and excess anhydride was removed by vacuum distillation (3.1 g, 95% yield).

Example 51 (1 Amide Heteroatom)

Preparation of Cocolauramidopropyl D-Lactobionamide

A 250 ml round bottom flask equipped with a condenser, addition funnel, thermometer and mechanical stirrer was charged with cocoaminopropyl D-lactobionamide (15.8 g, 2.57×10$^{-2}$ mole), methanol (200 ml) and lauric anhydride (15.0 g, 3.92×10$^{-2}$ mole). The mixture was stirred and heated at 50° C. for several hours, then at room temperature for several days. The solvent was removed by rotaevaporation and the mixture slurried with ethyl acetate (100 ml), filtered and washed with ethyl acetate (2×90 ml) followed by air drying. The solid residue was then extracted with butanol (400 ml) and acidic water (400 ml). The butanol layer was separated and extracted with water (2×200 ml) containing sodium chloride followed by drying over magnesium sulfate. The dry butanol layer was filtered and washed with additional butanol (2×50 ml) which was removed by vacuum distillation giving 9.7 g (48% yield) of cocolauramidopropyl D-lactobionamide

Example 52 (No Heteroatom)

Preparation of Nonyl D-Lactobionamide (Used for Comparative Purposes)

A 100 ml round bottom flask equipped with a condenser, addition funnel, thermometer and mechanical stirrer was charged with D-lactobiono-1,5-lactone (100.0 g, 0.29 mole) and methanol (300 g). The suspension was heated to 50° C. over 15 minutes. Nonylamine (39.1 g, 0.27 mole) was added dropwise over 15 minutes with rapid stirring. The reaction mixture was cooled to room temperature and stirred overnight. The product was filtered, washed with cold methanol (1×100 ml) and dried under vacuum at 35° C. The product was then recrystallized in methanol giving 110.0 g (84% yield) of nonyl D-lactobionamide with a melting point of 149°–150° C.

Examples 53–66 (No Heteroatom)

The disaccharide alkyl aldonamides (Examples 53–66) in Table 4 were prepared in a similar manner as in Example 52.

TABLE 4

Disaccharide Alkyl Aldobionamides
(Compounds Without Heteroatom Used for Comparative Purposes)

| Example | Structure | Attached Hydrocarbon | MP (°C.) | % Yield | % Purity (HPLC) |
|---|---|---|---|---|---|
| 53 | D-Lactobionamide | $C_{10}H_{21}$ | 138–139 | 47 | 99.0 |
| 54 | D-Lactobionamide | $C_{11}H_{23}$ | 147–148 | 34 | 99.2 |
| 55 | D-Lactobionamide | $C_{12}H_{25}$ | 137–138 | 35 | 99.3 |
| 56 | D-Lactobionamide | $C_{13}H_{27}$ | 147–148 | 36 | 99.9 |
| 57 | D-Lactobionamide | $C_{14}H_{29}$ | 126–127 | 92 | 97.4 |
| 58 | D-Lactobionamide | $C_{15}H_{31}$ | 147–148 | 70 | 99.3 |
| 59 | D-Lactobionamide | $C_{16}H_{33}$ | 130–131 | 60 | 99.3 |
| 60 | D-Lactobionamide | $C_{18}H_{37}$ | 112–113 | 92 | — |
| 61 | D-Lactobionamide | Tallow | 109–111 | 65 | 97.5 |
| 62 | D-Lactobionamide | Oleyl | 104–106 | 71 | — |
| 63 | D-Maltobionamide | $C_{11}H_{23}$ | 109–110 | 26 | 99.7 |
| 64 | D-Maltobionamide | $C_{12}H_{25}$ | 114–115 | 26 | 99.7 |
| 65 | D-Maltobionamide | $C_{14}H_{29}$ | 118–119 | 31 | 99.7 |
| 66 | D-Maltobionamide | $C_{16}H_{33}$ | 122–123 | 67 | 98.0 |

Example 67 (1 Ether Heteroatom)

Preparation of Octyl/Decyloxypropyl D-Lactobionamide

A 2 liter round bottom flask equipped with a condenser, addition funnel, thermometer and mechanical stirrer was charged with D-lactobion-1,5-lactone (84.1 g, 0.25 mole), methanol (250 g for 35% total solids) and methanesulfonic acid (3 drops). The suspension was heated to 50° C. over 15 minutes and the heating mantle removed. Octyl/decyloxypropylamine (50.0 g, 0.25 mole) was added dropwise over 15 minutes with rapid stirring. The reaction mixture was cooled and stirred at room temperature overnight with 30% hydrogen peroxide (1 ml). Methanol was removed by vacuum distillation and acetone (1000 ml) added. The white product was filtered, washed with cold acetone (3×250 ml) and dried under high vacuum at 35° C. giving 112.2 g (84% yield) of octyl/decyloxypropyl D-lactobionamide with a melting point of 99°–101° C.

Example 68 (1 Ether Heteroatom)

Preparation of Dodecyloxypropyl D-Lactobionamide

A 3 liter round bottom flask equipped with a condenser, addition funnel, thermometer and mechanical stirrer was charged with D-lactobiono-1,5-lactone (180.0 g, 0.53 mole) and methanol (1100 ml). The suspension was heated to 50° C. over 15 minutes and the heating mantle removed. Dodecyloxypropylamine (128.8 g, 0.53 mole) was added dropwise over 30 minutes with rapid stirring. The reaction mixture was cooled and stirred at room temperature overnight. The white product was filtered, washed with cold acetone (2×400 ml) and dried under high vacuum at 40° C. giving 224.5 g (73% yield) of dodecyloxypropyl D-lactobionamide with a melting point of 117°–118° C.

Example 69 (1 Ether Heteroatom)

Preparation of Dodecyloxypropyl D-Maltobionamide

A 100 mi round bottom flask equipped with a condenser, addition funnel, thermometer and mechanical stirrer was charged with D-maltobiono-1,5-lactone (6.0 g, 0.02 mole)

and methanol (25 ml). The suspension was heated to 50° C. over 15 minutes and the heating mantle removed. Dodecyloxypropylamine (4.3 g, 0.02 mole) was added dropwise over 30 minutes with rapid stirring. Acetone (50 ml) was added and the reaction mixture stirred at room temperature overnight. The white product was filtered, washed with cold acetone (3×30 ml) and dried under high vacuum at 30° C. giving 5.9 g (57% yield) of dodecyloxypropyl D-maltobionamide.

Example 70 (1 Ether heteroatom)

Preparation of Dodecyl to Pentadecyloxypropyl D-Lactobionamide

A 2 liter round bottom flask equipped with a condenser, addition funnel, thermometer and mechanical stirrer was charged with D-lactobion-1,5-lactone (65.2 g, 0.19 mole), methanol (214 g for 30% total solids) and methanesulfonic acid (3 drops). The suspension was heated to 50° C. over 15 minutes and the heating mantle removed. Dodecyl to pentadecyloxypropylamine (50.0 g, 0.19 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 98.7 g (86% yield) of dodecyl to pentadecyloxypropyl D-lactobionamide with a melting point of 95°–98° C.

Example 71 (1 Ether Heteroatom)

Preparation of Tetradecyloxypropyl D-Lactobionamide

A 5 liter round bottom flask equipped with a condenser, addition funnel, thermometer and mechanical stirrer was charged with D-lactobiono-1,5-lactone (500.0 g, 1.47 moles) and methanol (3000 ml). The suspension was heated to 50° C. over 30 minutes and the heating mantle removed. Tetradecyloxypropylamine (401.7 g, 1.47 mole) was added dropwise over 30 minutes with rapid stirring. The reaction mixture was cooled and stirred at room temperature overnight. The white product was filtered, washed with cold acetone (2×700 ml) and dried under high vacuum at 40° C. giving 656.1 g (73% yield) of tetradecyloxypropyl D-lactobionamide.

Example 72 (1 Ester Heteroatom)

Preparation of N-D-Lactobionyl Dodecyl Glycinate

A 50 ml round bottom flask equipped with a condenser, thermometer and mechanical stirrer was charged with dodecyl glycinate hydrochloride (9.0 g, 0.03 mole) and 2.0M methanolic ammonia (16 ml, 0.03 mole). The mixture was stirred at room temperature for 10 minutes and lactobiono-1,5-lactone (10.9 g, 0.03 mole) added followed by heating at reflux for 1 hour. Activated charcoal was then added and the reaction mixture stirred for 15 minutes at reflux. Activated charcoal was removed by filtration over a bed of celite while warm, washed with methanol (3×50 ml) and the filtrate allowed to cool to room temperature. The solvent was removed by rotary evaporation, the product washed with ethyl ether (2×100 ml), filtered and dried in a vacuum oven at room temperature over phosphorous pentoxide giving 14.0 g (75% yield) of N-D-lactobionyl dodecyl glycinate.

Example 73 (1 Ester Heteroatom)

Preparation of N-D-Lactobionyl Dodecyl β-Alaninate

A 25 ml round bottom flask equipped with a condenser, thermometer and stir bar was charged with dodecyl β-alaninate hydrochloride (3.0 g, 0.01 mole) and 2.0M methanolic ammonia (5 ml, 0.01 mole). The mixture was stirred at room temperature for 10 minutes and lactobiono-1,5-lactone (3.5 g, 0.01 mole) added followed by heating at reflux for 1 hour. Activated charcoal was then added and the reaction mixture stirred for 15 minutes at reflux. Activated charcoal was removed by filtration over a bed of celite while warm, washed with methanol (3×25 ml) and the filtrate allowed to cool to room temperature. The solvent was removed by rotary evaporation, the product washed with ethyl ether (2×50 ml), filtered and dried in a vacuum oven at room temperature over phosphorous pentoxide giving 4.3 g (70% yield) of N-D-lactobionyl dodecyl β-alaninate.

Example 74 (1 Amino Heteroatom)

Preparation of Cocoaminopropyl D-Lactobionamide

A 2 liter round bottom flask equipped with a condenser, addition funnel, thermometer and mechanical stirrer was charged with D-lactobion-1,5-lactone (66.4 g, 0.20 mole), methanol (175 g for 40% total solids) and methanesulfonic acid (3 drops). The suspension was heated to 50° C. over 15 minutes and the heating mantle removed. Cocoaminopropylamine (50.0 g, 0.20 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 96.9 g (83% yield) of cocoaminopropyl D-lactobionamide with a melting point of 97°–101° C.

Example 75 (1 Amino Heteroatom)

Preparation of Oleylaminopropyl D-Lactobionamide

A 2 liter round bottom flask equipped with a condenser, addition funnel, thermometer and mechanical stirrer was charged with D-lactobion-1,5-lactone (52.7 g, 0.15 mole), methanol (103 g for 50% total solids) and methanesulfonic acid (4 drops). The suspension was heated to 50° C. over 15 minutes and the heating mantle removed. Oleylaminopropylamine (50.0 g, 0.15 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 93.1 g (91% yield) of oleylaminopropyl D-lactobionamide with a melting point of 117°–118° C.

Example 76 (1 Amino Heteroatom)

Preparation of Hydrogenated Tallowaminopropyl D-Lactobionamide

A 1 liter round bottom flask equipped with a condenser, addition funnel, thermometer and mechanical stirrer was charged with D-lactobiono-1,5-lactone (20.0 g, 0.06 mole) and methanol (50 g). The suspension was heated to 40° C. over 15 minutes and the heating mantle removed. Hydrogenated tallowaminopropylamine (19.0 g, 0.06 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35°

C. giving 46.2 g (84% yield) of hydrogenated tallowaminopropyl D-lactobionamide with a melting point of 135°–137° C.

Example 77 (1 Amino and 1 Ether Heteroatom)

Preparation of Dodecyl to Pentadecyloxypropylaminopropyl D-Lactobionamide

A 2 liter round bottom flask equipped with a condenser, addition funnel, thermometer and mechanical stirrer was charged with D-lactobion-1,5-lactone (53.6 g, 0.16 mole), methanol (104 g for 50% total solids) and methanesulfonic acid (3 drops). The suspension was heated to 50° C. over 15 minutes and the heating mantle removed. Dodecyl to pentadecyloxypropylaminopropylamine (50.0 g, 0.16 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 91.3 g (88% yield) of dodecyl to pentadecyloxypropylaminopropyl D-lactobionamide with a melting point of 107°–111° C.

Example 78 (6 Ether Heteroatoms)

Preparation of Dodecyl to Pentadecyloxypropyl D-Gluconamide Pentaoxyethylene ether A 100 g autoclave equipped with a pressure gauge, mechanical stirrer, rupture disk, gas inlet and gas outlet was charged with dodecyl to pentadecyloxypropyl D-gluconamide (7.0 g, 1.60×10$^{-2}$ mole) dissolved in dimethylformamide (30 g) and potassium hydroxide (0.04 g, 8.0×10$^{-4}$ mole). The autoclave was flushed with a blanket of nitrogen and a mild vacuum pulled. Ethylene oxide (3.5 g, 8.0×10$^{-2}$ mole) was then added and the mixture heated to 70° C.–100° C. for seven hours. The mixture was then cooled and discharged into a 100 ml round bottom flask equipped with a distillation head, thermometer and mechanical stirrer containing 30% hydrogen peroxide (0.5 ml). The mixture was stirred for several hours at 300° C. and then neutralized with 0.1N hydrochloric acid followed by removal of dimethylformamide by vacuum distillation giving 10.7 g of dodecyl to pentadecyloxypropyl D-gluconamide pentaoxyethylene ether.

Example 79 (5 Ether Heteroatoms)

Preparation of Dodecyloxypropyl D-Maltobionamide Tetraoxyethylene ether

A 100 g autoclave equipped with a pressure gauge, mechanical stirrer, rupture disk, gas inlet and gas outlet was charged with dodecyl oxypropyl D-maltobionamide (4.5 g, 7.49×10$^{-3}$ mole) dissolved in tert-butanol (20 g) and triethylamine (0.45 g, 4.45×10$^{-3}$ mole). The autoclave was flushed with a blanket of nitrogen and a mild vacuum pulled. Ethylene oxide (1.3 g, 3.0×10$^{-2}$ mole) was then added and the mixture heated to 70° C.–80° C. for seven hours. The mixture was then cooled and discharged into a 100 ml round bottom flask equipped with a distillation head, thermometer and mechanical stirrer containing 30% hydrogen peroxide (0.5 ml). The mixture was stirred for several hours at 30° C. and then neutralized with 1N hydrochloric acid followed by removal of tert-butanol by vacuum distillation giving 6.4 g of dodecyloxypropyl D-maltobionamide tetraoxyethylene ether.

Example 80 (11 Ether Heteroatoms)

Preparation of Dodecyloxypropyl D-Lactobionamide Octaoxyethylene Dipropylene ether A 100 g autoclave equipped with a pressure gauge, mechanical stirrer, rupture disk, gas inlet and gas outlet was charged with dodecyl oxypropyl D-lactobionamide (7.0 g, 1.16×10$^{-2}$ mole) dissolved in dimethylformamide (30 g) and potassium hydroxide (0.03 g, 5.82×10$^{-4}$ mole). The autoclave was flushed with a blanket of nitrogen and a mild vacuum pulled. Ethylene oxide (4.1 g, 9.28×10$^{-2}$ mole) was then added and the mixture heated to 70° C.–100° C. for six hours. Propylene oxide (1.3 g, 2.32×10$^{-2}$ mole) was then added and the mixture heated to 70° C.–100° C. for additional five hours. The mixture was then cooled and discharged into a 100 ml round bottom flask equipped with a distillation head, thermometer and mechanical stirrer containing sodium borohydride (0.1 g). The mixture was stirred for several hours at 30° C. and then neutralized with 0.1N hydrochloric acid followed by removal of dimethylformamide by vacuum distillation giving 12.5 g of dodecyl oxypropyl D-lactobionamide octaoxyethylenedipropylene ether.

Examples 81–84

Krafft Points and Foam Heights

Krafft Points

The temperature at and above which surfactants begin to form micelles instead of precipitates is referred to as the Krafft point ($T_k$) and at this temperature the solubility of a surfactant becomes equal to its CMC (numerical value at which micelles are formed).

The appearance and development of micelles are important since detergency (solubilization of soils) by dishwashing liquids, shampoos, detergents, etc., depend on the formation of these aggregates in solution.

The Krafft point was measured by preparing 650 ml of a 0.1% or 1.0% dispersion of aldonamide in water by weight. If the surfactant was soluble at room temperature, the solution was slowly cooled to 0° C. If the surfactant did not precipitate out of solution, its Krafft point was considered to be <0° C. (less than zero). If it precipitated out of solution, the temperature at which precipitation occurs was taken as the Krafft point.

If the surfactant was insoluble at room temperature, the dispersion was slowly heated until the solution became homogeneous. It was then slowly cooled until precipitation occurred. The temperature at which the surfactant precipitates out of solution upon cooling was taken as the Krafft point.

Foam Height

Foam is an important attribute in many consumer products. It is one of the dominant factors that determines the commercial value of products such as dishwashing liquids, shampoos and soaps. Also, acceptability of many consumer products is closely related to the quality and texture of the foam they produce (psychological aspect).

Since most of the foaming data on surfactants is typically obtained by the Ross-Miles Foam Height Assay (Ross, J. and Miles, G. D. Am Soc. for Testing Material Method D1173-63 Philadelphia, Pa. (1953); Oil & Soap (1958) 62:1260) the foaming ability of these surfactants were acquired using this method.

In the Ross-Miles method, 200 mL of a surfactant solution contained in a pipette of specified dimensions with a 2.9- mm-i.d. orifice is allowed to fall 90 cm onto 50 mL of the same solution contained in a cylindrical vessel maintained at a given temperature by means of a water jacket. The height of the foam produced in the cylindrical vessel is read immediately after all the solution has run out of the pipette and then again after a given amount of time.

Using this method, the foam production (initial foam height in mm) and foam stability (final foam height after 10 minutes in mm) were measured at 0.1% aldonamide concentration, 40° C. and 0 ppm (parts per million) hardness. Aldonamides that were not soluble at 40° C. were measured at about 5°–10° C. above their Krafft points.

In order to show the unexpected enhancement in solubility and foam, applicants compared a series of heteroatom containing alkyl aldonamide compound to a series of alkyl aldonamide compound having no heteroatom in the attached aliphatic group. The results are as follows:

Example 81

| | Monosaccharide Aldonamides Containing Four Hydroxyl Groups | | | | |
|---|---|---|---|---|---|
| Entry | Compound | Average # of Hydrocarbons | Foam Height Initial (mm) | Foam Height Final (mm) | Krafft Point (0.1%), °C. |
| A | $C_{12}$ Ribonamide (Comparative) | 12 | 184 | 103 | 54 |
| B | $C_8/C_{10}$ Oxypropyl D-Ribonamide | 11.6 | 217 | 200 | 10 |

Example 82

| | Monosaccharide Aldonamides Containing Five Hydroxyl Groups | | | | |
|---|---|---|---|---|---|
| Entry | Compound | Average # of Hydrocarbons | Foam Height Initial (mm) | Foam Height Final (mm) | Krafft Point (0.1%), °C. |
| C | $C_7$ D-Gluconamide (Comparative) | 7 | 0 | 0 | <0 |
| D | $C_8$ D-Gluconamide (Comparative) | 8 | 0 | 0 | 12 |
| E | $C_9$ D-Gluconamide (Comparative) | 9 | 0 | 0 | 53 |
| F | $C_{10}$ D-Gluconamide (Comparative) | 10 | 199 | 6 | 75 |
| G | $C_{11}$ D-Gluconamide (Comparative) | 11 | X | X | 87 |
| H | $C_{12}$ D-Gluconamide (Comparative) | 12 | X | X | 91 |
| I | $C_{12}$ L-Gluconamide (Comparative) | 12 | X | X | 91 |
| J | $C_{12}$ D-Galactonamide (Comparative) | 12 | - Insoluble - | | >100 |
| K | $C_{12}$ L-Galactonamide (Comparative) | 12 | - Insoluble - | | >100 |
| L | $C_{12}$ L-Mannonamide (Comparative) | 12 | - Insoluble - | | >100 |
| M | $C_{14}$ D-Gluconamide (Comparative) | 14 | - Insoluble - | | >100 |
| N | $C_{16}$ D-Gluconamide (Comparative) | 16 | - Insoluble - | | >100 |
| O | $C_{18}$ D-Gluconamide (Comparative) | 18 | -Insoluble - | | >100 |
| P | Ethylhexyloxypropyl D-Gluconamide | 11 | 0 | 0 | <0 |
| Q | $C_8/C_{10}$ Oxypropyl D-Gluconamide | 11.6 | 212 | 165 | 48 |
| R | Iso $C_{10}$ Oxypropyl D-Gluconamide | 13 | 213 | 206 | <0 |
| S | $C_{12}$ Oxypropyl D-Gluconamide | 15 | 200 | 110 | 61 |
| T | Iso $C_{13}$ Oxypropyl D-Gluconamide | 16 | 190 | 100 | <15 |
| U | $C_{12}$–$C_{15}$ Oxypropyl D-Gluconamide | 16.3 | 200 | 110 | 58 |
| V | $C_{14}$ Oxypropyl D-Gluconamide | 17 | 203 | 101 | 53 |
| W | N-D-Gluconyl $C_{12}$ Glycinate | 14 | 183 | 107 | 63 |
| X | N-D-Gluconyl $C_{12}$ | 14 | 185 | 111 | 63 |

-continued

Monosaccharide Aldonamides Containing Five Hydroxyl Groups

| Entry | Compound | Average # of Hydrocarbons | Foam Height Initial (mm) | Foam Height Final (mm) | Krafft Point (0.1%), °C. |
|---|---|---|---|---|---|
| Y | Ester of Ethanolamine N-D-Gluconyl $C_{12}$ DL-Alaninate | 15 | 197 | 112 | 53 |
| Z | N-D-Gluconyl $C_{12}$ Di(oxyethyl) Glycinate | 18 | 203 | 169 | <0 |
| AA | Cocoaminopropyl D-Gluconamide | 16 | 186 | 182 | 18 |
| BB | Soyaaminopropyl D-Gluconamide | 20.7 | 160 | 88 | <18 |
| CC | Oleylaminopropyl D-Gluconamide | 21 | 158 | 84 | <0 |
| DD | Iso $C_{13}$ Oxypropyl-aminopropyl D-Gluconamide | 19 | 180 | 178 | <0 |
| EE | $C_{12}$–$C_{15}$ Oxypropyl-aminopropyl D-Gluconamide | 19.3 | 180 | 176 | <0 |

X indicates low water solubility, foam height cannot be measured.

Example 83

Monosaccharide Aldonamides Containing Six to Seven Hydroxyl Groups

| Entry | Compound | Average # of Hydrocarbons | Foam Height Initial (mm) | Foam Height Final (mm) | Krafft Point (0.1%), °C. |
|---|---|---|---|---|---|
| FF | $C_{12}$ D-Glucooctonamide (Comparative) | 12 | X | X | 86 |
| GG | $C_{12}$ D-Glycero-L-Mannoheptonamide (Comparative) | 12 | - Insoluble - | | >100 |
| HH | $C_{12}$ D-Glucoheptonamide (Comparative) | 12 | X | X | 91 |
| II | $C_8/C_{10}$ Oxypropyl D-Glucoheptonamide | 11.7 | 221 | 90 | 60 |
| JJ | Iso $C_{10}$ Oxypropyl D-Glucoheptonamide | 13 | 215 | 204 | 18 |
| KK | $C_{12}$ Oxypropyl D-Glucoheptonamide | 15 | 245 | 80 | 73 |
| LL | $C_{12}$–$C_{15}$ Oxypropyl D-Glucoheptonamide | 16.3 | 239 | 97 | 68 |

X indicates low water solubility, foam height cannot be measured.

Example 84

Disaccharide Aldonamides Containing Eight Hydroxyl Groups

| Entry | Compound | Average # of Hydrocarbons | Foam Height Initial (mm) | Foam Height Final (mm) | Krafft Point (1.0%), °C. |
|---|---|---|---|---|---|
| MM | $C_9$ D-Lactobionamide (Comparative) | 9 | 0 | 0 | 42 |
| NN | $C_{11}$ D-Lactobionamide (Comparative) | 11 | 0 | 0 | 61 |
| OO | $C_{12}$ D-Lactobionamide (Comparative) | 12 | 153 | 20 | 38 |
| PP | $C_{13}$ D-Lactobionamide (Comparative) | 13 | 145 | 78 | 70 |
| QQ | $C_{14}$ D-Lactobionamide (Comparative) | 14 | 141 | 59 | 18 |
| RR | $C_{14}$ D-Maltobionamide (Comparative) | 14 | 145 | 140 | 46 |
| SS | $C_{15}$ D-Lactobionamide | 15 | X | X | 84 |

-continued

| | | | Foam | Foam | Krafft |
| | | Average # of | Height | Height | Point |
| Entry | Compound | Hydrocarbons | Initial (mm) | Final (mm) | (1.0%), °C. |
| --- | --- | --- | --- | --- | --- |
| | Disaccharide Aldonamides Containing Eight Hydroxyl Groups | | | | |
| | (Comparative) | | | | |
| TT | $C_{16}$ D-Lactobionamide | 16 | 95 | 95 | 64 |
| | (Comparative) | | | | |
| UU | $C_{18}$ D-Lactobionamide | 18 | X | X | 82 |
| | (Comparative) | | | | |
| VV | $C_8/C_{10}$ Oxypropyl D-Lactobionamide | 11.6 | 168 | 158 | <0 |
| WW | $C_{12}$ Oxypropyl D-Lactobionamide | 15 | 165 | 154 | <0 |
| XX | $C_{12}$ Oxypropyl D-Maltobionamide | 15 | 163 | 155 | <0 |
| YY | $C_{12}$–$C_{15}$ Oxypropyl D-Lactobionamide | 16.3 | 166 | 155 | <0 |
| ZZ | $C_{14}$ Oxypropyl D-Lactobionamide | 17 | 163 | 154 | <0 |
| AAA | D-Lactobionyl $C_{12}$ Glycinate | 14 | 161 | 153 | <0 |
| BBB | D-Lactobionyl $C_{12}$ β-Alaninate | 15 | 159 | 152 | <0 |
| CCC | Cocoaminopropyl D-Lactobionamide | 16 | 171 | 168 | <0 |
| DDD | Oleylaminopropyl D-Lactobionamide | 18 | 169 | 165 | <0 |
| EEE | $C_{12}$–$C_{15}$ Oxypropyl-aminopropyl D-lactobionamide | 19.3 | 173 | 169 | <0 |

X indicates low water solubility, foam height cannot be measured.

DETAILED DISCUSSION OF EXAMPLES 81–84

From the above Tables (81–83), it can be clearly seen that monosaccharide alkyl aldonamide compounds lacking a heteroatom in the hydrocarbon chain (A, C—O, FF—HH) provide little or no foam and have significantly higher Krafft points. While not wishing to be bound by theory, it is believed that these compounds pack closely in the solid state through strong amide/hydroxyl hydrogen bonding and strong hydrocarbon Van der Waal forces. The net result is an unfavorable heat of hydration, high Krafft point, low or no water solubility and a poor foaming profile. Changing the stereo chemistry (I—L) or increasing the hydrophilicity (FF—HH) of the sugar head group (by hydroxyl group addition) results in little or no improvement. However, monosaccharide alkyl aldonamide compounds that contain a heteroatom such as an oxygen (B, Q—V, II—LL), an ester (W—Y), an ester/oxygen combination (Z), a nitrogen (AA—CC) or a nitrogen/oxygen combination (DD, EE) in the hydrocarbon chain are believed to pack more loosely (favorably) in the solid state thereby resulting in a low Krafft point, increased water solubility and superior foaming profile. Also, closer comparison reveals that monosaccharide aldonamide compounds containing a heteroatom in the hydrocarbon chain unexpectedly allow the introduction of the same or greater alkyl chain length without sacrificing foaming and solubility characteristics. (Compare the average number of hydrocarbons of G—O to Q—EE and HH to II—LL).

Disaccharide alkyl aldobionamide compounds in Table 84 (MM—UU) tend to have reasonable Krafft points and foaming profiles. However, the addition of a heteroatom such as an oxygen (VV—ZZ), an ester (AAA, BBB), a nitrogen (CCC, DDD) or a nitrogen/oxygen combination in the hydrocarbon chain results in extremely low Krafft points (<0° C.), increased water solubility and enhanced foaming profile. Again, closer comparison reveals that disaccharide aldobionamide compounds containing a heteroatom in the hydrocarbon chain unexpectedly allow the introduction of the same or greater alkyl chain length without sacrificing foaming and solubility characteristics. (Compare the average number of hydrocarbons of OO—UU to VV—EE).

Thus, the ability of significantly improving the water solublity and foaming profile of an alkyl aldonamide or aldobionamide compound by heteroatom introduction is a significant achievement. These findings are quite unusual and unexpected, since monosaccharide alkyl aldonamide compounds are generally considered to be poor surfactants with poor emulsifing properties that are insoluble in water with little or no foaming capability.

Example 85

Foam Stability and Enhancement of Anionic Surfactants with Heteroatom Containing Alkyl Aldonamide Compounds In order to demonstrate the improved ability of heteroatom containing alkyl aldonamide compounds to stabilize and enhance foam, several surfactant compositions were prepared and the foam height measured under the following conditions:

| Foam Stability and Enhancement Conditions | |
| --- | --- |
| Temperature | 35° C. |
| pH | 10 |
| Sodium Triphosphate 6 $H_2O$ | $2.5 \times 10^{-3}$ M (1.2 g/L) |
| Sodium Carbonate | $3.9 \times 10^{-3}$ M (0.4 g/L) |
| Calcium Chloride (Hardness) | $2.0 \times 10^{-3}$ M (0.2 g/L) |
| Surfactant = $C_8/C_{10}$ OPG : $C_{12}$ LAS | 10:90 mole % |
| Surfactant = $C_{12}$ Amide DEA : $C_{12}$ LAS | 10:90 mole % |
| Surfactant = $C_{12}$ Amide MEA : $C_{12}$ LAS | 10:90 mole % |
| Surfactant = Cocopolyglucoside : $C_{12}$ LAS | 10:90 mole % |

-continued

| Foam Stability and Enhancement Conditions | |
|---|---|
| Surfactant = $C_{12}$ Gluconamide : $C_{12}$ LAS | 10:90 mole % |
| Total Surfactant Concentration | $5.0 \times 10^{-3}$ M |
| Triolein/Calcium Stearate (90/10 by wt.) | 1 g/L |

The triolein/calcium stearate mixture was dispersed to the above solutions using a high speed shear mixer at 60° C. and then cooled to 35° C. The triolein/calcium stearate mixture represents an extreme type of antifoam behavior found in sebum soil.

The foaming behavior of the above surfactants was determined by the Ross-Miles Foam Height Assay (Ross, J. and Miles, G. D. Am Soc. for Testing Material Method D1173-63 Philadelphia, Pa. (1953); Oil & Soap (1958) 62:1260) and the cylinder shaking method.

In the Ross-Miles method, 200 mL of a surfactant solution contained in a pipette of specified dimensions with a 2.9-mm-i.d. orifice is allowed to fall 90 cm onto 50 mL of the same solution contained in a cylindrical vessel maintained at a given temperature by means of a water jacket. The height of the foam produced in the cylindrical vessel is read after 30 minutes has elapsed.

In the cylinder shaking method, 25 ml of a surfactant solution is placed in a 250 ml graduated cylinder and shook for 10 seconds. The height of the foam produced in the cylinder is read after 30 minutes has elapsed.

The foam stability and enhancement of the heteroatom containing alkyl aldonamides was determined using a 0:100 and 10:90 mole percent of a solution of $C_8/C_{10}$ oxypropyl D-gluconamide ($C_8/C_{10}$ OPG): sodium dodecyl benzene sulfonate ($C_{12}$ LAS) and compared to identical solutions of lauramide diethanolamine ($C_{12}$ amide DEA): sodium dodecyl benzene sulfonate, coconut polyglucoside: sodium dodecyl benzene sulfonate, lauramide monoethanolamine ($C_{12}$ amide MEA): sodium dodecyl benzene sulfonate and dodecyl D-gluconamide ($C_{12}$ Gluc): sodium dodecyl benzene sulfonate in the presence and absence of the triolein/calcium stearate antifoam. The results were determined by cylinder shaking and are as follows:

| Foam Stability and Enhancement of Sodium Dodecyl Benzene Sulfonate with Various Foam Stabilizers/Enhancers | | |
|---|---|---|
| | Foam Height (mm) | |
| Mole % | No Antifoam | With Antifoam |
| $C_8/C_{10}$ OPG:$C_{12}$ LAS | 195 | 85 |
| $C_{12}$ amide DEA:$C_{12}$ LAS | 190 | 30 |
| Coconut polyglucoside:$C_{12}$ LAS | 160 | 28 |
| $C_{12}$ amide MEA:$C_{12}$ LAS | 150 | 30 |
| $C_{12}$ LAS (Control) | 160 | 20 |
| $C_{12}$ Gluc:$C_{12}$ LAS (Comparative) | Insoluble | Insoluble |

From the above table it can be seen that $C_8/C_{10}$ oxypropyl D-gluconamide was found to enhance as well as stabilize the foam of a typical anionic surfactant. This enhancement was better than lauramide diethanolamine, coconut polyglucoside, lauramide monoethanolamine, dodecyl D-gluconamide and sodium dodecyl benzene sulfonate (alone) especially in the presence of triolein/calcium stearate antifoam. This finding suggests that the heteroatom containing alkyl aldonamide compounds of the present invention are useful as effective foam stabilizers and foam enhancers.

The foam stability and enhancement of the heteroatom containing alkyl aldonamides was further determined using a 10:90 mole percent solution of $C_8/C_{10}$ oxypropyl D-gluconamide ($C_8/C_{10}$ OPG): sodium dodecyl benzene sulfonate ($C_{12}$ LAS) and compared to identical solutions of dodecyl D-gluconamide ($C_{12}$ Gluc): sodium dodecyl benzene sulfonate in the presence and absence of the triolein/calcium stearate antifoam. The results were determined by the Ross-Miles method and are as follows:

| Foam Stability and Enhancement of Sodium Dodecyl Benzene Sulfonate with Heteroatom Containing Alkyl Aldonamide Compounds | | |
|---|---|---|
| | Foam Height (mm) | |
| Mole % | No Antifoam | With Antifoam |
| $C_8/C_{10}$ OPG:$C_{12}$ LAS | 147 | 98 |
| $C_{12}$ LAS (Control) | 131 | 61 |
| $C_{12}$ Gluc:$C_{12}$ LAS (Comparative) | Insoluble | Insoluble |

From the above table it can be seen that $C_8/C_{10}$ oxypropyl D-gluconamide was found to enhance as well as stabilize the foam of a typical anionic surfactant. This enhancement was better than dodecyl D-gluconamide and sodium dodecyl benzene sulfonate alone especially in the presence of triolein/calcium stearate antifoam. This finding suggests that the heteroatom containing alkyl aldonamide compounds of the present invention are useful as effective foam stabilizers and foam enhancers.

Example 86

Foam Stability and Enhancement of Anionic Surfactants with Heteroatom Containing Alkyl Aldonamide Compounds In order to further demonstrate the improved ability of heteroatom containing alkyl aldonamide compounds to stabilize and enhance foam, several prototype personal product compositions were prepared and thier foam stability and enhancement measured at 45° C. by the Ross-Miles Foam Height assay. The results were compared to identical compositions comprising petrochemically derived foam stabilizing agents, in particular, alkanolamides and alcohol ethoxylates. The prototype personal product composition is as follows:

| Prototype Personal Product Compositions Comprising Sodium/Ammonium Lauryl Sulfate and Heteroatom Containing Alkyl Aldonamide Compounds | | |
|---|---|---|
| Ingredients | Wt | Function |
| Sodium Lauryl Sulfate | 9.0% | Cleansing Agent |
| Ammonium Lauryl Sulfate (30% Active) | 15.0% | Cleansing Agent |
| Heteroatom Containing Alkyl Aldonamide, Alkanolamide or Alcohol Ethoxylate | 4.0% | Foam Stabilizer/ Thickener |
| Glycerine | 3.0% | Solubilizer |
| Sodium Chloride | 0.9% | Viscosity Cobuilder |
| Methyl Cellulose (25 cp at 2%) | 0.4% | Viscosity Cobuilder |
| Disodium EDTA | 0.1% | Sequestering Agent |
| Methyl Paraben | 0.1% | Preservative |
| Propyl Paraben | 0.01% | Preservative |
| Distilled Water | 67.49% | |
| Total | 100.0% | |

The compositions were prepared by admixing the ingredients in listed order with rapid stirring at 45°–50° C. Foam stability and enhancement were measured at 0.1% based on sodium and ammonium lauryl sulfate (0.16% total solids) at 45° C. and 0 or 120 parts per million (ppm) hardness calcium:magnesium ion 2:1. The results are set forth below:

Foam Stability and Enhancement of Sodium/Ammonium Lauryl Sulfate with Heteroatom Containing Alkyl Aldonamide Compounds at 0 ppm Hardness

| Formulation (Example 86) | Initial FH (mm) | Final FH after 60 Min. (mm) |
|---|---|---|
| $C_8/C_{10}$ Oxypropyl D-Gluconamide | 187 | 150 |
| Lauramide DEA | 190 | 151 |
| Cocoamide MEA | 178 | 70 |
| Neodol 91-6 | 174 | 6 |
| No Foam Stabilizer (Control) | 149 | 5 |

Foam Stability and Enhancement of Sodium/Ammonium Lauryl Sulfate with Heteroatom Containing Alkyl Aldonamide Compounds at 120 ppm Hardness

| Formulation (Example 86) | Initial FH (mm) | Final FH after 60 Min. (mm) |
|---|---|---|
| $C_8/C_{10}$ Oxypropyl D-Gluconamide | 161 | 128 |
| Lauramide DEA | 159 | 126 |
| Cocoamide MEA | 148 | 53 |
| Neodol 91-6 | 145 | 5 |
| No Foam Stabilizer (Control) | 127 | 5 |

From the above table it can be seen that $C_8/C_{10}$ oxypropyl D-gluconamide was found to enhance as well as stabilize the foam of a typical personal product formulation. This enhancement was comparable to lauramide diethanolamine and better than cocoaide monoethanolamine or Neodol 91-6 ($C_9$–$C_{11}$ alcohol ethoxylate with 6 moles of ethylene oxide) especially in the presence of hardness. This finding suggests that the heteroatom containing alkyl aldonamide compounds of the present invention are useful as effective foam stabilizers and foam enhancers.

Example 87

Clarity Enhancement of Heteroatom Containing Alkyl Aldonamide Compounds

In order to demonstrate the improved ability of heteroatom containing alkyl aldonamide compounds to enhance clarity, several prototype personal product compositions were prepared and thier clarity measured at room temperature (~21° C.). The prototype personal product composition is as follows:

Prototype Personal Product Compositions Comprising Sodium Lauryl Sulfate and Alkyl Aldonamide Compounds (Comparative)

| Ingredients | Wt | Function |
|---|---|---|
| Sodium Lauryl Sulfate | 15.0% | Cleansing Agent |
| Alkyl Aldonamide | 3.0–5.0% | Comparative |
| Sodium Chloride | 2.0% | Viscosity Cobuilder |
| Distilled Water | 78.0–80.0% | |
| Total | 100.0% | |

Prototype Personal Product Compositions Comprising Sodium Lauryl Sulfate and Heteroatom Containing Alkyl Aldonamide Compounds

| Ingredients | Wt | Function |
|---|---|---|
| Sodium Lauryl Sulfate | 15.0% | Cleansing Agent |
| Heteroatom Containing Alkyl Aldonamide | 3.0–5.0% | Foam Stabilizer/Thickener |
| Sodium Chloride | 2.0% | Viscosity Cobuilder |
| Distilled Water | 78.0–80.0% | |
| Total | 100.0% | |

The above formulations were prepared by admixing the above ingredients in listed order and heating the mixture to about 80° C. with rapid stirring. The mixture was then cooled to about 40° C., placed in a clear jar and stored at room temperature for 6 months. The results are as follows:

The Clarity Enhancement of Prototype Personal Product Compositions Comprising Heteroatom Containing Alkyl Aldonamide Compounds and Sodium Lauryl Sulfate

| Wt | Thickener (Example 87) | Appearance (Time) |
|---|---|---|
| 0.0% | No Thickener (Control) | Precipitate (2 weeks) |
| 4.0% | $C_9$ D-Gluconamide (Comparative) | Precipitate (2 weeks) |
| 5.0% | $C_9$ D-Gluconamide (Comparative) | Precipitate (2 weeks) |
| 3.0% | $C_{10}$ D-Gluconamide (Comparative) | Precipitate (1 week) |
| 5.0% | $C_{10}$ D-Gluconamide (Comparative) | Precipitate (5 days) |
| 3.0% | $C_{12}$ D-Gluconamide (Comparative) | Precipitate (2 days) |
| 5.0% | $C_{12}$ D-Gluconamide (Comparative) | Precipitate (1 hour) |
| 3.0% | Coco D-Gluconamide (Comparative) | Precipitate (1 day) |
| 5.0% | Coco D-Gluconamide (Comparative) | Precipitate (2 hours) |
| 3.0% | $C_8/C_{10}$ Oxypropyl D-Gluconamide | Clear |
| 4.0% | $C_8/C_{10}$ Oxypropyl D-Gluconamide | Clear |
| 5.0% | $C_8/C_{10}$ Oxypropyl D-Gluconamide | Clear |
| 3.0% | $C_{12}$ Oxypropyl D-Gluconamide | Clear |
| 5.0% | $C_{12}$ Oxypropyl D-Gluconamide | Precipitate (5 months) |
| 3.0% | Cocoaminopropyl D-Gluconamide | Clear |
| 5.0% | Cocoaminopropyl D-Gluconamide | Clear |
| 3.0% | $C_8/C_{10}$ Oxypropyl D-Lactobionamide | Clear |
| 5.0% | $C_8/C_{10}$ Oxypropyl D-Lactobionamide | Clear |

For a clear personal product formulation to be successful it must have good shelf life and should not become turbid or produce sedimentation upon standing. From the above table it can be seen that the personal product compositions comprising alkyl aldonamides that lack heteroatoms do not stay in solution and precipitate out within an hour to about 2 weeks whereas those that contain heteroatoms stay in solution for 5 months or greater and provide clear personal product formulations. This finding also suggests that the non-heteroatom containing alkyl aldonamide compounds of the invention are useful as pearlescent agents (opacifiers) which provide a soft, silvery and pearly luster to personal product compositions, and as suspending agents which provide a means of suspending certain ingredients effectively, thereby assisting in the delivery of the desirable performance attributes associated with these ingredients.

Example 88

Viscosity Modification of Sodium Lauryl Sulfate with Heteroatom Containing Alkyl Aldonamide Compounds In order to demonstrate the improved ability of heteroatom containing alkyl aldonamide compounds to enhance viscosity, several prototype personal product compositions were prepared and thier viscosity measured using a Brookfield Digital Viscometer at 220° C. The prototype personal product composition is as follows:

Prototype Personal Product Compositions Comprising Sodium Lauryl Sulfate and Heteroatom Containing Alkyl Aldonamide Compounds

| Ingredients | Wt | Function |
| --- | --- | --- |
| Sodium Lauryl Sulfate | 15.0% | Cleansing Agent |
| Heteroatom Containing Alkyl Aldonamide | 1.0–5.0% | Foam Stabilizer/ Thickener |
| Sodium Chloride | 2.0% | Viscosity Cobuilder |
| Distilled Water | 78.0–82.0% | |
| Total | 100.0% | |

The above formulations were prepared by admixing the above ingredients in listed order and heating the mixture to about 80° C. with rapid stirring. The mixture was then cooled to about 40° C., placed in a clear jar and stored at room temperature for 6 months.

It is well known that the viscosity of a liquid composition comprising of anionic surfactant can be modified by the addition of inorganic salts, such as sodium chloride. However, in the absence of an organic modifier, high levels of salt may be necessary to achieve the required viscosity which may lead to problems of storage at cold temperature or even salting out certain ingredients. In practice, however, the viscosity of a liquid composition is modified by the simultaneous addition of thickener and small amounts of inorganic salt (viscosity cobuilder). The combined effect is greater than either one alone. The viscosity of the above prototype personal product compostion comprising various amounts of heteroatom containing alkyl aldonamide compound is as follows:

The Viscosity of Prototype Personal Product Compositions Comprising Sodium Lauryl Sulfate and Heteroatom Containing Alkyl Aldonamide Compounds

| Wt | Thickener (Example 88) | Viscosity (Centipoise) | Increase |
| --- | --- | --- | --- |
| 1.0% | $C_8/C_{10}$ Oxypropyl D-Gluconamide | 200 | 13x |
| 2.0% | $C_8/C_{10}$ Oxypropyl D-Gluconamide | 400 | 27x |
| 3.0% | $C_8/C_{10}$ Oxypropyl D-Gluconamide | 1200 | 80x |
| 4.0% | $C_8/C_{10}$ Oxypropyl D-Gluconamide | 2220 | 148x |
| 5.0% | $C_8/C_{10}$ Oxypropyl D-Gluconamide | 12900 | 860x |
| 3.0% | $C_{12}$ Oxypropyl D-Gluconamide | 1800 | 120x |
| 5.0% | $C_{12}$ Oxypropyl D-Gluconamide | 20600 | 1373x |
| 3.0% | $C_{12}$ Oxypropyl D-Lactobionamide | 340 | 23x |
| 5.0% | $C_{12}$ Oxypropyl D-Lactobionamide | 1455 | 97x |
| 0.0% | No Thickener (Control) | 15 | 0x |

From the above table it can be seen that the addition of a heteroatom containing alkyl aldonamide compound to a personal product formulation increased the viscosity of that composition from about 13 to about 1373 times from its normal viscosity. This finding suggests that heteroatom containing alkyl aldonamide compounds of the invention are useful as effective viscosity modifiers or thickeners.

In order to further demonstrate the improved ability of heteroatom containing alkyl aldonamide compounds to enhance viscosity, the viscosity of several prototype personal product compositions in Example 86 were measured using a Brookfield Digital Viscometer at 22° C. The results are as follows:

Viscosity Enhancement of Sodium/Ammonium Lauryl Sulfate with Heteroatom Containing Alkyl Aldonamide Compounds Formulation (Example 86)

| 4.0% Thickener | Viscosity (Centipoise) |
| --- | --- |
| $C_8/C_{10}$ Oxypropyl D-Gluconamide | 2395 |
| Lauramide DEA | 2376 |
| Cocoamide MEA | 1720 |
| Neodol 91-6 | 212 |
| No Thickener (Control) | 22 |

From the above table it can be seen that the addition of $C_8/C_{10}$ oxypropyl D-gluconamide to a personal product formulation increased the viscosity of that composition 109 times (2395/22=109x) from its normal viscosity. Also closer comparision reveals that $C_8/C_{10}$ oxypropyl D-gluconamide enhances the viscosity of a personal product composition more effectively than lauramide diethanolamine (DEA), cocoamide monoethanolamine (MEA) or Neodol 91-6 ($C_9$–$C_{11}$ alcohol ethoxylate with 6 moles of ethylene oxide). This finding suggests that heteroatom containing alkyl aldonamide compounds of the invention are useful as effective viscosity modifiers or thickeners.

While not wishing to be bound to theory, it is believed that common thickeners and foam stabilizers such as lauramide DEA and cocoamide MEA operate by being solubilized in the palisade layer of the ionic micelle. Here they act as "buffers" between repelling ionic head groups producing a closer-packed coherent surface film of foam that is more resilient and slow draining. The efficiency of an additive to stabilize foam and enhance viscosity increases with the number of hydrogen bonding groups per molecule as well as the number of carbons in the alkyl chain. Additive hydrogen bonding groups are attacted to the ionic head groups of the surfactant by ion-dipole interactions whereas the hydrocarbon portions are attracted by Van der Waals forces. Therefore, the greater the intermolecular cohesive forces, the more effectively the additive is held in the palisade layer. Since long chained heteroatom containing alkyl aldonamide compounds contain multiple hydrogen bonding groups, they should be held tightly in the palisade layer and should not be squeezed out or forced into the interior of the micelle. If the hetroatom containing alkyl aldonamide compound is of proper size, as those described in this disclosure, a composition will exhibit enhanced stable foam and increased viscosity as shown in Examples 85–88.

Example 89

Mildness Potential of Heteroatom Containing Alkyl Aldonamide Compounds (Zein Solublization Assay)

The zein solubilization assay was developed to determine the biological effects of surfactants on the skin. The protein is normally in soluble in water, but can be brought into solution by interaction with surfactants. The extent of zein dissolved is related to the irritation potential (M. J. Schwinger, Kolloid-Z. Z. Poly., 233, 848, 1969). The greater the zein solubilization, the greater the irritation potential of that surfactant on the skin.

In order to demonstrate the improved ability of heteroatom containing alkyl aldonamide to provide mildness benefits to the skin, mixtures of $C_8/C_{10}$ oxypropyl D-gluconamide ($C_8/C_{10}$ OPG) and sodium lauryl sulfate (SLS) by weight were tested and compared to pure sodium lauryl sulfate. Thus, a 1% solution of surfactant (30 mls) was added to 1.5 g of zein and stirred at room temperature for 1 hour. Residual zein was collected and dried to constant weight. Differences between starting and residual weights were used to calculate % zein solubilized. The results are as follows:

| Mildness Potential of Heteroatom Containing Alkyl aldonamide Compounds (Zein Solublization Assay) | |
| --- | --- |
| Active Ratio ($C_8/C_{10}$ OPG:SLS) | % Zein Solubilized |
| 0:100 | 86 |
| 25:75 | 58 |
| 50:50 | 43 |
| 75:25 | 22 |
| 100:0 | 6 |
| No Surfactant (Control) | 5 |

As indicated by the adove table, the addition of $C_8/C_{10}$ oxypropyl D-gluconamide to sodium lauryl sulfate results in less zein solubilization. This result suggests that these formulations (25:75 to 100:0) are more mild than sodium lauryl sulfate alone, and so the heteratom containing alkyl aldonamide compounds not anly enhance viscosity and stabilize foam, but are also mild to the skin.

Examples 90–96

Physical Chemistry of Heteroatom Containing Alkyl Aldonamide Compounds

There are several unique characteristic properties that distinguish surface-active materials (surfactants) from other non-surface active materials. These include critical micelle concentration, surface tension reduction, efficiency in surface tension reduction, effectiveness in surface tension reduction, effectiveness of adsorption, area per molecule and micellar shape or structure. The following examples will show that the heteroatom containing alkyl aldonamide compounds of the invention are surface-active and are therefore considered to be a new class of sugar based surfactant.

Example 90

Critical Micelle Concentration

The critical micelle concentration (CMC) is defined as the concentration at which a surfactant forms micelles in aqueous solution. Micellization is the preferred interfacial phenomena, since certain surfactant benefits such as detergency (the solubilization of soils), foaming, wetting or emulsification depend on the formation of these aggregates in solution. Materials that do not form micelles do not provide any detergency, foaming, wetting or emulsification.

The CMC value of $C_8/C_{10}$ oxypropyl D-gluconamide was determined by plotting surface tension as a function of log[concentration] and extrapolating linear points to obtain an intersection point. The concentration at this point was taken as the CMC. The technique used was the Wilhelmy plate method and the instrument used was a Lauda Auto-Tensiometer. While wishing not to be bound to theory, it is believed that surfactants with low CMC values form micelles more readily at lower concentrations than those with high CMC values.

The critical micelle concentration (CMC) value of $C_8/C_{10}$ oxypropyl D-gluconamide (molecular weight=375.02 g/mole, 65.9% $C_8$, 34.1% $C_{10}$) was determined and is set forth below:

| The Critical Micelle Concentration of $C_8/C_{10}$ Oxypropyl D-Gluconamide | | | |
| --- | --- | --- | --- |
| Entry | Surfactant | ANC* | CMC | Temperature (°C.) |
| 1 | $C_8/C_{10}$ Oxypropyl D-Gluconamide | 11.7 | 0.095 mM (0.0356%) | 60 |
| 2 | Dodecyl D-Gluconamide (Comparative) | 12.0 | None (Insoluble) | 60 |

(*)ANC = Average Number of Carbon Atoms in the Alkyl Chain

A necessary and sufficient condition for CMC formation and surface tension reduction is the presence of both hydrophilic and hydrophobic functional groups. The hydrophilic portion provides strong interaction between the surfactant at the interface and with the surrounding water phase. The hydrophobic portion provides spontaneous adsorption of the surfactant at the interface and strong interaction with the adjacent air phase. If any of these functions are not performed, then CMC formation and surface tension reduction will not occur. For significant surface activity, a properly balanced hydrophilic and hydrophobic character is essential. From the above table it can be seen that $C_8/C_{10}$ oxypropyl D-gluconamide is properly balanced and forms micelles at a surprising low critical micelle concentration whereas dodecyl D-gluconamide is insoluble in water and can not form micelles. This finding suggests that the heteroatom containing alkyl aldonamides of the invention to be surface-active and so these compounds are expected to deliver favorable surfactant benefits. Also, since dodecyl D-gluconamide is insoluble in water, the additional physical properties in Examples 91–96 of this compound can not be determined.

Example 91

Surface Tension Reduction

An important characteristic feature that surfactants have is the tendency for them to absorb at the water/air interface in an oriented manner, thereby altering the interfacial free energy of that surface. The surface free energy per unit area or surface tension ($\gamma$), is a measure of this work and may be considered as the minimum amount of work required to bring sufficient surfactant molecules to the surface.

The surface tension ($\gamma$) value of $C_8/C_{10}$ oxypropyl D-gluconamide was determined and is set forth below:

| Surface Tension of $C_8/C_{10}$ Oxypropyl D-Gluconamide at the Water/Air Interface | | | |
| --- | --- | --- | --- |
| Entry | Surfactant | $\gamma$ | Temperature (°C.) |
| 1 | $C_8/C_{10}$ Oxypropyl D-Gluconamide | 29.2 dyn/cm | 60 |
| 2 | Water | 60.2 dyn/cm | 60 |

From the above table it can be seen that $C_8/C_{10}$ oxypropyl D-gluconamide absorbs strongly at the water/air interface resulting in a significant reduction in water surface tension. This finding suggests that the heteroatom containing alkyl aldonamides of the invention to be surface-active and so these compounds are expected to deliver favorable surfactant benefits.

Examples 92–93

Performance of Heteroatom Containing Alkyl Aldonamide Compounds in Reducing Surface Tension For the purpose of comparing the performance of heteroatom containing alkyl aldonamide compounds in reducing surface tension to other surfactants, it is necessary to distinguish between the efficiency and effectiveness.

Efficiency of a surfactant in reducing surface tension is defined as the bulk phase surfactant concentration required to reduce the surface tension of water by some given mount.

Effectiveness of a surfactant in reducing surface tension is defined as the maximum reduction in surface tension that can be obtained regardless of the bulk phase surfactant concentration.

Example 92

Efficiency in Surface Tension Reduction

Since surface tension reduction depends on the replacement of water molecules at the interface by surfactant molecules, the efficiency of a surfactant in reducing interfacial tension should reflect the concentration of surfactant at the interface relative to that in bulk liquid phase. A suitable measure of efficiency with which a surfactant performs this function can be described as $pC_{20}$. This is defined as the negative logarithm of the bulk phase surfactant concentration necessary to reduce the surface tension of water by 20 dyn/cm and is given as:

$$pC_{20} = -\log[C_{(-\Delta\gamma=20)}] = -\log[C_{20}]$$

wherein:

$C_{(-\Delta\gamma=20)} = C_{20}$ is the bulk phase surfactant concentration necessary to reduce the surface tension of water by 20 dyn/cm.

In general, $pC_{20}$ values are usually close to the minimum concentration needed to saturate the interface with surfactant molecules. While not wishing to be bound by theory, it is believed that surfactants that have high $pC_{20}$ values tend to absorb more efficiently at the interface thereby reducing the surface tension more efficiently than those that have low $pC_{20}$ values.

The efficiency of various surfactants in reducing surface tension ($pC_{20}$) were determined and are set forth below:

The Efficiency of Various Nonionic Surfactants in Reducing the Surface Tension of Water

| Entry | Surfactant | ANC* | $pC_{20}$ | Temperature (°C.) |
|---|---|---|---|---|
| 1 | $C_8/C_{10}$ Oxypropyl D-Gluconamide | 11.7 | 4.78 | 60 |
| 2 | Dodecytri(oxyethylene) Ether[1] $C_{12}H_{25}O(CH_2CH_2O)_3H$ (Comparative) | 12 | 5.34 | 25 |
| 3 | Dodecyltetra(oxyethylene) Ether[1] $C_{12}H_{25}O(CH_2CH_2O)_4H$ (Comparative) | 12 | 5.34 | 25 |
| 4 | Dodecylpenta(oxyethylene) Ether[1] $C_{12}H_{25}O(CH_2CH_2O)_5H$ (Comparative) | 12 | 5.37 | 25 |
| 5 | Dodecylhepta(oxyethylene) Ether[1] $C_{12}H_{25}O(CH_2CH_2O)_7H$ (Comparative) | 12 | 5.26 5.28 5.41 | 25 40 60[2] |
| 6 | Dodecylocta(oxyethylene) Ether[1] $C_{12}H_{25}O(CH_2CH_2O)_8H$ (Comparative) | 12 | 5.20 5.22 5.39 | 25 40 60[2] |

[1]Rosen, M. J., in Surfactants and Interfacial Phenomena 2 ed., Wiley-Interscience Publication, 1989, pg 78; and Rosen, M. J., Cohen A. W., Dahanayake M. and Hua X. Y., J. Phys. Chem. 86, 541, 1981.
[2]This value was estimated by plotting temperature as function of $pC_{20}$ and extrapolating a linear line at 60° C.
(*)ANC = Average Number of Carbon Atoms in the Alkyl Chain From the above table it can be seen that $C_8/C_{10}$ oxypropyl D-gluconamide has a high $pC_{20}$ value and is expected to efficiently reduce the surface tension of water. This finding suggests that the heteroatom containing alkyl aldonamides of the invention to be surface-active and so these compounds are expected to deliver favorable surfactant benefits.

Example 93

Effectiveness in Reducing Surface Tension

As mentioned before, surface tension reduction depends on the replacement of water molecules at the interface by surfactant molecules, therefore the effectiveness of a surfactant in reducing interfacial surface tension should reflect the saturated concentration of surfactant at the interface relative to that in bulk liquid phase. During this process the surface tension of water steadily decreases as bulk phase surfactant concentration increases. This will continue until the concentration reaches the critical micelle concentration (CMC), above which the surface tension remains nearly unchanged and the interface is saturated with surfactant. The surface tension at the CMC is therefore very close to the minimum interfacial tension or maximum surface pressure that the system can achieve. The surface pressure at this point, $\Pi_{cmc}$, is a suitable measure of the effectiveness of a surfactant in reducing surface tension and is given as:

$$\Pi_{cmc} = 20 + 2.3nRT(\Gamma_{max})\log[CMC/C_{20}]$$

wherein:

n=1 which represents the number of ions whose surface concentration changes with the change in liquid phase surfactant concentration.
R=8.314×10$^7$ ergs/mol K (Gas Constant)
T=333.15 K
$\Gamma_{max} = -1/2.303 \ RT(\partial\gamma/\partial\log[Conc])_T = 3.85 \times 10^{-10}$ mole/cm$^2$ $CMC/C_{20}$=is the ratio of the critical micelle concentration to the bulk phase surfactant concentration necessary to reduce the surface tension of water by 20 dyn/cm.

While not wishing to be bound by theory, it is believed that surfactants that have higher $\Pi_{cmc}$ values tend to absorb effectively at the interface thereby reducing the surface tension of water more effectively than those with lower $\Pi_{cmc}$ values.

The effectiveness of various surfactants in reducing surface tension ($\Pi_{cmc}$) were determined and are set forth below:

Effectiveness of Various Nonionic Surfactants in Reducing the Surface Tension of Water

| Entry | Surfactant | CMC/$C_{20}$ | $\Pi_{cmc}$ | Temperature (°C.) |
|---|---|---|---|---|
| 1 | $C_8/C_{10}$ Oxypropyl D-Gluconamide | 5.7 | 38.5 dyn/cm | 60 |
| 2 | Dodecyltri(oxyethylene) Ether[1] $C_{12}H_{25}O(CH_2CH_2O)_3H$ (Comparative) | 11.4 | 44.1 dyn/cm 43.1 dyn/cm 41.4 dyn/cm | 25 40 60[2] |
| 3 | Dodecyltetra(oxyethylene) Ether[1] $C_{12}H_{25}O(CH_2CH_2O)_4H$ (Comparative) | 13.7 11.8 | 43.4 dyn/cm 42.0 dyn/cm 40.7 dyn/cm | 25 40 60[2] |
| 4 | Dodecylpenta(oxyethylene) Ether[1] $C_{12}H_{25}O(CH_2CH_2O)_5H$ (Comparative) | 15.0 | 41.5 dyn/cm 41.2 dyn/cm 40.7 dyn/cm | 25 40 60[2] |
| 5 | Dodecylhepta(oxyethylene) | 14.9 | 38.3 dyn/cm | 25 |

-continued

Effectiveness of Various Nonionic Surfactants in Reducing the Surface Tension of Water

| Entry | Surfactant | CMC/$C_{20}$ | $\Pi_{cmc}$ | Temperature (°C.) |
|---|---|---|---|---|
| | Ether[1] | | | |
| | $C_{12}H_{25}O(CH_2CH_2O)_7H$ | 13.9 | 38.5 dyn/cm | 40 |
| | (Comparative) | | 36.8 dyn/cm | 60[2] |
| 6 | Dodecylocta(oxyethylene) Ether[1] | 17.3 | 37.2 dyn/cm | 25 |
| | $C_{12}H_{25}O(CH_2CH_2O)_8H$ | 15.4 | 37.3 dyn/cm | 40 |
| | (Comparative) | | 36.3 dyn/cm | 60[2] |

[1]Rosen, M. J., in Surfactants and Interfacial Phenomena 2 ed., Wiley-Interscience Publication, 1989, pgs 146 and 224; and Rosen, M. J., Cohen A. W., Dahanayake M. and Hua X Y., J. Phys. Chem. 86, 541, 1981.
[2]This value was estimated by plotting temperature as function of surface pressure ($\Pi_{cmc}$) and extrapolating a linear line at 60° C.

From the above table it can be seen that $C_8/C_{10}$ oxypropyl D-gluconamide has a high $\Pi_{cmc}$ value and is expected to effectively reduce the surface tension of water. For $C_8/C_{10}$ oxypropyl D-gluconamide, the surface pressure ($\Pi_{cmc}$) was found to be similar to dodecytetra(oxyethylene) ether and dodecylpenta(oxyethylene) ether. This finding suggests that the heteroatom containing alkyl aldonamide compounds of the invention to be surface-active and so these compounds are expected to deliver favorable surfactant benefits.

Example 94

Effectiveness of Adsorption at the Interface

The surface excess concentration at surface saturation ($\Gamma_{max}$) is defined as a measure of the effectiveness of surfactant adsorption at the water/air interface and represents the maximum value to which adsorption can be obtained. Effectiveness of adsorption is related to the interfacial area occupied by the surfactant molecule. The smaller the effective cross-sectional area of a surfactant at the interface, the greater its effectiveness of adsorption. The effectiveness of adsorption is an important factor in determining surfactant properties such as detergency, foaming, wetting or emulsification. While not wishing to be bound by theory, it is believed that surfactants that absorb effectively at the interface tend have tightly packed coherent interfacial films and often provide better surfactant benefits than those with loosely packed noncoherent films. The effectiveness of adsorption of $C_8/C_{10}$ oxypropyl D-gluconamide was determined using the Gibbs equation given as:

$$\Gamma_{max} = -1/2.303\ RT(\partial\gamma/\partial\log[Conc])_T$$

wherein: $(\partial\gamma/\partial\log[Conc])_T = -24.574971$ ergs/cm² (which is equivalent to the slope of a plot of $\gamma$ versus log[Conc])
$R = 8.314 \times 10^7$ ergs/mol K. (Gas Constant)
$T = 333.15$ K.

The surface excess concentration at surface saturation ($\Gamma_{max}$) of various surfactants were determined and are set forth below:

Effectiveness of Adsorption of Various Nonionic Surfactants at the Water/Air Interface

| Entry | Surfactant | $\Gamma_{max}$ | Temperature (°C.) |
|---|---|---|---|
| 1 | $C_8/C_{10}$ Oxypropyl D-Gluconamide | $3.85 \times 10^{-10}$ mole/cm² | 60 |
| 2 | Dodecyltri(oxyethylene) Ether[1] | $3.98 \times 10^{-10}$ mole/cm² | 25 |
| | $C_{12}H_{25}O(CH_2CH_2O)_3H$ | $3.90 \times 10^{-10}$ mole/cm² | 40 |
| | (Comparative) | $3.83 \times 10^{-10}$ mole/cm² | 60[2] |
| 3 | Dodecyltetra(oxyethylene) Ether[1] | $3.63 \times 10^{-10}$ mole/cm² | 25 |
| | $C_{12}H_{25}O(CH_2CH_2O)_4H$ | $3.41 \times 10^{-10}$ mole/cm² | 40 |
| | (Comparative) | $3.01 \times 10^{-10}$ mole/cm² | 60[2] |
| 4 | Dodecylpenta(oxyethylene) Ether[1] | $3.31 \times 10^{-10}$ mole/cm² | 25 |
| | $C_{12}H_{25}O(CH_2CH_2O)_5H$ | $3.28 \times 10^{-10}$ mole/cm² | 40 |
| | (Comparative) | $3.16 \times 10^{-10}$ mole/cm² | 60[2] |
| 5 | Dodecylhepta(oxyethylene) Ether[1] | $2.90 \times 10^{-10}$ mole/cm² | 25 |
| | $C_{12}H_{25}O(CH_2CH_2O)_7H$ | $2.77 \times 10^{-10}$ mole/cm² | 40 |
| | (Comparative) | $2.71 \times 10^{-10}$ mole/cm² | 60[2] |
| 6 | Dodecylocta(oxvethylene) Ether[1] | $2.52 \times 10^{-10}$ mole/cm² | 25 |
| | $C_{12}H_{25}O(CH_2CH_2O)_8H$ | $2.46 \times 10^{-10}$ mole/cm² | 40 |
| | (Comparative) | $2.40 \times 10^{-10}$ mole/cm² | 60[2] |

[1]Rosen, M. J., in Surfactants and Interfacial Phenomena 2 ed., Wiley-Interscience Publication, 1989, pg 78; and Rosen, M. J., Cohen A. W., Dahanayake M. and Hua X. Y., J. Phys. Chem. 86, 541, 1981.
[2]This value was estimated by plotting temperature as function of surface excess concentration at surface saturation ($\Gamma_{max}$) and extrapolating a linear line at 60° C.

From the above table it can be seen that $C_8/C_{10}$ oxypropyl D-gluconamide has a small cross sectional area resulting in a tightly packed coherent interfacial film and strong effective interfacial absorption. The surface excess concentration at surface saturation ($\Gamma_{max}$) of this compound was found to be similar to dodecyltri(oxyethylene) ether (a common nonionic surfactant). This finding suggests that the heteroatom containing alkyl aldonamide compounds of the invention to be surface-active and so these compounds are expected to deliver favorable surfactant benefits.

Example 95

Area Per Molecule at the Interface

The area per molecule of a surfactant at the water/air interface provides information on the degree of packing and the orientation of the adsorbed surfactant molecule. While not wishing to be bound by theory, it is believed that surfactants that have small area per molecule values tend to pack more closely at the interface than those with large area per molecule values. From the surface excess concentration at surface saturation ($\Gamma_{max}$), the area per molecule ($a_m$) of $C_8/C_{10}$ oxypropyl D-gluconamide was determined and is given by:

$$a_m = 1 \times 10^{16}/N_{av}\Gamma_{max}$$

wherein:
$\Gamma_{max} = -1/2.303\ RT\ (\partial\gamma/\partial\log[Conc])_T$
$N_{av} = 6.0221 \times 10^{23}$ per gram mole (Avogadro's Number)
$T = 333.15$ K.

The area per molecule ($a_m$) of several surfactants were determined and are set forth below:

Area Per Molecule of Various Nonionic Surfactants at the Water/Air Interface

| Entry | Surfactant | $a_m$ | Temperature (°C.) |
|---|---|---|---|
| 1 | $C_8/C_{10}$ Oxypropyl D-Gluconamide | 43.1 Å$^2$ | 60 |
| 2 | Dodecyltri(oxyethylene) Ether[1] $C_{12}H_{25}O(CH_2CH_2O)_3H$ (Comparative) | 41.7 Å$^2$ 42.5 Å$^2$ 45.4 Å$^2$ | 25 40 60[2] |
| 3 | Dodecyltetra(oxyethylene) Ether[1] $C_{12}H_{25}O(CH_2CH_2O)_4H$ (Comparative) | 45.7 Å$^2$ 48.7 Å$^2$ 53.3 Å$^2$ | 25 40 60[2] |
| 4 | Dodecylpenta(oxyethylene) Ether[1] $C_{12}H_{25}O(CH_2CH_2O)_5H$ (Comparative) | 50.1 Å$^2$ 50.6 Å$^2$ 52.3 Å$^2$ | 25 40 60[2] |
| 5 | Dodecylhepta(oxyethylene) Ether[1] $C_{12}H_{25}O(CH_2CH_2O)_7H$ (Comparative) | 57.3 Å$^2$ 59.9 Å$^2$ 61.0 Å$^2$ | 25 40 60[2] |
| 6 | Dodecylocta(oxyethylene) Ether[1] $C_{12}H_{25}O(CH_2CH_2O)_8H$ (Comparative) | 66.0 Å$^2$ 67.4 Å$^2$ 69.0 Å$^2$ | 25 40 60[2] |

[1]Rosen, M. J., in Surfactants and Interfacial Phenomena 2 ed., Wiley-Interscience Publication, 1989, pg 78; and Rosen, M. J., Cohen A. W., Dahanayake M. and Hua X. Y., J. Phys. Chem. 86, 541, 1981.
[2]This value was estimated by plotting temperature as function of area per molecule ($a_m$) and extrapolating a linear line at 60° C.

From the above table it can be seen that $C_8/C_{10}$ oxypropyl D-gluconamide has a favorably small area per molecule value and is expected to pack tightly at the interface. The area per molecule ($a_m$) of this compound was found to be similar to dodecyltri(oxyethylene) ether. This finding suggests that the heteroatom compounds of the invention to be surface-active and so these compounds are expected to deliver favorable surfactant benefits.

Example 96

Micellar Shape and Structure

The shape or type of micelle produced by a surfactant in aqueous solution is an important criteria for delivering certain surfactant benefits such as viscosity, detergency, foaming, wetting or emulsification. At present there appears to be four major types of micelles a surfactant can form in aqueous solution;

(1) spherical micelles
(2) cylindrical rod-like micelles
(3) lamellar disk-like micelles
(4) vesicles or reversed micelles In aqueous media, surfactant molecules may be oriented in all these possible structures with their polar hydrophilic head groups pointed towards the aqueous phase and their nonpolar hydrophobic alkyl chain groups pointed away from it. In general, surfactants with large bulky or loosely packed hydrophilic groups and long, thin hydrophobic groups tend to form predominately spherical micelles whereas those with small or tightly packed hydrophilic groups and bulky hydrophobic groups tend to form predominately cylindrical or lamellar micelles. Changes in temperature, concentration and functional groups in the surfactant may all cause a change in size or shape of a micelle.

A theory of micellar structure, based upon the geometry of various micelle shapes and the space occupied by the surfactant has been disclosed by J. N. Israelachvili, D. J. Mitchell and B. W. Ninham in the J. Chem. Soc. Faraday Trans. 2, 1525, 72, (1976) which is given as the packing parameter (p).

$$p = V_T/l_c(a_m)$$

wherein;

$V_T = V_{(CH3)} + (n_c-1)V_{(CH2)}$ and represents the volume occupied by the hydrophobic groups in the micellar core at a given temperature.

$l_c = 1.50 + 1.26 \, n_c$ Å and represents the length of the hydrophobic group in the core.

$a_m$ = area per molecule or the cross-sectional area occupied by the hydrophilic group at the interface.

$V_{(CH3)} = 54.6 + 0.124 \, [T-298° \text{K.}]$ Å$^3$
$V_{(CH2)} = 26.9 + 0.0146 \, [T-298° \text{K.}]$ Å$^3$
$T = 333.15°$ K.

$n_c$ = total number of carbons in the alkyl chain.

Values obtained from the packing parameter (p) represent the following structures:

| Values of (p) | Structure of Micelle in Aqueous Media |
|---|---|
| 0.00 to 0.33 | Spherical |
| 0.33 to 0.50 | Cylindrical |
| 0.50 to 1.00 | Lamellar |
| >1.00 | Reversed |

The packing parameter (p) of $C_8/C_{10}$ oxypropyl D-Gluconamide was determined as follows:

The Packing Parameter of $C_8/C_{10}$ Oxypropyl D-Gluconamide

| Entry | Surfactant | $n_a^1$ | $V_T$(Å$^3$) | $l_c$(Å)$^1$ | $a_m$(Å$^2$) | p |
|---|---|---|---|---|---|---|
| 1 | $C_8/C_{10}$ Oxypropyl D-Gluconamide | 12.7 | 379.7 | 17.5 | 43.1 | 0.503 |

[1]This value represents the number atoms in the alkyl chain and assumes that one oxygen atom is equivalent to one methylene group.

Form the above table it can be seen that the packing parameter (p) for $C_8/C_{10}$ oxypropyl D-gluconamide was found to be 0.503 which means that this compound is predicted to form cylindrical to lamellar micelles. This finding suggests that the heteroatom containing alkyl aldonamide compounds of the invention to be surface-active and so these compounds are expected to deliver favorable surfactant benefits.

Examples 97–175

Compositions Comprising Heteroatom Containing Alkyl Aldonamide Compounds

The following examples represent personal product compositions comprising heteroatom containing alkyl aldonamide compounds according to the instant of the invention. Unless otherwise indicated, all percentages herein are by weight.

Examples 97–103

Prototype Bath Oil and Foaming Bath Oil Compositions Comprising Heteroatom Containing Alkyl Aldonamide Compounds

| Example Ingredients (By Weight) | 97 % | 98 % | 99 % | 100 % | 101 % | 102 % | 103 % |
|---|---|---|---|---|---|---|---|
| 1. Sodium Lauryl Sulfate (28%) | — | — | — | — | — | — | 22.0 |
| 2. Triethanol- amine Lauryl Sulfate (40%) | — | — | — | 40.0 | — | — | — |
| 3. Sodium | — | — | — | — | — | 50.0 | — |

Prototype Bath Oil and Foaming Bath Oil Compositions Comprising Heteroatom Containing Alkyl Aldonamide Compounds

| Example Ingredients (By Weight) | 97 % | 98 % | 99 % | 100 % | 101 % | 102 % | 103 % |
|---|---|---|---|---|---|---|---|
| laureth-2 Sulfate (26%) | | | | | | | |
| 4. Sodium Laureth-3 Sulfate (26%) | — | — | 50.0 | — | 40.0 | — | — |
| 5. Ammonium Laureth-1 Sulfate (25%) | — | — | — | — | 37.5 | — | — |
| 6. Disodium Ricinoleamido MEA Sulfosuccinate (40%) | — | — | — | 10.0 | — | — | — |
| 7. Disodium Oleamido PEG-2 Sulfosuccinate (35%) | — | — | — | — | — | — | 10.0 |
| 8. Lauryl Betaine (35%) | — | — | 5.0 | — | — | — | — |
| 9. Cocoamidopropyl Betaine (35%) | — | — | — | 4.0 | 5.0 | 10.0 | 20.0 |
| 10. Cocoamphocarboxyglycinate (38%) | — | — | — | — | — | 15.0 | — |
| 11. Soyaamidopropylethyldimonium Ethosulfate | — | — | — | — | — | — | 1.5 |
| 12. Caprylic/Capric Triglyceride | 14.0 | 10.0 | — | — | — | — | — |
| 13. Laureth-23 | — | — | — | — | — | 3.0 | — |
| 14. PEG-7 Glyceryl Cocoate | 37.0 | — | — | — | — | — | — |
| 15. PEG-25 Glyceryl Trioleate | — | 13.0 | — | — | — | — | — |
| 16. PEG-75 Lanolin | — | — | 10.0 | — | — | — | — |
| 17. PEG-40 Hydrogenated Castor Oil | 12.0 | — | — | — | — | — | — |
| 18. PEG-200 Glyceryl Tallowate | — | — | — | 2.0 | — | — | — |
| 19. PPG-12 PEG-65 Lanolin Oil | — | — | — | — | — | 1.0 | — |
| 20. Mineral Oil | — | 30.0 | — | — | — | — | — |
| 21. Avocado Oil | — | 20.0 | — | — | — | — | — |
| 22. C8/C10 Oxypropyl D-Gluconamide | — | — | 1.0 | — | 3.0 | 2.0 | 1.0 |
| 23. C8/C10 Oxypropyl D-Lactobionamide (50%) | — | — | 8.0 | — | 5.0 | — | 1.0 |
| 24. C12 Oxypropyl D-Lactobionamide (50%) | — | — | — | 2.0 | — | 0.5 | 1.0 |
| 25. Cocoaminopropyl D-Gluconamide (50%) | — | — | — | 1.0 | 1.0 | — | — |
| 26. Oleylaminopropyl D-Lactobionamide (50%) | 10.0 | — | — | — | — | 1.0 | 2.0 |
| 26b. Tallowaminopropyl D-Lactobionamide | — | 10.0 | — | — | — | — | — |
| 27. Myristyl Propionate | — | — | — | — | 1.5 | — | — |
| 28. Cetearyl Octanoate | 15.0 | — | — | — | — | — | — |
| 29. Isopropyl Myristate | — | 7.0 | — | — | — | — | — |
| 30. Acetylated Lanolin | — | — | 1.5 | — | — | — | — |
| 31. Sorbitol | — | — | — | — | — | 3.0 | — |
| 32. Dimethicone | — | 10.0 | — | — | — | — | — |
| 33. Bisabolol | 0.1 | — | — | — | — | — | — |
| 34. Panthenol (Provitamin B) | 0.2 | — | — | — | — | — | 0.2 |
| 35. Collagen Amino Acids | — | — | — | — | — | 0.5 | — |
| 36. TEA Coco Hydrolyzed Animal Protein | — | — | — | — | — | 1.5 | 1.1 |
| 37. Ethylene Glycol Monostearate | — | — | — | — | — | — | 0.5 |
| 38. Propylene Glycol | 0.8 | — | — | 0.5 | — | — | — |
| 39. Tetrasodium EDTA | — | — | 0.3 | 0.3 | 0.3 | — | 0.3 |
| 40. Disodium EDTA | — | — | — | — | — | 0.3 | — |
| 41. Methylchloroisothiazoline | — | — | 0.05 | — | — | — | — |
| 42. Methylisothiazoline | — | — | 0.05 | — | — | — | — |
| 43. DMDM Hydantoin | — | — | — | — | 0.3 | — | — |
| 44. Imidazolidinyl Urea | — | — | — | — | — | — | 0.1 |
| 45. Diazolidinyl Urea | — | — | — | — | — | — | 0.2 |
| 46. Methyl Paraben | — | — | — | 0.2 | — | 0.2 | — |
| 47. Propyl Paraben | — | — | — | 0.1 | — | — | — |
| 48. Iodopropynyl Butyl Carbamate | — | — | — | — | 0.2 | — | — |
| 49. Sodium Chloride (50%) Adjust Viscosity | — | — | q.s. | q.s. | q.s. | q.s. | q.s. |
| 50. Citric Acid (35%) pH to 5–7 | — | — | q.s. | q.s. | q.s. | q.s. | q.s. |
| 51. Dye (0.2%–1%) | — | — | q.s. | q.s. | q.s. | q.s. | q.s. |
| 52. Fragrance | q.s. | q.s. | q.s. | q.s. | q.s. | q.s. | q.s. |
| 53. Water | 10.9 | — | 24.1 | 39.9 | 6.2 | 12.0 | 39.1 |

Example 97

Foaming Emollient Bath Oil with Vitamins

Container A is charged with 12, 14, 17, 15, 33, 34 and 38 which is mixed thoroughly. Container B is charged with 53 and 26 which is heated to 60° C. with moderate stirring. Slowly add B to A while stirring. Mix thoroughly, heat if necessary and discharge when homogeneous.

Example 98

Emollient Bath Oil with Silicone Fluid

Container A is charged with 12, 15, 20, 21, 29, 32 and 26b which is heated to 40° C. with moderate stirring. Mix thoroughly, cool down the mixture to room temperature and discharge when homogeneous.

Example 99

Foaming Emollient Bath Cream

Container A is charged with 4, (75% of 53), 8, 23, 22 and 39 which is heated to 45° C. with moderate stirring. Container B is charged with 16, 30 (the rest of 53), 41 and 42 which is mixed thoroughly. Add 51, 52, 49 and 53. Mix thoroughly. Slowly add B to A while stirring. Mix thoroughly, heat if necessary and discharge when homogeneous.

Example 100

High Foaming Skin Conditioning Bubble Bath

Container A is charged with 53, 2, 9, 39, 24, 25 and 18 which is heated to 75° C. with moderate stirring. When homogeneous, cool down the mixture to 45° C. and add 6. Mix thoroughly. Add 37, 46, 47, 52, 51, 49 and 50. Mix thoroughly, cool down the mixture to room temperature and discharge when homogeneous.

Example 101

High Foaming Mild Bubble Bath

Container A is charged with 4, 5, 9 and 27 which is mixed with moderate stirring. Add 23, 25 and 22. Mix thoroughly. Add 53, 39, 43, 48, 52, 50, 51 and 49. Mix thoroughly, heat if necessary and discharge when homogeneous.

Example 102

High Foaming Skin Conditioning Bubble Bath Concentrate with Protein

Container A is charged with 53, 50, 22, 24, 26, 46, 40 and 36 which is heated to 55° C. and stirred slowly. Add 31, 9 and 10. Mix thoroughly. Container B is charged with 13, 52, 35 and 19 with is heated to 55° C. with moderate stirring. Slowly add B to A while stirring. Add, 31, 9 and 10. Mix thoroughly, cool the mixture to room temperature and discharge when homogeneous.

Example 103

High Foaming Mild Bubble Bath with Protein and Vitamins

Container A is charged with 53, 1, 7, 9, 11, 22, 23, 24 and 26 which is heated to 60° C. with moderate stirring. Add 34, 36, 39 and 37. Mix thoroughly. Add 44, 45, 50, 51, 52 and 49. Mix thoroughly, cool the mixture to room temperature and discharge when homogeneous.

Examples 104–110

Prototype Shower Gel compositions Comprising Heteroatom Containing Alkyl Aldonamide Compounds

| Example Ingredients (By Weight) | 104 % | 105 % | 106 % | 107 % | 108 % | 109 % | 110 % |
|---|---|---|---|---|---|---|---|
| 1. Sodium Lauryl Sulfate (28%) | 37.5 | — | — | — | — | — | — |
| 2. Triethanolamine Lauryl Sulfate (40%) | — | — | 22.5 | — | — | — | — |
| 3. Sodium laureth-2 Sulfate (28%) | — | 37.7 | — | 35.0 | 30.0 | 50.0 | 18.0 |
| 4. Sodium laureth-3 Sulfate (26%) | — | — | 18.8 | — | — | — | — |
| 5. Disodium Lauryl Sulfosuccinate (40%) | — | — | — | — | — | — | 5.0 |
| 6. Coco Betaine (35%) | — | — | — | — | 7.0 | — | — |
| 7. Cocoamidopropyl Betaine (35%) | — | 10.0 | 6.0 | 5.0 | — | 10.0 | — |
| 8. Disodium Cocoamphodiacetate (25%) | — | — | — | — | — | — | 8.0 |
| 9. PEG-4 Glyceryl Caprylate/Caprate | — | — | 0.4 | — | — | — | — |
| 10. PEG-8 Glyceryl Caprylate/Caprate | — | — | 1.5 | — | — | — | — |
| 11. PEG-7 Glyceryl Cocoate | — | — | — | — | — | — | 2.0 |
| 12. PEG-12 Glyceryl Laurate | 5.0 | — | — | — | — | — | — |
| 13. PEG-30 Glyceryl Cocoate | — | — | — | — | — | — | 4.0 |
| 14. PEG-200 Glyceryl Palmitate | — | — | — | — | — | — | 4.0 |
| 15. Glyceryl Laurate | 1.0 | — | — | — | — | — | — |
| 16. C8/C10 Oxypropyl D-Gluconamide | 1.0 | — | — | — | 1.0 | — | 1.0 |
| 17. C12 Oxypropyl D-Gluconamide | — | 1.0 | — | — | — | — | — |
| 18. C8/C10 Oxypropyl D-Lactobionamide (50%) | 2.0 | 2.0 | — | — | 2.0 | 3.5 | 1.0 |
| 19. C12-C15 Oxypropyl D-Lactobionamide (50%) | — | — | 6.0 | 3.0 | — | — | — |
| 20. C12-C15 Oxypropyl-aminopropyl D-Gluconamide | — | — | — | 1.0 | — | — | — |
| 21. Cocoaminopropyl D-Gluconamide (50%) | — | — | — | — | 1.0 | — | 1.0 |
| 22. Oleylaminopropyl D-Lactobionamide (50%) | — | — | — | — | — | 1.0 | — |
| 23. Steramidopropyl PG Dimonium Chloride | — | — | — | 2.0 | — | — | — |
| 24. Panthlenyl Hydroxypropyl Steardimonium Chloride | — | — | — | — | 2.0 | — | — |
| 25. Acetamide MEA | — | — | — | 1.0 | — | — | — |
| 26. Lactamide MEA | — | — | — | 1.0 | — | — | 2.0 |
| 27. Sodium Pyrrolidone Carboxylic Acid | — | — | — | — | 0.3 | — | — |
| 28. Dimethicone | — | 0.5 | — | — | — | — | — |
| 29. Potassium Coco Hydrolyzed Animal Protein | 15.0 | — | — | — | — | — | — |
| 30. Hydrolyzed Animal Protein | 5.0 | — | — | — | — | — | — |
| 31. Aloe Vera Gel | — | — | 3.0 | — | — | 3.0 | — |
| 32. Hena Extract | — | — | — | — | — | 0.5 | — |

-continued

Prototype Shower Gel compositions Comprising Heteroatom Containing Alkyl Aldonamide Compounds

| Example Ingredients (By Weight) | 104 % | 105 % | 106 % | 107 % | 108 % | 109 % | 110 % |
|---|---|---|---|---|---|---|---|
| 33. Tocopherol Acetate (Vitamin E) | — | 0.5 | — | — | — | — | 1.0 |
| 34. Panthenol (Vitamin B5) | 0.5 | — | — | — | — | — | — |
| 35. Ethylene Glycol Monostearate | — | — | 0.6 | — | — | — | — |
| 36. Tetrasodium EDTA | — | — | — | — | 0.1 | — | — |
| 37. Butylated Hydroxytoluene | — | — | — | — | — | 0.1 | — |
| 38. Glycerin | — | — | — | — | — | — | 0.5 |
| 39. Propylene Glycol | 0.5 | — | — | — | 0.5 | — | — |
| 40. Methylchloro-isothiazoline | — | — | 0.07 | — | — | 0.06 | — |
| 41. Methylisothiazoline | — | — | 0.03 | — | — | 0.04 | — |
| 42. DMDM Hydantoin | — | 0.3 | — | — | — | — | — |
| 43. Diazolidinyl Urea | — | — | — | 0.2 | — | — | — |
| 44. Methyl Paraben | 0.2 | — | — | — | 0.2 | — | 0.2 |
| 45. Propyl Paraben | 0.1 | — | — | — | 0.1 | — | 0.1 |
| 46. Sodium Chloride (50%) Adjust Viscosity | q.s. | q.s. | q.s. | q.s. | q.s. | q.s. | q.s. |
| 47. Citric Acid (35%) pH to 5-7 | q.s. | q.s. | 0.3 | q.s. | q.s. | 0.4 | q.s. |
| 48. Dye (0.2%–1%) | q.s. | q.s. | q.s. | q.s. | q.s. | q.s. | q.s. |
| 49. Fragrance | q.s. | q.s. | q.s. | q.s. | q.s. | q.s. | q.s. |
| 50. Water | 32.2 | 48.0 | 40.8 | 51.8 | 55.8 | 31.4 | 52.2 |

Example 104

A Clear Shower Gel with Protein and Vitamins

Container A is charged with 1 and 15 which is heated to 60° C. with moderate stirring. Add 50, 29, 30, 16, 18, 12, 39, 44 and 45. Mix thoroughly. Add 34, 49, 48, 47 and 46. Mix thoroughly, cool the mixture to room temperature and discharge when homogeneous.

Example 105

A Clear Conditioning Shower Gel with Silicone and Vitamins

Container A is charged with 3, 49, 17 and 18 which is heated to 60° C. with moderate strirring. Container B is charged with 50, 7, 28 and 33 which is stirred moderately. Slow add B to A while stirring. Add 42, 48, 47 and 46. Mix thoroughly, cool the mixture to room temperature and discharge when homogeneous.

Example 106

A Pearlescent Conditioning Shower Gel with Aloe

Container A is charged with 50, 2, 4, 31, 40, 41, 47, 17 and 19 which is heated to 60° C. with moderate strirring. Container B is charged with 9, 10 and 35 which is heated to 60° C. with moderate strirring. Slow add B to A while stirring. Add 49, 48 and 46. Mix thoroughly, cool the mixture to room temperature and discharge when homogeneous.

Example 107

A Clear Conditioning Shower Gel

Container A is charged with 50, 3, 7, 19, 20, 25 and 26 which is heated to 60° C. with moderate stirring. Add 23. Mix thoroughly. Add 43, 49, 48, 47 and 46. Mix thoroughly, cool the mixture to room temperature and discharge when homogeneous.

Example 108

A Clear Conditioning Shower Gel

Container A is charged with 50, 3, 27, 39, 44, 45 and 36 which is heated to 60° C. with moderate stirring. Add 6, 16, 18 and 21. Mix thoroughly. Add 49, 48 and 47. Mix thoroughly. Add 24. Mix thoroughly. Add 46. Mix thoroughly, cool the mixture to room temperature and discharge when homogeneous.

Example 109

A Clear Conditioning Shower Gel with Aloe and Herbal Extracts

Container A is charged with 50, 3, 7 and 9 which is heated to 60° C. with moderate stirring. Add 18, 22, 32 and 37. Mix thoroughly. Add 40, 41, 49, 48, 47 and 46. Mix thoroughly, cool the mixture to room temperature and discharge when homogeneous.

Example 110

A Clear Conditioning Shower Gel with Vitamins

Container A is charged with 50, 3, 5, 8, 11, 13, 14, 16, 18, and 21 which is heated to 60° C. with moderate stirring. Add 38, 26 and 33. Mix thoroughly. Add 44, 45, 49, 48, 47 and 46. Mix thoroughly, cool the mixture to room temperature and discharge when homogeneous.

Examples 111–117

Prototype Body Shampoo Compositions Comprising Heteroatom Containing Alkyl Aldonamide Compounds

| Ingredients (By Weight) | Example 111 % | 112 % | 113 % | 114 % | 115 % | 116 % | 117 % |
|---|---|---|---|---|---|---|---|
| 1. Sodium Lauryl Sulfate (28%) | — | 23.3 | — | — | — | — | — |
| 2. Ammonium Lauryl Sulfate (28%) | — | — | — | — | 35.0 | — | — |
| 3. Diethanolamine Lauryl Sulfate (35%) | — | — | 14.0 | — | — | — | — |
| 4. Triethanolamine Lauryl Sulfate (40%) | — | — | 15.0 | — | — | — | — |
| 5. Sodium Laureth-2 Sulfate (28%) | — | — | — | — | — | 30.0 | 25.0 |
| 6. Ammonium Laureth-2 Sulfate (30%) | — | — | — | 30.0 | 15.0 | — | — |
| 7. Sodium C14–C16 α-Olefin Sulfonate (40%) | 35.0 | — | 20.0 | — | — | — | — |
| 8. Sodium Methyl Cocoyl Taurate (24%) | 12.0 | — | — | — | — | — | — |
| 9. Disodium Undecylenamido MEA Sulfosuccinate | — | 3.0 | — | — | — | — | — |
| 10. Disodium Laureth Sulfosuccinate (40%) | — | 9.7 | — | — | — | — | — |
| 11. Potassium C9–C15 Alkyl Phosphate | — | — | — | — | — | 12.0 | 10.0 |
| 12. Triethanolamine Oleate | — | — | 0.5 | — | — | — | — |
| 13. Sodium Coco- | — | — | — | — | — | 10.0 | 8.0 |

Prototype Body Shampoo Compositions Comprising Heteroatom Containing Alkyl Aldonamide Compounds

| Ingredients (By Weight) | 111 % | 112 % | 113 % | 114 % | 115 % | 116 % | 117 % |
|---|---|---|---|---|---|---|---|
| amphoacetate (35%) | | | | | | | |
| 14. Lauramidopropyl Betaine (30%) | — | — | — | 10.0 | — | — | — |
| 15. Cocoamidopropyl Betaine (35%) | 10.0 | 10.0 | 6.0 | 7.0 | — | — | — |
| 16. C8–C18 Alkyl Polyglycoside (50%) | — | 3.0 | 10.0 | — | — | — | 5.0 |
| 17. PEG-55 Propylene Glycol Oleate | — | — | — | 2.0 | — | — | — |
| 18. PEG-150 Distearate | 1.0 | — | — | — | — | — | — |
| 19. Oleth 20 | — | — | 0.2 | — | — | — | — |
| 20. C8/C10 Oxypropyl D-Gluconamide | 2.0 | — | — | — | 1.0 | 1.0 | 0.5 |
| 21. C12 Oxypropyl D-Gluconamide | — | 0.5 | — | — | — | — | — |
| 22. C8/C10 Oxypropyl D-Lactobionamide (50%) | — | — | 9.0 | 6.0 | 4.0 | 3.5 | — |
| 23. C12 Oxypropyl D-Mattobionamide (50%) | 8.0 | 4.0 | — | — | 5.0 | — | 2.5 |
| 24. C12–C15 Oxy-propylaminopropyl D-Gluconamide | — | 0.5 | — | — | — | — | 0.5 |
| 25. Cocoaminopropyl D-Gluconamide (50%) | — | — | — | 0.5 | — | — | — |
| 26. Oleylaminopropyl D-Lactobionamide (50%) | — | — | — | 0.5 | — | — | — |
| 27. Propyltrimonium Hydrolyzed Animal Protein | — | — | — | — | 5.0 | — | — |
| 28. Polyquaternium-7 | — | — | 0.2 | — | — | — | — |
| 29. Polyquaternium-10 | — | — | — | — | — | 0.5 | 0.5 |
| 30. Polyquaternium-11 | 2.5 | — | — | — | — | — | — |
| 31. Butoxyethyl Stearate | — | — | 0.2 | — | — | — | — |
| 32. Glyceryl Laurate | — | — | — | — | — | 1.0 | 0.8 |
| 33. Ethylene Glycol Monostearate | — | 1.0 | — | — | — | — | — |
| 34. Ethylene Glycol Distearate | 2.0 | — | — | — | — | 3.2 | 3.0 |
| 35. Hydroxypropyl-methyl Cellulose | — | — | — | — | 0.5 | — | — |
| 36. Hydrolyzed Animal Protein | — | — | — | 0.2 | — | — | — |
| 37. Sodium Lactate | — | — | — | 0.1 | — | — | — |
| 38. Fructose | — | — | — | 0.1 | — | — | — |
| 39. Urea | — | — | — | 0.1 | — | — | — |
| 40. Niacinamide (Vitamin B3) | — | — | — | 0.1 | — | — | — |
| 41. Sodium Pyrrolidone Carboxylic Acid | — | — | — | 0.1 | — | — | — |
| 42. Dimethicone | — | — | — | 0.5 | — | — | — |
| 43. Tetrasodium EDTA | — | — | 0.1 | 0.1 | — | — | — |
| 44. SD Alcohol 40-B | — | — | — | — | — | 2.8 | 2.8 |
| 45. Sodium Benzoate | — | — | — | 0.1 | — | — | — |
| 46. Lauric Acid | — | — | — | — | — | 4.5 | 4.0 |
| 47. Glycerine | — | 2.0 | — | — | — | — | — |
| 48. Propylene Glycol | 0.5 | — | — | — | 2.0 | 1.8 | 1.5 |
| 49. Butylated Hydroxytoluene | — | — | — | — | — | 0.2 | 0.2 |
| 50. Sucrose Octaacetate | — | — | — | — | — | 0.1 | 0.2 |
| 51. Methylchloroiso-thiazoline | — | 0.05 | — | — | — | — | — |
| 52. Methylisothiazo-line | — | 0.05 | — | — | — | — | — |
| 53. DMDM Hydantoin | — | — | 0.2 | — | — | — | — |
| 54. Iodopropynyl Butyl Carbamate | — | — | 0.1 | — | — | — | — |
| 55. Imidazolidinyl Urea | — | — | — | — | 0.3 | — | — |
| 56. Diazolidinyl Urea | 0.1 | — | — | — | — | — | — |
| 57. Methyl Paraben | 0.2 | — | — | 0.3 | 0.2 | — | — |
| 58. Propyl Paraben | 0.1 | — | — | 0.1 | 0.1 | — | — |
| 59. Sodium Chloride (50%) Adjust Viscosity | q.s. | q.s. | q.s. | — | — | q.s. | q.s. |
| 60. Ammonium Cloride (30%) Adjust Viscosity | — | — | — | q.s. | q.s. | — | — |
| 61. Lactic Acid (35%) pH to 5–7 | — | — | — | q.s. | q.s. | — | — |
| 62. Citric Acid (35%) pH to 5–7 | q.s. | q.s. | q.s. | — | — | q.s. | q.s. |
| 63. Dye (0.2%–1%) | q.s. | q.s. | q.s. | q.s. | q.s. | — | — |
| 64. Fragrance | q.s. | q.s. | q.s. | q.s. | q.s. | q.s. | q.s. |
| 65. Water | 26.6 | 42.9 | 24.5 | 42.2 | 31.9 | 29.4 | 35.5 |

Example 111

A Pearlescent Conditioning Body Shampoo

Container A is charged with 65, 7, 8, 18, 34, 23, 20, 30 and 15 which is heated to 75° C. with moderate stirring. Cool to 40° C. Add 48, 56, 57, 58, 64, 63, 62 and 59. Mix thoroughly, cool the mixture to room temperature and discharge when homogeneous.

Example 112

A Pearlescent Body Shampoo

Container A is charged with 65, 1 and 33 which is heated to 65° C. with moderate stirring. Add 16, 23, 24, 21 and 47. Mix thoroughly. Cool to 40° C. Add 9 and 10. Mix thoroughly. Add 15, 51, 52, 64, 63, 62 and 59. Mix thoroughly, cool the mixture to room temperature and discharge when homogeneous.

Example 113

A Clear Conditioning Body Shampoo

Container A is charged with 65, 7, 4, 3, 22, 16 and 15 which is heated to 80° C. with moderate stirring. Add 12, 31, 19 and 28. Mix thoroughly. Add 43, 53, 54 and 63. Mix thoroughly. Cool to 40° C. Add 64, 62 and 59. Mix thoroughly, cool the mixture to room temperature and discharge when homogeneous.

Example 114

A Clear Conditioning Body Shampoo with Protein

Container A is charged with 65, 43, 6, 15, 14, 17, 22, 25 and 26 which is heated to 65° C. with moderate stirring. Add 42. Mix thoroughly. Cool to 40° C. Add 36, 37, 38, 39, 40, 41 and 45. Mix thoroughly. Add 57, 58, 64, 63, 60 and 61. Mix thoroughly, cool the mixture to room temperature and discharge when homogeneous.

Example 115

A Clear Conditioning Body Shampoo with Protein

Container A is charged with 65 and 35 which is heated to 80° C. with rapid stirring. When clear, add 48, 57 and 58.

Mix thoroughly. Cool to 65° C. Add 2, 6, 22, 23 and 20. Mix thoroughly. Add 27, 55, 64, 63, 60 and 61. Mix thoroughly, cool the mixture to room temperature and discharge when homogeneous.

Example 116

A Pearlescent Conditioning Body Shampoo

Container A is charged with 65, 5, 13 and 11 which is heated to 70° C. with moderate stirring. Add 22 and 20. Mix thoroughly. Add 29, 44, 46, 48 and 32. Mix thoroughly. Add 34, 49, 50, 64, 62 and 59. Mix thoroughly, cool the mixture to room temperature and discharge when homogeneous.

Example 117

A Pearlescent Conditioning Body Shampoo

Container A is charged with 65, 5, 13 16 and 11 which is heated to 70° C. with moderate stirring. Add 23, 24 and 20. Mix thoroughly. Add 29, 44, 46, 48 and 32. Mix thoroughly. Add 34, 49, 50, 64, 62 and 59. Mix thoroughly, cool the mixture to room temperature and discharge when homogeneous.

Examples 118–124

Prototype Liquid Soap Compositions Comprising Heteroatom Containing Alkyl Aldonamide Compounds

| Ingredients (By Weight) | 118 % | 119 % | 120 % | 121 % | 122 % | 123 % | 124 % |
|---|---|---|---|---|---|---|---|
| 1. Sodium Lauryl Sulfate (28%) | — | — | — | 20.0 | — | — | — |
| 2. Triethanolamine Lauryl Sulfate (40%) | — | 5.0 | — | — | — | — | — |
| 3. Sodium laureth-2 Sulfate (28%) | 3.1 | — | — | 25.0 | 25.0 | — | — |
| 4. Sodium laureth-3 Sulfate (26%) | — | — | — | — | — | 20.0 | — |
| 5. Sodium C14–C16 α-Olefin Sulfonate (40%) | — | — | 15.0 | — | — | 10.0 | 20.0 |
| 6. Sodium Cocoyl Isethionate | 8.3 | 11.0 | — | — | — | — | 10.0 |
| 7. Sodium Lauryl Sarcosinate (30%) | — | — | — | — | — | — | — |
| 8. Sodium Dodecyl Benzene Sulfonate (55%) | 3.4 | 3.6 | — | — | — | — | — |
| 9. Disodium Cocoamido MEA Sulfosuccinate | 1.6 | — | — | — | — | — | — |
| 10. Disodium Oleamido MEA Sulfosuccinate | 1.6 | — | — | — | — | — | — |
| 11. Disodium Laureth Sulfosuccinate (40%) | — | — | 15.0 | — | — | — | — |
| 12. Sodium Cocoate (82:18) | 1.9 | 2.4 | — | — | — | — | — |
| 13. Triethanolamine Lauryl Phosphate | — | — | — | 4.0 | — | — | — |
| 14. Cocoamidopropyl Betaine (35%) | — | — | 3.0 | — | 8.0 | 7.0 | 7.0 |
| 15. PEG-55 Propylene Glycol Oleate | — | — | — | 2.0 | — | — | — |
| 16. C8/C10 Oxypropyl D-Gluconamide | — | — | — | — | 3.0 | 2.0 | — |
| 17. C12 Oxypropyl D-Gluconamide | — | — | — | — | — | 1.0 | — |
| 18. N-Gluconyl C12 Di(oxyethyl) Glycinate (50%) | — | 6.0 | — | — | 1.0 | — | 2.0 |
| 19. C8/C10 Oxypropyl D-Lactobionamide (50%) | 8.0 | — | 6.0 | — | 3.0 | — | 2.0 |
| 20. C12 Oxypropyl D-Maltobionamide (50%) | — | — | — | 5.0 | — | — | 2.0 |
| 21. C12–C15 Oxy-propylaminopropyl D-Gluconamide | — | — | — | — | — | — | — |
| 22. Cocoaminopropyl D-Gluconamide (50%) | — | — | 4.0 | — | — | — | — |
| 23. Oleylaminopropyl D-Lactobionamide (50%) | — | — | — | — | — | 1.0 | — |
| 24. Polyquaternium-4 | — | — | — | — | — | 0.5 | — |
| 25. Polyquaternium-11 | — | — | 2.0 | — | — | — | 1.0 |
| 26. Stearic Acid | 7.9 | 8.0 | — | — | — | — | — |
| 27. Sodium Isethionate | 3.9 | 5.0 | — | — | — | — | — |
| 28. Ethylene Glycol Monostearate | — | — | 1.0 | 1.0 | 1.0 | 2.0 | — |
| 29. Phenoxyethanol | — | — | 1.0 | — | — | — | — |
| 30. Dimethicone | — | — | — | — | 0.6 | — | — |
| 31. Panthenol (Vitamin B5) | — | — | — | 2.0 | — | — | — |
| 32. Tocopheryl Acetate/Linoleate (Vitamin E) | — | — | — | 2.0 | — | — | — |
| 33. Butylated Hydroxytoluene | 0.01 | 0.01 | — | — | — | 0.1 | — |
| 34. Carboxymethyl Cellulose | — | — | — | 1.5 | — | — | — |
| 35. Hydroxyethyl Cellulose | — | — | — | — | — | — | 0.7 |
| 36. Guar Gum | — | — | — | — | — | — | 0.3 |
| 37. Bentone EW Clay (1.5%) | 24.0 | — | — | — | — | — | — |
| 38. Disodium EDTA | — | — | — | — | — | — | 0.2 |
| 39. Trisodium EDTA | 0.02 | 0.02 | — | — | — | — | — |
| 40. Tetrasodium EDTA | — | — | — | — | 0.1 | 0.2 | — |
| 41. Disodium (1-Hydroxyethylidene) Biphosphate | 0.02 | 0.02 | — | — | — | — | — |
| 42. Propylene Glycol | 7.0 | 10.0 | — | — | — | 0.5 | — |
| 43. Methylchloroiso-thiazoline | — | — | — | — | 0.1 | — | — |
| 44. Methylisothiazo-line | — | — | — | — | 0.05 | — | — |
| 45. DMDM Hydantoin | — | — | 0.2 | — | — | — | — |
| 46. Iodopropynyl Butyl Carbamate | — | — | 0.1 | — | — | — | — |
| 47. Imidazolidinyl Urea | — | — | — | 0.3 | — | — | — |
| 48. Diazolidinyl Urea | — | — | — | — | — | 0.1 | — |
| 49. Methyl Paraben | 0.2 | 0.2 | — | 0.2 | — | 0.2 | 0.2 |
| 50. Propyl Paraben | 0.1 | 0.1 | — | 0.1 | — | 0.1 | — |
| 51. N-(3-Chlorallyl) Hexaminium Chloride | 0.1 | 0.1 | — | — | — | — | — |
| 51b. Triclosan | — | — | — | — | — | 0.5 | — |
| 52. Sodium Chloride (50%) Adjust Viscosity | q.s. | — | q.s. | q.s. | q.s. | q.s. | q.s. |
| 53. Lactic Acid (35%) pH to 5–7 | — | q.s. | — | — | q.s. | — | — |
| 54. Citric Acid (35%) pH to 5–7 | q.s. | — | q.s. | q.s. | — | q.s. | q.s. |
| 55. Dye (0.2%–1%) | — | — | q.s. | q.s. | q.s. | q.s. | q.s. |
| 56. Fragrance | q.s. | q.s. | q.s. | q.s. | q.s. | q.s. | q.s. |
| 57. Water | 28.85 | 48.55 | 52.7 | 38.9 | 56.15 | 64.8 | 54.6 |

Example 118

A Pearlescent Liquid Soap Composition

Container A is charged with 42, 8 and 3 which is heated to 32° C. with slow stirring. Container B is charged with 57 which is heated to 82° C. Slowly add A to B with mixing followed by the addition of 37. Mix thoroughly. Add 19, 9, 10, 6 and 12. Mix thrughly and cool to 74° C. Add 49, 50, 39, 41 and 26. Mix thoroughly and cool to 46° C. Add 51, 56, 33, 27, 54 and 52. Mix thoroughly, cool the mixture to room temperature and discharge when homogeneous.

Example 119

A Pearlescent Liquid Soap Composition

Container A is charged with 42, 27, 8 and 2 which is heated to 32° C. with slow stirring. Container B is charged with 57 which is heated to 82° C. Slowly add A to B with mixing followed by the addition of 6. Mix thoroughly. Add 12, 18, 49, 50, 39 and 41. Mix throughly and cool to 74° C. Add 26. Mix thoroughly and cool to 46° C. Add 51, 33, 56 and 53. Mix thoroughly, cool the mixture to room temperature and discharge when homogeneous.

Example 120

A Pearlescent Conditioning Liquid Soap Composition

Container A is charged with 57, 11, 5, 19 and 22 which is heated to 75° C. with moderate stirring. Add 14, 25, 28 and 29. Mix thoroughly. Add 45, 46, 56, 55, 54 and 52. Mix thoroughly, cool the mixture to room temperature and discharge when homogeneous.

Example 121

A Pearlescent Liquid Soap Composition with Vitamins

Container A is charged with 3, 1, 20, 28 and 34 which is heated to 75° C. with moderate stirring. Container B is charged with 57, 13, 31 and 32 which is heated to 55° C. with moderate stirring. Slowly add A to B while stirring. Add 47, 49, 50, 56, 55, 54 and 52. Mix thoroughly, cool the mixture to room temperature and discharge when homogeneous.

Example 122

A Pearlescent Conditioning Liquid Soap Composition

Container A is charged with 57, 40, 14, 3 and 15 which is heated to 65° C. with moderate stirring. Add 19, 18, 16, 30 and 28. Mix thoroughly. Add 43, 44, 56, 55, 53 and 52. Mix thoroughly, cool the mixture to room temperature and discharge when homogeneous.

Example 123

A Pearlescent Antibacterial Conditioning Liquid Soap Composition

Container A is charged with 57 and 24 which is heated to 65° C. with moderate stirring. Add 4, 5, 28, 14, 17, 16 and 23. Mix thoroughly. Add 40, 33, 42, 48, 49, 51b and 50. Mix thoroughly. Add 56, 55, 54 and 52. Mix thoroughly, cool the mixture to room temperature and discharge when homogeneous.

Example 124

A Transparent Conditioning Liquid Soap Composition

Container A is charged with 57, 34 and 36 which is heated to 65° C. with moderate stirring. Container B is charged with 5, 7, 49, 18, 19 and 20 which is heated to 80° C. with moderate stirring. Slowly add B to A while stirring. Add 38, 25, 56, 55, 54, and 52. Mix thoroughly, cool the mixture to room temperature and discharge when homogeneous.

Examples 125–131

Prototype Toilet and Syndet Soap Bar Compositions Comprising Heteroatom Containing Alkyl Aldonamide Compounds

| Ingredients (By Weight) | 125 % | 126 % | 127 % | 128 % | 129 % | 130 % | 131 % |
|---|---|---|---|---|---|---|---|
| 1. Sodium Cocoyl Isethionate | 44.0 | 47.0 | 40.5 | — | 21.7 | — | — |
| 2. Sodium Cocoyl Sarcosinate | — | — | — | — | — | 13.0 | — |
| 3. Disodium Cocoamido MEA Sulfosuccinate | 3.5 | 6.0 | — | — | — | — | — |
| 4. Triethanolamine lauryl Sulfate | — | — | — | — | — | 18.0 | 18.0 |
| 5. Sodium Tallowate/ Cocoate (82/18) | — | — | — | 59.9 | 50.7 | — | — |
| 6. Sodium Tallowate/ Palm Kernelate (80/20) | — | — | — | 13.9 | — | — | — |
| 7. Sodium Stearate | — | — | — | — | — | 24.0 | 24.0 |
| 8. Cocoamidopropyl Betaine | 3.5 | 1.0 | — | — | — | — | — |
| 9. PEG-46 Palm Kernel Glycerides | — | — | — | — | — | 10.0 | — |
| 10. PPG-12/PEG-65 Lanolin Oil | — | — | — | — | — | — | 5.0 |
| 11. PEG-150 | 0.5 | — | — | — | — | — | — |
| 12. C8/C10 Oxypropyl D-Gluconamide | — | — | 10.0 | 1.0 | — | — | 2.0 |
| 13. C12 Oxypropyl D-Gluconamide | — | 2.0 | — | — | — | — | 0.5 |
| 14. N-Gluconyl C12 Di(oxyethyl) Glycinate | — | — | — | 1.0 | — | — | 1.5 |
| 15. C8/C10 Oxypropyl D-Lactobionamide | 3.0 | — | 14.5 | 5.0 | 3.0 | — | 3.0 |
| 16. C12 Oxypropyl D-Lactobionamide | — | — | 6.5 | — | — | 4.5 | 5.0 |
| 17. C12 Oxypropyl D-Maltobionamide | 5.0 | 5.0 | 7.5 | — | 3.0 | 4.5 | 4.4 |
| 18. C12–C15 Oxypropylaminopropyl D-Gluconamide | — | — | — | — | — | — | 0.1 |
| 19. Cocoaminopropyl D-Gluconamide | — | — | — | 0.2 | — | — | — |
| 20. Tallowaminopropyl D-Lactobionamide | — | — | — | 0.2 | — | — | — |
| 21. Tallow/Coconut Fatty Acid | 27.9 | 33.8 | — | — | 1.3 | — | — |
| 22. Stearic acid | — | — | 13.5 | 9.0 | 7.0 | — | — |
| 23. Glycerine | — | — | — | 1.0 | — | 11.0 | 15.0 |
| 24. Propylene Glycol | — | — | — | — | — | 10.0 | 15.0 |
| 25. Dextrin | 1.0 | — | — | — | — | — | — |
| 26. Urea | — | — | — | — | — | 2.0 | — |
| 27. Kelp Extract | — | — | — | — | — | — | 2.0 |
| 28. Tocopheryl Acetate (Vitamin E) | — | — | — | — | — | — | 0.5 |
| 29. Sodium Isethionate | 5.0 | 5.2 | — | — | 5.0 | — | — |
| 30. Sodium Chloride | 0.5 | 0.5 | 0.5 | 0.5 | 0.4 | — | — |
| 31. Titanium Dioxide | 0.5 | 0.5 | 0.2 | 0.3 | 0.3 | 0.2 | 0.3 |

Prototype Toilet and Syndet Soap Bar Compositions Comprising Heteroatom Containing Alkyl Aldonamide Compounds

| Ingredients (By Weight) | 125 % | 126 % | 127 % | 128 % | 129 % | 130 % | 131 % |
|---|---|---|---|---|---|---|---|
| 32. Triclosan | — | — | 0.5 | — | 0.5 | — | — |
| 33. Disodium Phosphate | 0.2 | 0.2 | 0.3 | 0.2 | 0.2 | 0.3 | 0.2 |
| 34. Tetrasodium ETDA | 0.03 | 0.03 | 0.03 | 0.03 | 0.04 | 0.05 | 0.03 |
| 35. Trisodium Etidronate | 0.02 | — | 0.02 | — | 0.02 | 0.04 | — |
| 36. Tetrasodium Etidronate | — | 0.04 | — | 0.03 | — | — | 0.03 |
| 37. Butylated Hydroxytoluene | 0.02 | 0.02 | 0.02 | 0.05 | 0.02 | 0.03 | 0.03 |
| 38. Fragrance | 1.0 | 1.0 | 1.0 | 3.0 | 1.0 | 1.0 | 2.0 |
| 39. Water | 4.33 | 4.71 | 4.93 | 4.69 | 5.82 | 1.38 | 1.41 |

Example 125

A Mild Syndet Bar Composition

A Brabender Prep-Mixer is charged with 1, 21, 39 and 30 which is heated to 80° C. with moderate stirring. Add 29, 33, 34, 35 and 37. Mix thoroughly. Add 3, 8 and 11. Mix thoroughly. Add 15, 17 and 25. Mix thoroughly. Add 31 and 38. Mix thoroughly, cool the mixture to room temperature and discharge when homogeneous. Place under a moderate vacuum and dry. Press into bars using a Carver Hydraulic Press.

Example 126

A Mild Syndet Bar Composition

A Brabender Prep-Mixer is charged with 1, 21, 39 and 30 which is heated to 80° C. with moderate stirring. Add 29, 33, 34, 36 and 37. Mix thoroughly. Add 3 and 8. Mix thoroughly. Add 17 and 13. Mix thoroughly. Add 31 and 38. Mix thoroughly, cool the mixture to room temperature and discharge when homogeneous. Place under a moderate vacuum and dry. Press into bars using a Carver Hydraulic Press.

Example 127

A Mild Antibacterial Deodorant Syndet Bar Composition

A Brabender Prep-Mixer is charged with 1, 22, 39 and 30 which is heated to 80° C. with moderate stirring. Add 33, 34, 35 and 37. Mix thoroughly. Add 17, 16 and 15. Mix thoroughly. Add 12, 31, 32 and 38. Mix thoroughly, cool the mixture to room temperature and discharge when homogeneous. Place under a moderate vacuum and dry. Press into bars using a Carver Hydraulic Press.

Example 128

A Mild Deodorant Toilet Bar Composition

A Brabender Prep-Mixer is charged with 5, 6, 39 and 22 which is heated to 80° C. with moderate stirring. Add 30, 33, 34, 36 and 37. Mix thoroughly. Add 23, 15, 14, 19, 20 and 12. Mix thoroughly. Add 31 and 38. Mix thoroughly, cool the mixture to room temperature and discharge when homogeneous. Place under a moderate vacuum and dry. Press into bars using a Carver Hydraulic Press.

Example 129

A Mild Antibacterial Deodorant Syndet Bar Composition

A Brabender Prep-Mixer is charged with 1, 5, 39, 21 and 22 which is heated to 80° C. with moderate stirring. Add 29, 32, 33, 34, 35 and 37. Mix thoroughly. Add 17 and 15. Mix thoroughly. Add 31, 32 and 38. Mix thoroughly, cool the mixture to room temperature and discharge when homogeneous. Place under a moderate vacuum and dry. Press into bars using a Carver Hydraulic Press.

Example 130

A Mild Mosturizing Syndet Bar Composition

A Brabender Prep-Mixer is charged with 23, 24, 39 and 9 which is heated to 80° C. with moderate stirring. Add 7 slowly. Mix thoroughly. Add 33, 34, 35 and 37. Mix thoroughly. Add 4, 2, 17, 16 and 26. Mix thoroughly. Add 31 and 38. Mix thoroughly, cool the mixture to room temperature and discharge when homogeneous. Place under a moderate vacuum and dry. Press into bars using a Carver Hydraulic Press.

Example 131

A Mild Moisturizing Syndet Bar Composition with Vitamin E and Bath Oil

A Brabender Prep-Mixer is charged with 23, 24, 39 and 10 which is heated to 80° C. with moderate stirring. Add 7 slowly. Mix thoroughly. Add 33, 34, 36 and 37. Mix thoroughly. Add 27, 4, 14, 15, 18, 17, 16, 13 and 12. Mix thoroughly. Add 28, 31 and 38. Mix thoroughly, cool the mixture to room temperature and discharge when homogeneous. Place under a moderate vacuum and dry. Press into bars using a Carver Hydraulic Press.

Examples 132–138

Prototype Hand and Facial Cleansing Compositions Comprising Heteroatom Containing Alkyl Aldonamide Compounds

| Ingredient (By Weight) | 132 % | 133 % | 134 % | 135 % | 136 % | 137 % | 138 % |
|---|---|---|---|---|---|---|---|
| 1. Sodium Cocoyl Sarcosinate (30%) | 3.3 | — | — | — | 3.0 | 10.0 | — |
| 2. Sodium Myristoyl Glutamate (30%) | — | — | — | — | — | 10.0 | — |
| 3. Sodium Cocoyl Isethionate | 20.0 | — | — | — | — | — | — |
| 4. Diethanolamine Oleth-10 Phosphate | — | 0.4 | — | — | — | — | — |
| 5. Sodium Laureth-2 Sulfate (28%) | — | — | — | 30.0 | — | — | — |
| 6. C8–C18 Alkyl Polyglycoside (50%) | 2.0 | — | — | — | — | — | — |
| 7. Glycereth-7 | — | — | — | — | 2.5 | — | — |
| 8. Ceteareth-20 | — | 1.0 | — | — | — | — | — |
| 9. PEG-26 Glycerate | — | — | — | — | — | 10.0 | — |
| 10. PEG-40 Hydrogenated Castor Oil | — | — | — | — | — | 4.0 | — |
| 11. PEG-75 Lanolin | — | — | — | — | 4.5 | — | — |
| 12. PEG-100 Stearate | — | — | — | — | 0.9 | — | — |
| 13. Polysorbate 60 | — | — | 1.0 | — | — | — | — |
| 14. Polysorbate 80 | — | — | — | — | — | — | 1.0 |
| 15. Cocoamidopropyl Betaine (35%) | — | — | — | 8.0 | — | — | — |

Prototype Hand and Facial Cleansing Compositions Comprising Heteroatom Containing Alkyl Aldonamide Compounds

| Ingredient (By Weight) | Example 132 % | 133 % | 134 % | 135 % | 136 % | 137 % | 138 % |
| --- | --- | --- | --- | --- | --- | --- | --- |
| 16. C8/C10 Oxypropyl D-Gluconamide | 1.0 | — | 1.0 | — | — | — | — |
| 17. C12 Oxypropyl D-Gluconamide | — | — | — | — | — | 1.0 | — |
| 18. N-Gluconyl C12 Di(oxyethyl) Glycinate (50%) | 1.0 | — | 6.0 | — | 6.6 | — | 3.5 |
| 19. C8/C10 Oxypropyl D-Lactobionamide (50%) | — | 3.0 | — | — | — | — | — |
| 20. C12 Oxypropyl D-Lactobionamide (50%) | — | 2.5 | — | — | — | 3.0 | — |
| 21. C12 Oxypropyl D-Maltobionamide (50%) | 5.0 | — | — | 5.5 | — | 3.0 | — |
| 22. C12–C15 Oxypropylaminopropyl D-Gluconamide | — | — | — | — | 0.5 | — | — |
| 23. Cocoaminopropyl D-Gluconamide (50%) | — | — | 0.3 | 0.1 | — | — | — |
| 24. Oleylaminopropyl D-Lactobionamide | — | 0.2 | — | 0.1 | — | — | — |
| 25. Magnesium Aluminum Silicate | 1.0 | — | — | — | — | — | — |
| 26. Magnesium Aluminum Silicate (4%) | — | — | — | — | 15.0 | — | — |
| 27. Poloxamer 188 | 12.0 | — | — | — | — | — | — |
| 28. Carbomer 934 (2%) | — | 20.0 | — | — | — | — | — |
| 29. Lauric Acid | — | — | — | — | — | 2.0 | — |
| 30. Myristic Acid | — | — | — | — | — | 2.0 | — |
| 31. Stearic Acid | 4.4 | — | 1.0 | — | 3.0 | — | — |
| 32. Mineral Oil | 2.5 | 27.0 | — | — | — | — | — |
| 33. Lanolin Oil | — | 0.4 | 5.0 | — | 2.5 | — | — |
| 34. Sesame Oil | — | — | — | — | 12.0 | — | — |
| 35. Squalane | — | 2.0 | — | — | — | — | — |
| 36. Cetyl Alcohol | 0.3 | — | 2.5 | — | 1.6 | — | — |
| 37. Stearyl Alcohol | 0.3 | — | — | — | — | — | — |
| 38. Cetearyl Alcohol | — | 0.5 | — | — | — | — | — |
| 39. Lanolin Alcohol | 2.5 | — | — | — | — | — | — |
| 40. Benzyl Alcohol | — | 0.3 | — | — | — | — | — |
| 41. Xanthan Gum | — | — | — | — | 0.2 | — | — |
| 42. Dimethicone | — | — | — | — | 1.0 | — | — |
| 43. Sorbitan Stearate | — | 0.2 | — | — | 0.8 | — | — |
| 44. Glyceryl Stearate | — | 1.8 | 2.0 | — | 1.8 | 2.5 | — |
| 45. Caprylic/Capric Triglyceride | — | 1.0 | — | — | — | 5.0 | — |
| 46. Neopentylglycol Dicaprylate/Dicaprate | — | — | — | — | 3.5 | — | — |
| 47. Isopropyl Lanolate | — | — | — | — | 3.6 | — | — |
| 48. Pentaerythrityl Tetralaurate | — | — | 2.0 | — | — | — | — |
| 49. Acetylated Lanolin | 1.0 | — | — | — | — | — | — |
| 50. Polydecene | — | — | 3.0 | — | — | — | — |
| 51. Microcrystalline Wax | — | — | 1.0 | — | — | — | — |
| 52. Aloe Vera Gel | 1.3 | — | — | 2.2 | — | — | 16.0 |
| 53. Hydrolyzed Milk Protein | — | — | — | 2.0 | — | — | — |
| 54. TEA-Coco Hydrolyzed Animal Protein | — | — | — | — | — | — | 18.0 |
| 55. Tocopheryl Acetate (Vitamin E) | — | — | — | — | — | — | 0.3 |
| 56. Sodium Dehydroacetate | — | 0.2 | — | — | 0.3 | — | — |
| 57. Sodium Pyrrolidone Carboxylic Acid | — | — | — | — | — | 4.0 | — |
| 58. Disodium EDTA | — | 0.1 | — | — | — | — | — |
| 59. Tetrasodium EDTA | — | — | — | 0.1 | — | — | — |
| 60. Sorbitol | — | 3.0 | — | — | — | — | — |
| 61. Propylene Glycol | — | 3.0 | — | — | — | — | 2.0 |
| 62. Butylene Glycol | — | — | — | — | — | 15.0 | — |
| 63. Glycerin | — | — | 5.0 | — | — | — | — |
| 64. Witch Hazel Extract | — | — | — | — | — | — | 0.8 |
| 65. Borax | — | — | 0.2 | — | — | — | — |
| 66. Imidazolidinyl Urea | — | — | — | 0.3 | 0.3 | — | 0.3 |
| 67. Methyl Paraben | 0.2 | — | 0.2 | 0.2 | 0.3 | 0.3 | 0.2 |
| 68. Propyl Paraben | 0.1 | 0.1 | 0.1 | 0.1 | 0.1 | 0.1 | — |
| 69. Sodium Chloride (50%) Adjust Viscosity | q.s. | q.s. | q.s. | q.s. | — | q.s. | — |
| 70. Ammonium Chloride (30%) Adjust Viscosity | — | — | — | — | q.s. | — | — |
| 71. Lactic Acid (35%) pH to 5–7 | — | — | — | q.s. | q.s. | — | — |
| 72. Citric Acid (35%) pH to 5–7 | q.s. | q.s. | q.s. | — | — | q.s. | — |
| 73. Triethanolamine | — | 0.2 | — | — | — | — | — |
| 74. Dye (0.2%–1%) | q.s. | q.s. | q.s. | q.s. | q.s. | q.s. | — |
| 75. Fragrance | q.s. | q.s. | q.s. | q.s. | q.s. | q.s. | q.s. |
| 76. Water | 42.1 | 33.3 | 69.7 | 51.4 | 36.0 | 28.1 | 57.9 |

Example 132

A Foaming Hand and Facial Cleansing Cream Composition with Aloe

Container A is charged with 76 and 25 which is heated to 70° C. with moderate stirring. Add 67 and 68. Mix thoroughly. Container B is charged with 36, 37, 39, 49, 32, 31, 1, 27, 6 and 3 which is heated to 70° C. with moderate stirring. Slowly add A to B while stirring. Add 21, 18 and 16. Mix thoroughly. Add 52, 74, 75, 72 and 69. Mix thoroughly, cool the mixture to room temperature and discharge when homogeneous.

Example 133

A Foaming Hand and Facial Cleansing Cream Composition

Container A is charged with 32, 38, 8, 35, 44, 33, 45, 43, 68 and 4 which is heated to 78° C. with moderate stirring. Container B is charged with 76, 60, 61, 56, 58 and 28 which is heated to 75° C. with moderate stirring. Add 19, 20 and 24. Slowly add A to B while stirring. Cool to 48 C. Add 73, 40, 75, 74, 72 and 69. Mix thoroughly, cool the mixture to room temperature and discharge when homogeneous.

Example 134

A Foaming Hand and Facial Cleansing Cream Composition

Container A is charged with 33, 50, 48, 44, 36, 51, 31 and 68 which is heated to 75° C. with moderate stirring. Container B is charged with 63, 13, 65 and 67 which is heated to 75° C. with moderate stirring. Container C is charged with 76, 74, 16, 18 and 23 which is heated to 75° C. with moderate stirring. Slowly add A to B while stirring. Mix thoroughly. Slowly add C to AB while stirring. Mix thoroughly. Cool to 48° C. Add 75, 72 and 69. Mix thoroughly, cool the mixture to room temperature and discharge when homogeneous.

Example 135

A Foaming Hand and Facial Cleansing Composition with Protein and Aloe

Container A is charged with 76, 23, 24 and 21 which is heated to 55° C. with moderate stirring. Add 5, 67, 68 and 59. Mix thoroughly. Add 66, 15, 52, 53, 74, 75, 71 and 69. Mix thoroughly, cool the mixture to room temperature and discharge when homogeneous.

Example 136

A Foaming Hand and Facial Cleansing Cream Composition

Container A is charged with 26, 76 and 41 which is heated to 70° C. with moderate stirring. Add 1, 7, 11, 12, 18 and 22. Mix thoroughly. Add 56, 67, 68 and 66. Mix thoroughly. Container B is charged with 33, 34, 36 and 43 which is heated to 70° C. with moderate stirring. Add 44, 46, 47 42 and 31. Mix thoroughly. Slowly add B to A while stirring. Add 74, 75 71 and 70. Mix thoroughly, cool the mixture to room temperature and discharge when homogeneous.

Example 137

A Foaming Hand and Facial Cleansing Cream Composition

Container A is charged with 29, 30, 44, 45, 10 and 68 which is heated to 75° C. with moderate stirring. Container B is charged with 76, 62, 9, 57, 1, 2 and 67 which is heated to 75° C. with moderate stirring. Add 17, 20 and 21. Mix thoroughly. Slowly add A to B while stirring. Add 74, 75, 72 and 69. Mix thoroughly, cool the mixture to room temperature and discharge when homogeneous.

Example 138

An Astringent Facial Cleansing Composition with Protein, Vitamin E and Aloe Container A is charged with 76, 18 61 and 14 which is heated to 40° C. with moderate stirring. Add 67 and 64. Mix thoroughly. Add 52 and 54. Mix thoroughly. Add 66, 65 and 75. Mix thoroughly, cool the mixture to room temperature and discharge when homogeneous.

Examples 139–145

Prototype Cream and Lotion Compositions Comprising Heteroatom Containing Alkyl Aldonamide Compounds

| Ingredients (By Weight) | 139 % | 140 % | 141 % | 142 % | 143 % | 144 % | 145 % |
|---|---|---|---|---|---|---|---|
| 1. PPG-10 Butanediol | 2.0 | 2.0 | — | — | — | — | — |
| 2. PPG-20 Methyl Glucose Ether | — | — | — | 4.0 | — | — | — |
| 3. PPG-15 Stearyl Ether | — | — | 0.4 | — | — | — | — |
| 4. Ceteareth-20 | — | 0.6 | 0.5 | — | — | 4.0 | — |
| 5. PPG-8 $C_{12}$–$C_{20}$ | — | — | — | 5.0 | — | — | — |
| Alkyl Ester | | | | | | | |
| 6. PEG-20 Methyl Glucose Sesquistearate | — | — | — | 1.2 | — | — | — |
| 7. PEG-40 Hydrogenated Castor Oil | — | — | — | 2.0 | — | — | — |
| 8. PEG-100 Stearate | — | — | — | 0.2 | 0.7 | — | — |
| 9. PEG-75 (Carbowax 3350) | — | — | — | — | — | 3.6 | — |
| 10. Myristamidopropyldimethylamine Phosphate | — | — | — | — | — | — | 0.5 |
| 10b. Polysorbate-65 | — | — | — | — | — | — | 2.0 |
| 11. C8/C10 Oxypropyl D-Gluconamide | 0.5 | — | 1.0 | — | 0.5 | 0.5 | — |
| 12. Isotridecyloxypropyl D-Gluconamide (50%) | — | 6.0 | 1.0 | — | 10.0 | — | — |
| 13. Gluconyl C12 DL-Alaninate/Ester of Ethanolamine | — | — | 0.5 | — | — | 0.5 | — |
| 14. Isodecyloxypropyl Glucoheptonamide | 3.3 | — | — | 6.0 | — | — | 6.0 |
| 15. C8/C10 Oxypropyl D-Lactobionamide (50%) | 2.0 | 2.0 | 3.0 | — | — | 2.0 | — |
| 16. C12 Oxypropyl D-Maltobionamide (50%) | — | — | — | 1.5 | — | 5.0 | — |
| 17. C12–C15 Oxypropylaminopropyl D-Gluconamide | — | — | 0.2 | — | 0.1 | — | — |
| 18. C12–C15 Oxypropylpropionamidopropyl D-Gluc | 1.0 | 1.0 | — | — | — | — | — |
| 19. C12–C15 Oxypropyl Gluc 5(oxyethylene) Ether | 1.0 | 1.0 | 2.0 | 1.0 | — | 3.0 | — |
| 19b. Tallowaminopropyl D-Lactobionamide | — | — | — | 0.5 | — | — | — |
| 20. Cetyl Alcohol | — | — | 0.3 | 3.5 | 2.0 | — | 2.5 |
| 21. Myristyl Alcohol | — | — | — | — | — | — | 0.5 |
| 22. Stearyl Alcohol | 2.5 | 1.4 | — | — | — | — | — |
| 23. Cetearyl Alcohol | — | — | 1.7 | — | — | — | — |
| 24. Cetyl Octanoate | 3.0 | 4.0 | — | 10.0 | — | — | — |
| 25. Glyceryl Stearate | 1.5 | — | 1.0 | — | 3.3 | 1.0 | 5.0 |
| 26. Sobitan Stearate | — | — | 0.5 | — | — | — | — |
| 27. Propylene Glycol Dipelargonate | — | 4.0 | — | — | — | — | — |
| 28. Ethylene Glycol Monostearate | — | — | — | — | — | 1.0 | — |
| 29. Decaglyceryl Diisostearate | — | 1.5 | — | — | — | — | — |
| 30. Acetylated Lanolin Alcohol | — | — | 0.2 | — | — | — | — |
| 31. $C_{12}$–$C_{15}$ Alcohol Benzoate | — | — | 0.4 | — | 4.0 | — | — |
| 32. Octyl Palmitate | — | — | — | — | — | 2.5 | — |
| 33. Methyl Glucose Sesquistearate | — | — | 0.8 | — | — | — | — |
| 34. Diisoarachidyl Dilinoleate | — | — | 1.0 | — | — | — | — |
| 35. Dioctyl Maleate | — | — | — | 5.0 | — | — | — |
| 36. Ascorbyl Palmitate | — | — | — | 0.1 | — | — | — |
| 37. Stearic Acid (xxx) | — | — | 0.5 | — | 1.0 | 1.0 | — |
| 38. Isostearic Acid | — | — | — | — | — | 1.7 | — |
| 39. Tocopheryl Acetate (Vitamin E) | — | — | — | 0.2 | — | 0.1 | 1.0 |
| 40. Panthenol (Provitamin B5) | — | — | — | — | — | — | 1.0 |
| 41. Retinyl Palmitate Polypeptide | — | — | 3.0 | — | — | — | — |

-continued

Prototype Cream and Lotion Compositions Comprising Heteroatom Containing Alkyl Aldonamide Compounds

| Ingredients (By Weight) | Example 139 % | 140 % | 141 % | 142 % | 143 % | 144 % | 145 % |
|---|---|---|---|---|---|---|---|
| 42. Lecithin | — | — | 10.0 | — | — | — | — |
| 43. Proline | — | — | — | — | 1.0 | — | — |
| 44. Polyglucan | — | — | 0.1 | — | — | — | — |
| 45. Jojoba Oil | — | — | — | 2.0 | — | — | — |
| 46. Avocado Oil | — | — | — | 2.0 | — | — | — |
| 47. Mineral Oil | — | — | — | — | — | 7.0 | 10.0 |
| 48. Polydecene | 4.0 | 10.0 | — | — | — | — | — |
| 49. Emulsifying Wax | — | — | — | — | — | 5.0 | — |
| 50. White Beeswax | — | — | — | — | — | 1.5 | 0.5 |
| 51. Thistle Extract | — | — | — | 1.0 | — | — | — |
| 52. Lemon Extract | — | — | — | — | 2.5 | — | — |
| 53. Passion Fruit Extract | — | — | — | — | 2.5 | — | — |
| 54. Lactic Acid (88%) | — | — | — | — | — | 2.5 | 2.0 |
| 55. Glycosphingolipids | — | — | — | — | — | — | 0.1 |
| 56. Phospholipids | — | — | — | — | — | — | 0.2 |
| 57. Stearamidopropyl PG-Dimonium Phosphate | 3.0 | — | — | — | — | — | — |
| 58. Cholesterol | — | — | — | — | — | — | 0.3 |
| 59. PEG-25 Soya Sterol | — | — | — | — | — | — | — |
| 60. Polyquaternium-24 | 0.3 | — | — | — | — | — | — |
| 61. Dimethicone | 1.0 | — | 0.2 | 0.5 | 0.2 | 2.0 | — |
| 62. Simethicone | 0.1 | — | — | — | — | — | — |
| 63. Xanthan Gum | — | — | — | — | 0.3 | 0.3 | — |
| 64. Magnesium Aluminium Silicate | — | — | 0.3 | — | 1.0 | — | — |
| 65. Carbopol 934 (2%) | — | 31.0 | — | — | — | — | — |
| 66. Carbopol 941 (2%) | — | — | 7.5 | — | — | — | — |
| 67. Disodium EDTA | — | 0.1 | — | 0.1 | — | — | — |
| 68. Tetrasodium EDTA | — | — | 0.1 | — | — | — | — |
| 69. Sodium Lactate | — | — | — | — | 2.0 | — | — |
| 70. Sodium Pyrrolidone Carboxylic Acid | — | — | — | — | 1.0 | — | — |
| 71. Borax | — | 1.4 | — | — | — | — | — |
| 72. Titanium Dioxide | 0.1 | — | — | — | — | — | — |
| 73. Benzyl Alcohol | — | 0.2 | — | — | — | — | — |
| 74. Urea | — | — | — | — | — | 3.5 | — |
| 75. Propylene Glycol | — | — | 0.5 | — | 3.0 | 1.5 | 1.0 |
| 76. Glycerin | 15.0 | 2.0 | 3.0 | — | 2.0 | — | — |
| 77. Diglycerin | — | 2.0 | — | — | — | — | — |
| 78. Sorbitol | — | — | — | — | 1.0 | — | — |
| 79. Diazolidinyl Urea | — | — | 0.1 | — | 0.3 | — | 0.1 |
| 80. Imidazolidinyl Urea | — | — | 13 | 0.3 | — | — | — |
| 81. Methylchloroisothiazoline | — | — | — | 0.05 | — | — | — |
| 82. Methylisothiazoline | — | — | — | 0.05 | — | — | — |
| 83. DMDM Hydantoin | 0.1 | — | — | — | — | — | — |
| 84. Methyl Paraben | 0.2 | 0.2 | 0.2 | — | 0.3 | 0.2 | — |
| 85. Propyl Paraben | 0.1 | 0.1 | 0.1 | — | 0.1 | — | 0.1 |
| 86. Isopropyl Paraben | — | — | — | — | — | 0.2 | — |
| 87. Isobutyl Paraben | — | — | — | — | — | 0.1 | — |
| 88. Butyl Paraben | — | — | — | — | — | 0.1 | — |
| 89. Fragrance | 0.2 | 0.2 | 0.1 | 0.5 | 0.2 | 0.2 | 0.2 |
| 90. Sodium Hydroxide (10%) | — | — | — | — | — | 0.5 | — |
| 91. Potassium Hydroxide (25%) | — | — | 0.5 | — | — | — | — |
| 92. Sodium Citrate (35%) | — | — | — | — | — | — | 0.6 |
| 93. Triethanolamine | — | — | — | — | 0.4 | — | — |
| 94. Citric Acid (35%) pH to 5–8 | — | — | — | — | — | 0.9 | — |
| 95. Water | 59.1 | 29.4 | 60.2 | 57.5 | 55.7 | 48.5 | 63.7 |

Example 139

A Moisturizing Lotion Composition

Container A is charged with 48, 24, 1, 22, 19, 25, 61, 62 and 85 which is heated to 82° C. with moderate stirring. Mix thoroughly. Container B is charged with 95, 84, 11, 18, 83, 76, 77 and 72 which is heated to 73° C. with moderate stirring. Add 60 and 57. Mix thoroughly. Add 14 and 15. Mix thoroughly. Slowly add B to A while stirring. Add 89. Mix thoroughly, cool the mixture to room temperature and discharge when homogeneous.

Example 140

A Moisturizing Lotion Composition

Container A is charged with 48, 27, 24, 1, 22, 4, 29 and 85 which is heated to 82° C. with moderate stirring. Mix thoroughly. Container B is charged with 95, 84, 67, 76, 77 and 71 which is heated to 73° C. with moderate stirring. Add 65, 12, 15, 18 and 19. Mix thoroughly. Slowly add B to A while stirring. Add 73 and 89. Mix thoroughly, cool the mixture to room temperature and discharge when homogeneous.

Example 141

A Moisturizing Cream Composition

Container A is charged with 95 and 64 which is heated to 70° C. with moderate stirring. Mix thoroughly. Add 66, 68, 75, 79, 84, 85 and 76. Mix thoroughly. Add 11, 12, 13, 15, 17 and 19. Container B is charged with 23, 4, 26, 37, 25, 20, 30, 31, 3, 61 and 34 which is heated to 75° C. with moderate stirring. Slowly add A to B while stirring. Mix thoroughly. Add 91 and cool to 55° C. Add 41, 42, 44 and 89. Mix thoroughly, cool the mixture to room temperature and discharge when homogeneous.

Example 142

A Moisturizing Lotion Composition with Antioxidants for Aging Skin

Container A is charged with 5, 6, 33, 20, 24, 45, 46, 61, 39 and 36 which is heated to 70° C. with moderate stirring. Mix thoroughly. Container B is charged with 95, 8, 80, 81, 82, 67, 14, 16, 19 and 19b which is heated to 70° C. with moderate stirring. Add 7, 51 and 2. Mix thoroughly. Slowly add B to A while stirring. Add 89. Mix thoroughly, cool the mixture to room temperature and discharge when homogeneous.

Example 143

A Moisturizing Cream Composition with Alpha Hydroxy Acids

Container A is charged with 95, 64 and 65 which is heated to 75° C. with moderate stirring. Mix thoroughly. Add 67, 84, 75, 76, 69 70, 78 and 43. Mix thoroughly. Add 11, 12 and 17. Mix thoroughly. Container B is charged with 37, 8, 25, 35, 31, 61, 20 and 85 which is heated to 75° C. with moderate stirring. Add 93, 79, 52, 53 and 89. Mix thoroughly. Slowly add B to A while stirring. Add 89. Mix thoroughly, cool the mixture to room temperature and discharge when homogeneous.

Example 144

A Moisturizing Cream Composition with Alpha Hydroxy Acids and Vitamin E

Container A is charged with 95, 75 and 63 which is heated to 73° C. with moderate stirring. Mix thoroughly. Add 74, 94, 9, 84 and 90. Mix thoroughly. Add 11, 13, 15, 16 and 19. Mix thoroughly. Container B is charged with 4, 49, 47, 32, 50, 38, 61, 28, 25, 37, 86, 87, 88, and 39 which is heated to 80° C. with moderate stirring. Slowly add B to A while stirring. Add 54 and 89. Mix thoroughly, cool the mixture to room temperature and discharge when homogeneous.

Example 145

A Moisturizing Cream Composition with Alpha Hydroxy Acids and Vitamins

Container A is charged with 95, 10, 75, 54, 40 and 92 which is heated to 75° C. with moderate stirring. Mix thoroughly. Add 14. Mix thoroughly. Container B is charged with 47, 25, 20, 10b, 39, 50, 59 and 21 which is heated to 75° C. with moderate stirring. Mix thoroughly. Add 55, 56 and 58. Slowly add B to A while stirring. Add 79, 84, 85 and 89. Mix thoroughly, cool the mixture to room temperature and discharge when homogeneous.

Examples 146–152

Prototype Sunscreen Compositions Comprising Heteroatom Containing Alkyl Aldonamide Compounds

| Ingredients (By Weight) | Example 146 % | 147 % | 148 % | 149 % | 150 % | 151 % | 152 % |
|---|---|---|---|---|---|---|---|
| 1. PEG-100 Stearate | — | — | — | 1.0 | — | — | — |
| 2. PEG-25 Stearate | — | — | 3.5 | 1.0 | — | — | — |
| 3. DEA Cetyl Phosphate | — | — | — | — | 3.5 | 2.0 | — |
| 4. Castor Oil | 48.9 | — | — | — | — | — | — |
| 5. Hydrogenated Castor Oil | 0.5 | — | — | — | — | — | — |
| 6. Hydrogenated Sunflower Seed Oil | 2.0 | — | — | — | — | — | — |
| 7. Hydrogenated Peanut Oil | — | — | — | — | 2.0 | — | — |
| 8. Hybrid Sunflower Seed Oil | 2.0 | — | — | — | — | — | — |
| 9. Mineral Oil | — | — | 2.8 | 12.5 | — | — | — |
| 10. Cetyl Alcohol | — | 5.0 | — | 0.5 | 2.0 | 2.0 | 2.0 |
| 11. Isostearyl Alcohol | — | 41.2 | — | — | — | — | — |
| 12. Lanolin Alcohol | — | — | 1.1. | — | — | — | — |
| 13. Isopropyl Myristate | — | — | 7.0 | — | 5.0 | — | — |
| 14. Cetyl Octanoate | — | — | 8.0 | 3.0 | — | — | — |
| 15. Coconut Caprate/Caprylate | — | — | — | 3.0 | — | 6.0 | — |
| 16. Hydroxyoctacosanyl Hydroxystearate | — | — | 6.0 | — | — | — | — |
| 17. C$_{12}$-C$_{15}$ Alcohol Benzoate | — | — | 10.0 | — | — | — | — |
| 18. Glyceryl Stearate | — | — | — | 3.0 | — | — | 3.0 |
| 19. Glyceryl Myristate | — | — | — | — | 5.0 | — | — |
| 20. 2-Hexanolethyl Salicylate | — | — | — | — | — | — | 5.0 |
| 21. Jojoba Esters | 17.9 | — | — | — | — | — | — |
| 22. Paraffin Wax | — | — | — | — | — | — | 5.0 |
| 23. Castor Wax | — | — | — | 0.5 | — | — | — |
| 24. Carnauba Wax | 5.0 | 5.0 | — | — | — | — | — |
| 25. Candelilla Wax | 5.0 | 17.8 | — | — | — | — | — |
| 26. Beeswax | 3.0 | — | 10.0 | — | — | — | — |
| 27. Squalane | — | — | — | — | — | 10.0 | — |
| 28. C8/C10 Oxypropyl D-Gluconamide | — | 0.5 | 0.5 | — | 0.5 | 0.5 | — |
| 29. C12 Oxypropyl D-Gluconamide | — | 3.0 | — | — | — | — | 0.3 |
| 30. N-Gluconyl C12 Di(oxyethyl) Glycinate (50%) | 1.0 | — | — | — | 3.0 | — | 8.0 |
| 31. C8/C10 Oxypropyl D-Lactobionamide (50%) | — | — | 2.9 | 3.0 | — | — | — |
| 32. C12 Oxypropyl D-Lactobionamide (50%) | 2.0 | — | — | 1.1 | — | — | — |
| 33. C12 Oxypropyl D-Maltobionamide (50%) | 2.7 | — | — | 2.0 | — | 8.0 | — |
| 34. C12–C15 Oxypropylaminopropyl D-Gluconamide | — | — | 0.1 | 0.1 | — | — | — |
| 35. Cocoaminopropyl D-Gluconamide (50%) | — | — | 0.1 | — | — | — | — |
| 36. Oleylaminopropyl D-Lactobionamide | — | — | — | — | 0.2 | — | — |
| 37. Stearic Acid (xxx) | — | 15.0 | — | 2.0 | — | 4.0 | 5.0 |
| 38. Acrylates/Octylpropenamide Copolymer | — | 2.0 | — | — | — | — | — |
| 39. Cetyl Ricinoleate | 2.0 | — | — | — | — | — | — |
| 40. Octyl Methoxycinnamate | 5.0 | 7.5 | 7.5 | 7.5 | 2.0 | 7.5 | — |
| 41. Butyl Methoxydibenzoylmethane | — | — | — | — | 1.0 | — | — |
| 42. Methyl Anthranilate | — | — | 5.0 | — | — | — | — |
| 43. Benzophenone-3 | — | 3.0 | — | — | — | — | — |
| 44. Benzophenone-4 | — | — | — | — | — | 4.0 | — |
| 46. Carbomer 934 (2%) | — | — | — | 15.0 | — | — | — |
| 46. Carbomer 940 (2%) | — | — | — | — | — | 10.0 | 5.0 |
| 47. Tocopheryl Acetate (Vitamin E) | — | — | — | 0.1 | 0.2 | — | 0.2 |
| 48. Ascorbic Acid (Vitamin C) | — | — | — | — | 0.3 | — | — |
| 49. Ascorbyl Palmitate | — | — | — | — | — | — | 0.2 |
| 50. Retinyl Palmitate (Vitamin A) | — | — | — | — | — | — | 0.3 |
| 51. Bioflavoniod | — | — | — | — | — | — | 0.4 |
| 52. Ivy Extract | — | — | — | — | — | — | 0.9 |
| 53. Dimethicone | — | — | — | — | — | 0.5 | 5.0 |
| 54. Titanium Dioxide | 0.8 | — | — | — | — | — | 0.4 |
| 55. Iron Oxide | — | — | — | — | — | — | 0.1 |
| 56. β-Carotene (1%, Provitamin A) | 0.1 | — | — | — | 0.2 | — | — |
| 57. Sodium Borate | — | — | 0.7 | — | — | — | — |
| 58. Tetrasodium EDTA | — | — | — | 0.1 | — | — | — |
| 59. Disodium EDTA | — | — | — | — | 0.1 | 0.1 | — |
| 60. Glycerin | — | — | — | — | — | — | 5.0 |
| 61. Sorbitol (70%) | — | — | — | 3.0 | 5.0 | — | — |
| 62. Propylene Glycol | — | — | 0.5 | 0.5 | 0.5 | 5.0 | — |
| 63. Butylated Hydroxytoluene | — | — | — | — | 0.1 | 0.1 | — |
| 64. Imidazolidinyl Urea | — | — | — | — | — | — | 0.1 |
| 65. Diazolidinyl Urea | — | — | 0.1 | 0.1 | 0.1 | 0.1 | — |
| 66. Methyl Paraben | — | — | 0.2 | 0.2 | 0.2 | 0.2 | 0.2 |
| 67. Propyl Paraben | 0.1 | — | 0.1 | 0.1 | 0.1 | 0.1 | 0.1 |
| 68. Triethanolamine | — | — | — | 0.6 | — | 2.4 | 0.8 |
| 69. Fragrance | 2.0 | — | 0.2 | 0.2 | 0.2 | 0.2 | 0.2 |
| 70. Water | — | — | 33.7 | 52.8 | 68.8 | 47.3 | 42.8 |

Example 146

A Sunscreen Lip Protectant Composition

Container A is charged with 4, 21, 24, 25, 26, 5, 39, 6 and 67 which is heated to 82° C. with moderate stirring. Container B is charged with 8 and 54 which is heated to 73° C. with moderate stirring. Slowly add B to A while stirring. Add 56, 40, 30 32, 33 and 69. Mix thoroughly, cool the mixture to room temperature and discharge when homogeneous.

Example 147

A Sunscreen Lip Protectant Composition

Container A is charged with 11, 43, 40, 37 and 10 which is heated to 80° C. with moderate stirring. Slowly add 38. Container B is charged with 24 and 25 which is heated to 80° C. with moderate stirring. Slowly add B to A while stirring. Add 28 and 29. Mix thoroughly, cool the mixture to room temperature and discharge when homogeneous.

Example 148

A Sunscreen Lotion Composition

Container A is charged with 13, 14, 9, 12, 17, 40, 42, 16, 2 and 26 which is heated to 75° C. with moderate stirring. Container B is charged with 70, 57, 28, 31, 34 and 35 which is heated to 75° C. with moderate stirring. Mix thoroughly. Slowly add A to B while stirring. Add 62, 65, 66, 67 and 69. Mix thoroughly, cool the mixture to room temperature and discharge when homogeneous.

Example 149

A Sunscreen Cream Composition with Vitamin E

Container A is charged with 70, 45, 61, 31, 32, 33, 34 and 58 which is heated to 75° C. with moderate stirring. Container B is charged with 47, 1, 18, 2, 37, 14, 15, 9, 23, 40 and 10 which is heated to 75° C. with moderate stirring. Mix thoroughly. Slowly add A to B while stirring. Add 68, 62, 65, 66, 67 and 69. Mix thoroughly, cool the mixture to room temperature and discharge when homogeneous.

Example 150

A Sunscreen Cream Composition with Vitamin E

Container A is charged with 40, 41, 13, 19, 10, 7 and 63 which is heated to 75° C. with moderate stirring. Add 3. Mix thoroughly. Container B is charged with 70, 59, 28, 30 and 36 which is heated to 75° C. with moderate stirring. Mix thoroughly. Slowly add A to B while stirring. Add 47, 56, 48, 61, 62, 65, 66, 67 and 69. Mix thoroughly, cool the mixture to room temperature and discharge when homogeneous.

Example 151

A Sunscreen Lotion Composition

Container A is charged with 40, 15, 37, 10 and 53 which is heated to 85° C. with moderate stirring. Add 3. Mix thoroughly. Container B is charged with 70, 62, 46, 59, 44, 28 and 33 which is heated to 85° C. with moderate stirring. Mix thoroughly. Slowly add A to B while stirring. Add 68, 63, 64, 65, 67 and 69. Mix thoroughly, cool the mixture to room temperature and discharge when homogeneous.

Example 152

A Sunscreen Lotion Composition with Vitamins

Container A is charged with 37, 10, 18, 22, 27, 20, 53, 55 and 54 which is heated to 75° C. with moderate stirring. Mix thoroughly. Container B is charged with 70, 46, 66, 67, 64, 68, 60, 30 and 29 which is heated to 75° C. with moderate stirring. Mix thoroughly. Slowly add B to A while stirring. Add 47, 49, 50, 51, 52 and 69. Mix thoroughly, cool the mixture to room temperature and discharge when homogeneous.

Examples 153–157

Prototype Shaving Cream Compositions Comprising Heteroatom Containing Alkyl Aldonamide Compounds

| Ingredients (By Weight) | 153 % | 154 % | 155 % | 156 % | 157 % | % | % |
|---|---|---|---|---|---|---|---|
| 1. Triethanolamine Lauryl Sulfate (40%) | — | — | — | 25.0 | — | — | — |
| 2. Sodium Laureth-2 Sulfate (26%) | 20.0 | — | — | — | — | — | — |
| 3. Ammonium Laureth-2 Sulfate (26%) | 15.0 | — | — | — | — | — | — |
| 4. Sodium Coconut Sarcosinate (30%) | — | — | 15.0 | — | — | — | — |
| 5. Coconut Sarcosine | — | — | 2.5 | — | — | — | — |
| 6. Disodium Laurethsulfosuccinate (40%) | — | — | — | 12.5 | — | — | — |
| 7. Sodium Cocoyl Isethionate | — | — | — | — | 3.0 | — | — |
| 8. Polysorbate-80 | — | 0.5 | — | — | — | — | — |
| 9. Polysorbate-20 | — | — | — | 2.0 | — | — | — |
| 10. PEG-75 Lanolin | — | — | — | — | 0.5 | — | — |
| 11. C8/C10 Oxypropyl D-Gluconamide | — | 0.5 | 1.0 | — | 0.5 | — | — |
| 12. C12 Oxypropyl D-Gluconamide | 1.0 | — | — | — | 0.2 | — | — |
| 13. N-Gluconyl C12 Di(oxyethyl) Glycinate (50%) | 2.0 | — | — | — | — | — | — |
| 14. C8/C10 Oxypropyl D-Lactobionamide (50%) | — | 2.5 | — | — | 4.3 | — | — |
| 15. C12 Oxypropyl D-Lactobionamide (50%) | 8.0 | — | — | — | — | — | — |
| 16. C12 Oxypropyl D-Maltobionamide (50%) | — | — | 5.0 | 6.0 | — | — | — |
| 17. C12–C15 Oxypropylaminopropyl D-Gluconamide | — | 0.3 | — | — | — | — | — |
| 18. Cocoaminopropyl D-Gluconamide (50%) | — | — | 0.1 | — | — | — | — |
| 19. Oleylaminopropyl D-Lactobionamide | — | — | 0.1 | — | 0.1 | — | — |
| 20. Isopropyl Lanolate | — | 0.8 | — | — | — | — | — |
| 21. Ethylene Glycol Stearate | 1.0 | — | — | — | — | — | — |
| 22. Propylene Glycol Stearate | — | — | 2.5 | — | — | — | — |
| 23. Cetyl Acetate | — | 0.2 | — | — | — | — | — |
| 24. Cetyl Alcohol | — | — | 1.5 | — | — | — | — |
| 25. Acetylated Lanolin Alcohol | — | 0.3 | — | — | — | — | — |
| 26. Coconut Acid | — | 2.0 | — | — | — | — | — |
| 27. Stearic Acid (xxx) | — | 5.5 | 7.0 | — | 7.0 | — | — |
| 28. Lanolin Acid | — | 0.8 | — | — | — | — | — |
| 29. Potassium Cocoate | — | — | 35.0 | — | — | — | — |
| 30. Glycosphingolipids | 3.0 | — | — | — | — | — | — |
| 31. Hydroxyethyl Cellulose | — | 0.1 | — | — | — | — | — |
| 32. Polyvinylpyrrolidone | — | — | 0.7 | — | — | — | — |
| 33. Talc | — | — | 5.0 | — | — | — | — |
| 34. Propyltrimonium Hydrolyzed Collagen | 5.0 | — | — | — | — | — | — |
| 35. TEA Coco Hydrolyzed Animal Protein | — | — | — | — | 10.0 | — | — |
| 36. Polyquaternium-10 | — | — | — | 2.0 | — | — | — |
| 37. Polyquaternium-24 | — | 0.3 | — | — | — | — | — |
| 38. Aloe Vera Gel | — | — | — | — | 0.5 | — | — |
| 39. Allantoin | — | — | — | — | 0.2 | — | — |

-continued

Prototype Shaving Cream Compositions Comprising Heteroatom Containing Alkyl Aldonamide Compounds

| Ingredients (By Weight) | Example 153 % | 154 % | 155 % | 156 % | 157 % | — % | — % |
|---|---|---|---|---|---|---|---|
| 40. Sorbitol (70%) | — | — | 5.0 | — | 1.3 | — | — |
| 41. Glycerin | — | 4.0 | — | — | — | — | — |
| 42. Propylene Glycol | 3.0 | — | — | 0.5 | — | — | — |
| 43. Diazolidinyl Urea | 0.3 | — | — | 0.2 | — | — | — |
| 44. Methyl Paraben | 0.2 | 0.2 | 0.2 | 0.2 | 0.2 | — | — |
| 45. Propyl Paraben | — | 0.1 | 0.1 | 0.1 | 0.1 | — | — |
| 46. Triethanolamine | — | 2.9 | — | — | 5.0 | — | — |
| 47. Fragance | 0.1 | 0.1 | 0.2 | 0.2 | 0.2 | — | — |
| 48. Water | 41.4 | 72.4 | 19.1 | 51.3 | 66.9 | — | — |
| 49. Propellant (Butane/Propane) | — | 8.0 | — | — | 15.0 | — | — |

Example 153

A Foaming Shaving Lotion Composition

Container A is charged with 48, 42 and 44 which is heated to 80° C. with moderate stirring. Container B is charged with 2, 3, 21, 15, 13 and 12 which is heated to 65° C. with moderate stirring. Add 34 and 30. Mix thoroughly. Add 43 and 47. Mix thoroughly. Slowly add B to A while stirring. Mix thoroughly, cool the mixture to room temperature and discharge when homogeneous.

Example 154

A Foaming Conditioning Aerosol Shaving Cream Composition

Container A is charged with 48, 37 and 31 which is heated to 85° C. with moderate stirring. Add 41, 46, 44 and 45. Container B is charged with 20, 28, 8, 23, 25, 26, 27, 11, 14 and 17 which is heated to 85° C. with moderate stirring. Mix thoroughly. Slowly add B to A while stirring. Add 47. Mix thoroughly, cool the mixture to room temperature and discharge when homogeneous into cans and fill with propellant. (Product:propellant concentration=92%:8%).

Example 155

A Foaming Brushless Shaving Cream Composition

Container A is charged with 48, 4, 5, 40, 29, 32, 16 and 11 which is heated to 65° C. with moderate stirring. Mix thoroughly. Add 33. Container B is charged with 27, 24 and 22 which is heated to 65° C. with moderate stirring. Mix thoroughly. Slowly add B to A while stirring. Add 18, 19, 44, 45 and 47. Mix thoroughly, cool the mixture to room temperature and discharge when homogeneous.

Example 156

A Foaming Shaving Gel Composition

Container A is charged with 48 and 36 which is heated to 65° C. with moderate stirring. Mix thoroughly. Add 1, 6, 9, 16, 42, 43, 44, 45 and 47 Mix thoroughly, cool the mixture to room temperature and discharge when homogeneous.

Example 157

A Foaming Conditioning Aerosol Shaving Cream Composition

Container A is charged with 48 and 46 which is heated to 85° C. with moderate stirring. Mix thoroughly. Add 40, 44 and 45. Mix thoroughly. Add 27, 7, 10, 14, 19, 11 and 12. Mix thoroughly. Add 38, 39, 47 and 35 Mix thoroughly, cool the mixture to room temperature and discharge when homogeneous into cans and fill with propellant. (Product:propellant concentration=85%:15%).

Examples 158–164

Prototype Anti-Perspirant Compositions Comprising Heteroatom Containing Alkyl Aldonamide Compounds

| Example Ingredients (By Weight) | 158 % | 159 % | 160 % | 161 % | 162 % | 163 % | 164 % |
|---|---|---|---|---|---|---|---|
| 1. PPG-3 Myristyl Ether | 5.0 | 5.0 | — | — | — | — | — |
| 2. PEG-8 Distearate | 2.0 | — | — | — | — | — | — |
| 3. PPG-14 Butyl Ether | — | — | 2.0 | — | — | — | — |
| 4. PPG-15 Stearyl Ether | — | — | — | — | — | 1.0 | — |
| 5. PEG-100 Stearate | — | 0.6 | — | — | 0.6 | — | — |
| 6. Oleth-10 | — | — | — | — | — | 1.0 | — |
| 7. Ethylhexyl-oxypropyl D-Gluconamide | 1.0 | — | — | — | 1.0 | — | — |
| 8. Isotridecyl-oxypropyl D-Gluconamide | — | 0.3 | — | — | 1.0 | — | — |
| 9. Gluconyl C12 DL-Alaninate | — | 0.1 | — | — | — | — | — |
| 10. Isodecyl-oxypropyl Glucohepton-amide | — | — | 0.1 | — | 3.0 | — | — |
| 11. C8/C10 Oxypropyl D-Lactobion-amide | — | — | — | 0.3 | — | 1.0 | — |
| 12. C12 Oxyproply D-Maltobion-amide | — | — | 0.1 | — | — | — | 5.0 |
| 13. C12–C15 Oxyproplypropionamidopropyl D-Gluc | — | — | 0.3 | — | — | 3.0 | — |
| 14. C12–C15 Oxypropyl Gluc 5(oxyethylene) Ether | 1.0 | 1.0 | — | — | — | — | — |
| 15. C12 Oxypropyl Maltobion 4(oxyethylene) Ether | 2.0 | 3.0 | 4.0 | 5.0 | — | 1.0 | — |
| 16. Talc | 1.0 | — | 2.0 | — | — | — | 2.0 |
| 17. Silica | 1.5 | — | — | — | — | — | 0.5 |
| 18. Hydrogenated Castor Oil | — | — | 1.0 | — | — | — | — |
| 19. Dimethicone | — | — | — | — | 1.0 | — | — |
| 20. Cyclomethicone | 46.0 | 44.0 | 51.0 | — | 6.0 | 3.0 | 7.0 |
| 21. Cetyl Dimethicone | — | — | — | — | — | — | 0.5 |
| 22. Stearyl Alcohol | 20.0 | 18.1 | 19.0 | — | — | — | — |
| 23. Stearic Acid | — | — | — | — | 3.0 | — | — |
| 24. Sodium Stearate | — | — | — | 12.0 | — | — | — |
| 25. Magnesium Aluminum Silicate | — | — | — | — | — | 1.0 | — |
| 26. Hydroxypropyl Methyl Cellulose | — | — | — | — | — | 0.4 | — |
| 27. SD Alcohol 40 | — | — | — | — | — | 8.0 | — |
| 28. Witch Hazel Extract | — | — | — | 2.0 | — | — | — |
| 29. Aloe Vera Gel | — | — | — | 2.0 | — | — | — |
| 30. Propylene Glycol | — | — | — | 77.5 | — | — | 3.0 |
| 31. Isopropyl Myristate | — | — | — | — | — | — | 0.5 |
| 32. Ethylene Glycol | — | 1.0 | — | — | — | — | — |

Prototype Anti-Perspirant Compositions Comprising Heteroatom Containing Alkyl Aldonamide Compounds

| Example Ingredients (By Weight) | 158 % | 159 % | 160 % | 161 % | 162 % | 163 % | 164 % |
|---|---|---|---|---|---|---|---|
| Distearate | | | | | | | |
| 33. Glyceryl Stearate | — | 0.4 | — | — | 0.4 | — | — |
| 34. Propyltrimonium Hydrolyzed Collagen | — | — | — | — | 5.0 | — | — |
| 35. Glycosphingolipids | — | — | — | — | 3.0 | — | — |
| 36. Aluminum Zirconium Tetrachlorohydrex glycine | 20.0 | 20.0 | 20.0 | — | — | — | — |
| 37. Aluminum Chlorohydrate | — | — | — | — | 20.0 | 18.0 | 6.5 |
| 38. Aluminum Starch Octenyl Succinate | — | 6.0 | — | — | — | — | — |
| 39. Diazolidinyl Urea | — | — | — | — | 0.3 | — | — |
| 40. Imidazolidinyl Urea | — | — | — | 0.2 | — | — | — |
| 41. Methyl Paraben | — | — | — | — | 0.2 | 0.2 | — |
| 42. Propyl Paraben | — | — | — | — | — | 0.1 | — |
| 43. Fragance | 0.5 | 0.5 | 0.5 | 1.0 | 0.2 | 0.5 | 0.2 |
| 44. Dye (0.2%–1%) | — | — | — | — | — | q.s. | — |
| 45. Water | — | — | — | — | 55.3 | 61.8 | 33.5 |
| 46. Propellant (Isobutane/Propane) | — | — | — | — | — | — | 41.3 |

Example 158

An Antiperspirant Stick Composition

Container A is charged with 20 which is heated to 65° C. with moderate stirring. Mix thoroughly. Add 1 and 2. Mix thoroughly. Slowly add 22. Mix thoroughly. Add 7, 14 and 15. Mix thoroughly. Add 36. Mix thoroughly. Add 16, 17 and 43. Mix thoroughly, cool the mixture to 60° C. and discharge when homogeneous into stick casings.

Example 159

An Antiperspirant Stick Composition

Container A is charged with 20, 5, 32, 33 and 1 which is heated to 65° C. with moderate stirring. Mix thoroughly. Slowly add 22. Mix thoroughly. Add 14, 15, 8 and 9. Mix thoroughly. Add 36. Mix thoroughly. Add 38 and 43. Mix thoroughly, cool the mixture to 60° C. and discharge when homogeneous into stick casings.

Example 160

An Antiperspirant Stick Composition

Container A is charged with 20, 22, 3 and 18 which is heated to 70° C. with moderate stirring. Mix thoroughly. Add 10, 12, 13 and 15. Mix thoroughly. Add 16 and 36. Mix thoroughly. Add 43. Mix thoroughly, cool the mixture to 60° C. and discharge when homogeneous into stick casings.

Example 161

An Antiperspirant Stick Composition

Container A is charged with 30, 29, 40, 11, 15 and 28, which is heated to 75° C. with moderate stirring. Mix thoroughly. Add 24. Mix thoroughly. Add 43. Mix thoroughly, cool the mixture to 60° C. and discharge when homogeneous into stick casings.

Example 162

An Antiperspirant Roll-On Composition

Container A is charged with 45, 41, 23, 33, 5, 7, 8 and 10 which is heated to 80° C. with moderate stirring. Mix thoroughly. Add 34 and 35. Mix thoroughly. Slowly add 37. Mix thoroughly. Add 19, 20, 39 and 43. Mix thoroughly, cool the mixture to room temperature and discharge when homogeneous.

Example 163

An Antiperspirant Roll-On Composition

Container A is charged with 45 and 25 which is heated to 70° C. with rapid stirring. Mix thoroughly. Add 26. Mix thoroughly. Add 27, 20, 4, 11, 13, 15 and 6. Mix thoroughly. Add 37, 41, 42, 43 and 44. Mix thoroughly, cool the mixture to room temperature and discharge when homogeneous.

Example 164

An Antiperspirant Spray Composition

Container A is charged with 20, 21 and 31 which is heated to 70° C. with rapid stirring. Mix thoroughly. Add 45, 17, 16 and 12. Mix thoroughly. Add 37, 30 and 43. Mix thoroughly, cool the mixture to room temperature and discharge when homogeneous into cans and fill with propellent.

Examples 165–168

Prototype Depilatory Compositions Comprising Heteroatom Containing Alkyl Aldonamide Compounds

| Example Ingredients (By Weight) | 165 % | 166 % | 167 % | 168 % | — % | — % | — % |
|---|---|---|---|---|---|---|---|
| 1. PEG-400 | 4.0 | — | — | — | — | — | — |
| 2. PEG-100 Stearate | — | — | 1.3 | — | — | — | — |
| 3. Polysorbate 80 | — | — | 1.0 | — | — | — | — |
| 4. Ceteareth-12 | — | 2.0 | — | — | — | — | — |
| 5. Ceteareth-20 | 4.4 | — | — | — | — | — | — |
| 6. Ethylhexyloxypropyl D-Gluconamide | 1.0 | — | — | 3.0 | — | — | — |
| 7. Isotridecyloxypropyl D-Gluconamide | 1.0 | 2.0 | — | — | — | — | — |
| 8. Gluconyl C12 DL-Alaninate | — | 0.5 | — | — | — | — | — |
| 9. Isodecyloxypropyl Glucoheptonamide | 1.0 | — | — | 2.0 | — | — | — |
| 10. C8/C10 Oxypropyl D-Lactobionamide | 2.0 | 2.0 | — | — | — | — | — |
| 11. C12 Oxypropyl D-Maltobionamide | — | — | — | 3.0 | — | — | — |
| 12. C12-C15 Oxypropylacetamidopropyl D-Gluc | — | — | 5.0 | — | — | — | — |
| 13. C12-C15 Oxypropyl Gluc 5(oxyethylene) Ether | — | 1.0 | — | — | — | — | — |
| 14. C12 Oxypropyl Maltobion 4(oxyethylene) Ether | 3.0 | — | — | — | — | — | — |
| 15. Cetyl Alcohol | 1.0 | — | — | 2.0 | — | — | — |
| 16. Cetearyl Alcohol | 4.4 | 10.0 | — | — | — | — | — |
| 17. Lanolin Alcohol | — | — | 1.0 | — | — | — | — |
| 18. Mineral Oil | — | — | 0.5 | 0.5 | — | — | — |
| 19. Decyl Oleate | — | 3.0 | — | — | — | — | — |

-continued

Prototype Depilatory Compositions Comprising Heteroatom Containing Alkyl Aldonamide Compounds

| Example Ingredients (By Weight) | 165 % | 166 % | 167 % | 168 % | % | % | % |
|---|---|---|---|---|---|---|---|
| 20. Cetyl Acetate | — | — | 1.0 | — | — | — | — |
| 21. Acetylated Lanolin Alcohol | — | — | 1.5 | — | — | — | — |
| 22. Triethylamine Stearate | — | — | — | 1.5 | — | — | — |
| 23. Glyceryl Stearate | — | — | 0.7 | 1.0 | — | — | — |
| 24. Mink Oil | 4.0 | — | — | — | — | — | — |
| 25. Carbomer 940 | — | — | — | 0.3 | — | — | — |
| 26. Urea | — | 4.0 | — | — | — | — | — |
| 27. Seaweed Extract | — | — | — | 5.0 | — | — | — |
| 28. Propylene Glycol | — | — | 5.0 | 1.0 | — | — | — |
| 29. Methylsylanol Manuronate | — | — | — | 2.0 | — | — | — |
| 30. Calcium Thioglycolate | 5.5 | 7.5 | 5.0 | — | — | — | — |
| 31. Calcium Hydroxide | 6.5 | 1.5 | 6.0 | — | — | — | — |
| 32. Magnesium Aluminum Silicate | 3.5 | — | 1.0 | — | — | — | — |
| 33. Titanium Dioxide | — | 5.0 | — | — | — | — | — |
| 34. Tetrasodium EDTA | 1.0 | — | — | — | — | — | — |
| 35. Methyl Paraben | — | — | 0.1 | 0.2 | — | — | — |
| 36. Propyl Paraben | — | — | 0.1 | 0.1 | — | — | — |
| 37. Triethanolamine | — | — | — | 0.3 | — | — | — |
| 38. Fragrance | 0.6 | 0.5 | 0.5 | 0.5 | — | — | — |
| 39. Dye (0.2%–1%) | — | — | q.s. | — | — | — | — |
| 40. Water | 57.2 | 61.0 | 70.3 | 77.6 | — | — | — |

Example 165

A Depilatory Cream

Container A is charged with 40, 32, 34 and 1 which is heated to 90° C. with high sheer stirring. Mix thoroughly. Cool to 75° C. Add 6, 7, 9 and 10. Mix thoroughly. Container B is charged with 24, 16, 5 and 15 which is heated to 75° C. with moderate stirring. Mix thoroughly. Slowly add B to A while stirring. Mix thoroughly. Add 30, 31 and 38. Mix thoroughly, cool the mixture to room temperature and discharge when homogeneous.

Example 166

A Pearlescent Depilatory Cream

Container A is charged with 40, 7, 8, 10, 13 and 26 which is heated to 75° C. with moderate stirring. Mix thoroughly. Container B is charged with 15, 19 and 4 which is heated to 75° C. with moderate stirring. Mix thoroughly. Slowly add A to B while stirring. Mix thoroughly. Add 30, 31, 33 and 38. Mix thoroughly, cool the mixture to room temperature and discharge when homogeneous.

Example 167

A Depilatory Lotion

Container A is charged with 40 and 32 which is heated to 75° C. with rapid stirring. Mix thoroughly. Add 28 and 12. Mix thoroughly. Container B is charged with 18, 17, 3, 20, 21, 2 and 23 which is heated to 75° C. with moderate stirring. Mix thoroughly. Slowly add B to A while stirring. Mix thoroughly. Add 30, 31, 35, 36, 38 and 39. Mix thoroughly, cool the mixture to room temperature and discharge when homogeneous.

Example 168

A Post-Depilatory Lotion

Container A is charged with 40, 25, 28, 27, 35 and 36 which is heated to 75° C. with moderate stirring. Mix thoroughly. Add 6, 9 and 11. Mix thoroughly. Container B is charged with 18, 15, 22 and 23 which is heated to 75° C. with moderate stirring. Mix thoroughly. Slowly add B to A while stirring. Mix thoroughly. Add 29, 37 and 38. Mix thoroughly, cool the mixture to room temperature and discharge when homogeneous.

Examples 169–175

Prototype Preshave/Aftershave Compositions Comprising Heteroatom Containing Alkyl Aldonamide Compounds

| Example Ingredients (By Weight) | 169 % | 170 % | 171 % | 172 % | 173 % | 174 % | 175 % |
|---|---|---|---|---|---|---|---|
| 1. PPG-2 Myristyl Ether Propionate | — | — | — | 3.0 | — | — | — |
| 2. PEG-6 Stearate | — | — | — | — | 4.0 | — | — |
| 3. Ceteth-20 | — | — | — | — | 6.0 | — | — |
| 4. PPG-5 Ceteth-20 | — | — | — | 1.0 | — | — | — |
| 5. Ceteareth-12 | — | 0.5 | — | — | — | — | — |
| 6. Ceteareth-20 | — | 0.5 | — | — | — | — | — |
| 7. Polysorbate-60 | 3.0 | — | — | — | — | — | — |
| 8. SD Alcohol-40 | 30.0 | 20.0 | 20.0 | — | — | 15.0 | 10.0 |
| 9. PEG-400 Stearate | — | — | 0.5 | — | — | — | — |
| 10. Ethylhexyloxy-propyl D-Gluconamide | — | — | — | 1.0 | 1.0 | — | 5.0 |
| 11. Isotridecyloxy-propyl D-Gluconamide (50%) | — | — | — | 1.0 | 2.0 | — | — |
| 12. Isodecyloxy-propyl Glucohept-onamide (50%) | — | — | — | 1.0 | 2.0 | — | — |
| 13. C8/C10 Oxypropyl D-Lactobion-amide (50%) | — | — | — | 3.0 | 1.0 | — | — |
| 14. C12 Oxypropyl D-Maltobion-amide (50%) | — | — | — | 2.0 | 3.5 | — | — |
| 15. C12–C15 Oxypropylacet-amidopropyl D-Gluc | — | 0.1 | — | — | — | 0.1 | — |
| 16. C12–C15 Oxypropyl Gluc 5 (oxyethylene) Ether | 3.0 | — | 3.0 | — | — | — | — |
| 17. C12 Oxypropyl Maltobion 4(oxyethylene) Ether | — | 3.0 | — | — | 5.0 | — | — |
| 18. Stearamido PG-Dimonium Chloride Phosphate | — | — | — | — | — | 1.0 | — |
| 19. Quaternary-15 | — | — | — | — | — | — | 0.1 |
| 20. Hydroxypropyl Cellulose | 1.5 | — | — | — | — | — | — |
| 21. Mineral Oil | 0.5 | — | — | — | 1.0 | — | — |
| 22. Borage Oil | — | — | — | — | 0.5 | — | — |
| 23. Apricot Kernel Oil | — | — | — | — | 1.0 | — | — |
| 24. Calendula Extract | — | — | — | — | 2.0 | — | — |
| 25. Cetyl Alcohol | — | — | — | 3.0 | — | — | — |
| 26. Cetearyl Alcohol | — | — | — | — | — | — | 0.5 |
| 27. Lanolin Alcohol | 1.0 | — | — | — | — | — | — |
| 28. Cabomer 934 | — | 0.4 | — | — | 0.2 | — | — |

-continued

Prototype Preshave/Aftershave Compositions Comprising Heteroatom Containing Alkyl Aldonamide Compounds

| Example Ingredients (By Weight) | 169 % | 170 % | 171 % | 172 % | 173 % | 174 % | 175 % |
|---|---|---|---|---|---|---|---|
| 29. Carbomer 940 | — | — | — | — | — | 0.4 | 0.3 |
| 30. Carbomer 941 | — | — | 0.5 | — | — | — | — |
| 31. Stearic Acid | — | — | — | — | 1.0 | — | — |
| 32. Magnesium Aluminum Silicate | 1.5 | — | — | — | — | — | — |
| 33. Simethicone | 0.2 | — | — | — | — | — | — |
| 34. Dimethicone | 3.0 | — | — | — | — | 2.0 | — |
| 35. Animal Collagen (Soluble) | — | — | — | 0.5 | 0.1 | — | — |
| 36. Tocopheryl Acetate (Vitamin E) | — | — | — | — | 0.1 | — | — |
| 37. Acetamide MEA | — | — | — | 1.5 | — | — | — |
| 38. Lactamide MEA | — | — | — | 1.5 | — | — | — |
| 39. Allantoin | — | 0.2 | — | 0.2 | 0.5 | — | — |
| 40. Menthol | 0.2 | 0.3 | — | 0.2 | — | — | — |
| 41. Aqua Hamamelis | — | 10.0 | — | — | — | — | — |
| 42. β-Carotene (Provitamin A) | — | — | — | — | 0.1 | — | — |
| 43. Propylene Glycol | — | — | — | 0.5 | 0.5 | — | — |
| 44. Glycerin | — | 3.0 | — | — | — | — | 2.0 |
| 45. Butyl Oleate | — | — | 0.2 | — | — | — | — |
| 46. Octyl/Lauryl Myristate | — | — | — | — | 4.0 | — | — |
| 47. Myreth-3 Myristate | — | — | — | — | — | — | 3.0 |
| 48. Glyceryl Stearate | — | 3.0 | — | — | 2.0 | — | — |
| 49. Coconut Caprylate/Caprate | — | 5.0 | — | — | — | — | — |
| 50. Sucrose Distearate | — | — | — | 3.0 | — | — | — |
| 51. Sucrose Stearate | — | — | — | 0.5 | — | — | — |
| 52. Ethyl p-Amino Benzoate | — | — | — | 0.1 | — | — | — |
| 53. Diazolidinyl Urea | — | — | — | 0.2 | 0.2 | 0.2 | — |
| 54. Methyl Paraben | 0.2 | — | — | 0.2 | 0.2 | 0.2 | — |
| 55. Propyl Paraben | 0.1 | — | — | 0.1 | 0.1 | 0.1 | — |
| 56. Triethanolamine | — | — | 0.6 | — | 0.2 | 0.6 | 0.4 |
| 56b. Butylated Hydroxytoluene | — | — | — | — | 0.3 | — | — |
| 57. Sodium Hydroxide (50%) | — | 0.3 | — | — | — | — | — |
| 58. Lactic Acid (10%) pH to 5–7 | — | — | — | q.s. | — | — | — |
| 59. Fragrance | 0.2 | 0.5 | 0.3 | 0.3 | 0.3 | 0.3 | 0.5 |
| 60. Dye (0.2%–1%) | q.s. | — | — | — | — | — | — |
| 61. Water | 55.6 | 53.2 | 74.9 | 76.2 | 66.2 | 75.1 | 78.2 |

Example 169

An Aftershave Lotion Composition

Container A is charged with 32 and (66% of 61) which is heated to 75° C. with rapid stirring. Add 33 and 16. Mix thoroughly. Container B is charged with 34, 7, 21 and 27 which is heated to 75° C. with moderate stirring. Slowly add B to A while stirring. Mix thoroughly. Container C is charged with 40, 8 and (34% of 61). Mix thoroughly. Slowly add 20. Cool container AB to 40° C. Slowly add C to AB while stirring. Mix thoroughly. Add 54, 55, 59 and 60. Mix thoroughly, cool the mixture to room temperature and discharge when homogeneous.

Example 170

An Aftershave Balm Composition

Container A is charged with 6, 5, 48, and 49 which is heated to 75° C. with moderate stirring. Container B is charged with 61, 39 15, 17 and 44 which is heated to 75° C. with moderate stirring. Slowly add B to A while stirring. Container C is charged with 8, 41 and 40. Mix thoroughly. Add 28 and 57. Add C to AB while stirring. Add 59. Mix thoroughly, cool the mixture to room temperature and discharge when homogeneous.

Example 171

An Aftershave Balm Composition

Container A is charged with 8 and 30 which is heated to 40° C. with moderate stirring. Add 45. Container B is charged with 61, 9, 56 and 16 which is heated to 40° C. with moderate stirring. Slowly add B to A while stirring. Add 59. Mix thoroughly, cool the mixture to room temperature and discharge when homogeneous.

Example 172

A Nonalcoholic Aftershave Lotion Composition

Container A is charged with 50, 51, 1, 4 and 25 which is heated to 75° C. with moderate stirring. Add 45. Container B is charged with 61, 37, 38, 35, 39, 43, 53, 54, 55, 10, 11, 12, 13 and 14 which is heated to 75° C. with moderate stirring. Slowly add B to A while stirring. Add 52, 40, 58 and 59. Mix thoroughly, cool the mixture to room temperature and discharge when homogeneous.

Example 173

A Nonalcoholic Aftershave Lotion Composition with Vitamin E

Container A is charged with 2, 3, 31, 46, 21, 23, 24, 42, 36 and 56b which is heated to 75° C. with moderate stirring. Container B is charged with 61, 28, 39, 10, 11, 12, 13 and 14 which is heated to 75° C. with moderate stirring. Slowly add B to A while stirring. Add 22, 56, 53, 54, 55, 35 and 59. Mix thoroughly, cool the mixture to room temperature and discharge when homogeneous.

Example 174

An Aftershave Toner Composition

Container A is charged with (63% of 61), 29, 15 and 17 which is heated to 45° C. with moderate stirring. Add 56. Container B is charged with (37% of 61), 18, and 8 which is heated to 45° C. with moderate stirring. Slowly add B to A while stirring. Add 34, 53, 54, 55 and 59. Mix thoroughly, cool the mixture to room temperature and discharge when homogeneous.

Example 175

An Aftershave Skin Conditioning Composition

Container A is charged with 61, 29, 44, 10 and 19 which is heated to 65° C. with moderate stirring. Container B is charged with 26 and 47 which is heated to 65° C. with moderate stirring. Slowly add B to A while stirring. Cool to 40° C. Add 8, 56 and 59. Mix thoroughly, cool the mixture to room temperature and discharge when homogeneous.

This invention has been described with respect to certain preferred embodiments and various modifications and variations in the light thereof will be suggested to persons skilled in the art and are to be included within the spirit and purview of this application and the scope of the appended claims.

What is claimed is:

1. A personal product composition comprising:
   (a) about 15% by wt. sodium lauryl sulfate;
   (b) about 3% to about 5% by wt. of a heteroatom containing alkyl aldonamide compound having the following structure:

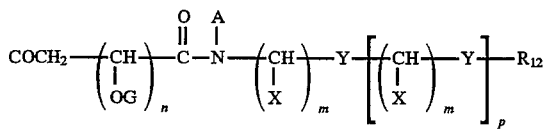

wherein:
$n=1-6$;
$m=1-5$;
$X=H$, a $C_1-C_4$ alkyl group or mixtures thereof;
$Y=NA$, $^+NH_2$, $^+NHA$, O, S, SO, $SO_2$,

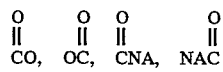

or mixtures thereof;
$p=0-25$;
$G=H$, a mono-, di-, oligo-, polysaccharide group, a $(CH_2CH_2O)_q$—H;
$(CH_2CHCH_3O)_r$—H group or mixtures thereof;
$q=1-50$;
$r=1-50$;
$A=H$, a hydroxy $C_1-C_{18}$ alkyl group, a $C_1-C_{18}$ straight or branched chain, saturated or unsaturated hydrocarbon which may be unsubstituted or substituted with an aromatic, cycloaliphatic, mixed aromatic aliphatic radical or a

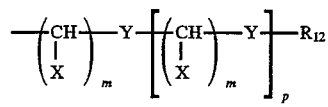

group or mixtures thereof; wherein X, m, Y and p are defined as above; and $R_{12}$ is a straight or branched chain, saturated or unsaturated hydrocarbon which may be unsubstituted or substituted with an aromatic, cycloaliphatic, or mixed aromatic aliphatic radical comprising from about 1 to about 28 carbon atoms;

(c) about 2% by wt. of a viscosity building ionizable salt selected from the group consisting of sodium chloride, potassium chloride, calcium chloride, magnesium chloride, potassium bromide, ammonium chloride, sodium sulfate, potassium sulfate, magnesium sulfate, sodium isethionate, sodium thiosulfate and mixtures thereof;
   (d) about 1% to 40% skin conditioning agent; and
   (e) water.

* * * * *